(12) United States Patent
Robinson et al.

(10) Patent No.: US 7,258,999 B2
(45) Date of Patent: Aug. 21, 2007

(54) PTH RESPONSIVE GENE

(75) Inventors: John Allen Robinson, Downingtown, PA (US); Vedrana Stojanovic-Susulic, Princeton Junction, NJ (US); Philip Babij, Dunstable, MA (US); Richard John Murrills, Yardley, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/705,716

(22) Filed: Nov. 10, 2003

(65) Prior Publication Data

US 2004/0146906 A1 Jul. 29, 2004

Related U.S. Application Data

(60) Provisional application No. 60/425,532, filed on Nov. 12, 2002.

(51) Int. Cl.
*C12P 21/02* (2006.01)
*A61K 38/00* (2006.01)

(52) U.S. Cl. .......................... 435/69.1; 514/2; 530/840
(58) Field of Classification Search .............. 435/69.1; 530/300, 350; 514/2, 12
See application file for complete search history.

(56) References Cited

U.S. PATENT DOCUMENTS

| | | | |
|---|---|---|---|
| 4,683,202 A | 7/1987 | Mullis | |
| 5,107,065 A | 4/1992 | Shewmaker et al. | |
| 5,231,020 A | 7/1993 | Jorgensen et al. | |
| 5,283,173 A | 2/1994 | Fields et al. | |
| 2003/0119043 A1* | 6/2003 | Tanner et al. ................... | 435/6 |

FOREIGN PATENT DOCUMENTS

| | | | |
|---|---|---|---|
| DE | 10126472 A1 * | 8/2002 | |
| EP | 1074617 A2 * | 2/2001 | |
| WO | WO 03/025138 A2 * | 3/2003 | |

OTHER PUBLICATIONS

Vortkamp et al., Science, 273, 613-622 (1996).
Tashjian et al., Journal of Bone & Mineral Research, 17(7), 1151-1161 (2002).
Mierke et al., Current Pharmaceutical Design, 5, 21-36 (1999).
Raynal et al., Biochimica et Biophysica Acta, 1197, 63-93 (1994).
Coghlan et al., Science, 267, 108-111 (1995).
Serebriiskii et al., BioTechniques, 30, 634-655 (2001).
Young, Biology of Reproduction, 58, 302-311 (1998).
Lorch et al., J. Mol. Biol., 186, 821-824 (1985).
Johnston et al., Molecullar & Cellular Biology, 4(8), 1440-1448 (1984).
Zhang et al., Nature, 364, 308-313 (1993).
Ohara et al., Proc. Natl. Acad. Sci, USA, 86, 5673-5677 (1989).
Keegan et al., Science, 231, 699-704 (1986).
Kalpana et al., Science, 266, 2002-2006 (1994).
Loh et al., Science, 243, 217-220 (1989).
Biochemical Journal, 219, 345-373 (1984).
Jones et al., The EMBO Journal, 4(10), 2411-2418 (1985).
Selye, Endocrinology, 16, 547-558 (1932).
Bauer et al., Journal of Exp. Med., 49, 145-162 (1929).
Burr et al., Journal of Bone & Mineral Research, 16(1), 157-165 (2001).
Sadowski et al., Nature, 362, 79-83 (1993).
Brommage et al., The Journal Of Clinical Endocrinology & Metabolism, 84(10), 3757-3763 (1999).
Li et al., FASEB Journal, 7, 957-963 (1993).
Radominska et al., Biochimics et Biophysica Acta, 1195, 63-70 (1994).
Sato et al., Osteoporosis Int., 11, 871-880 (2000).
Cosman et al., Calcified Tissue Int., 62, 475-480 (1998).
Devereux et al., Nucleic Acids Research, 12(1), 387-395 (1984).
Cornish-Bowden, Nucleic Acids Research, 13(9), 3021-3030 (1985).
Dempster et al., Endocrine Reviews, 14(6), 690-709 (1993).
Canalis, The Journal of Clinical Investigation, 106(2), 177-179 (2000).
Neer et al., The New England Journal of Medicine, 344(19), 1434-1441 (2001).
Jerome et al., 28(2), 150-159 (2001).
Clackson, Current Opinion in Chemical Biology, 1, 210-218 (1997).
Lewandoski, Nature Reviews Genetics, 2, 743-755 (2001).
Lanske, et al., The Journal of Clinical Investigation, 104(4), 399-407 (1999).
Martin et al., J. Exp. Med., 182, 1545-1556 (1995).
Chen et al., Proc. Natl. Acad. Sci. USA, 88, 9578-9582 (1991).
Sato et al., Proc. Natl. Acad. Sci. USA, 91, 9238-9242 (1994).
Helps et al., FEBS Letters, 340, 93-98 (1994).
Spaargaren et al., Proc. Natl. Acad. Sci. USA, 91, 12609-12613 (1994).
Elledge et al., Proc. Natl. Acad. Sci. USA, 88, 1731-1735 (1991).
Finley et al., Proc. Natl. Acad. Sci. USA, 91, 12980-12984 (1994).
Brent et al., Annu. Rev. Genet., 31, 663-704 (1997).
Abruzzese et al., Molecular Therapy, 2(3), 276-287 (2000).
Lewandoski, Nature Reviews Genetics, 2, 743-422 (2001).
Wang et al., Proc. Natl. Sci. USA, 91, 8180-8184 (1994).
Kellendonk et al., J. Mol. Biol., 285, 175-182 (1999).
Minamino et al., Circ. Res., 88, 587-592 (2001).

(Continued)

*Primary Examiner*—Kathleen Kerr Bragdon
*Assistant Examiner*—Anand Desai
(74) *Attorney, Agent, or Firm*—Potter Anderson & Corroon LLP

(57) ABSTRACT

This invention relates to a novel PTH gene. The invention further relates to methods of screening, diagnosis and development of therapies for bone related disorders.

10 Claims, 30 Drawing Sheets

OTHER PUBLICATIONS

Vojtek et al., Cell, 74, 204-214 (1993).
Harper et al., Cell, 75, 805-816 (1993).
Brent et al., Cell, 43, 729-736 (1985).
De Almeida et al., Mol. Gen. Genet., 218, 78-86 (1989).
Schedl et al., Cell, 14, 921-929 (1978).
Van Ness et al., Nucleic Acids Research, 19(19), 5143-5151 (1991).
Nagy, Genesis, 26, 99-109 (2000).
Durfee et al., Genes & Development, 7, 555-569 (1993).
Paetkau et al., Genes & Development, 8, 2035-2045 (1994).
Ma et al., Cell, 48, 847-853 (1987).
Wang et al., Nature Biotechnology, 15, 239-243 (1997).
Frenkel et al., Endocrinology, 138(5), 2109-2116 (1997).
Kharode et al., J. Bone Min. Res., Abstract SU365, S523 (1999).
Yeung et al., Genes & Development, 8, 2087-2109 (1994).
Luban et al., 73, 1067-1078 (1993).
Atschul et al., Journal of Molecular Biology, 215, 403-410 (1990).
Abruzzese et al., Human Gene Therapy, 10, 1499-1507 (1999).
Delort et al., Human Gene Therapy, 7, 809-820 (1996).
Golemis et al., Molecular & Cellular Biology, 12(7), 3006-3014 (1992).
Fields et al., Trends Genetics, 10(8), 286-292 (1994).
Gietz et al., Molecular & Cellular Biochemistry, 172, 67-79 (1997).
Masiukiewicz et al., Aging Clin. Exp. Res., 10, 232-239 (1998).
Wang et al., Abstract, Accession No. Q920K5, Dec. 1, 2001.
Tanner et al. BAALC, the human member of a novel mammalian neuroectoderm gene lineage, is implicated in hematopoiesis and acute leukemia. PNAS vol. 98, No. 24:13901-06 (2001).

* cited by examiner

```
                                                                                          Section 1
                      1         10         20         30        40         50        63
Human PAIGB   (1)     MGCGGSRADAIEPRYYESWTRETESTWLTYTDSDAPPSAAAPDSGPEAGGLHSGMLEDGLPSN
Mouse PAIGB   (1)     MGCGGSRADAIEPRYYESWTRETESTWLTYTDSDALPSAAATDSGPEAGGLHAGVLEDGLSSN
Rat PAIGB     (1)     MGCGGSRADAIEPRYYESWTRETESTWLTYTDSDALPSAAATDSGPEAGGLHAGVLEDGPSSN
Consensus     (1)     MGCGGSRADAIEPRYYESWTRETESTWLTYTDSDALPSAAATDSGPEAGGLHAGVLEDGLSSN Section 2
                      64        70        80        90       100       110       126
Human PAIGB   (64)    GVPRSTAPGGIPNPEKKTNCETQCPNPQSLSSGPLTQKQNGLQTTEAKRDAKRMPAKEVTINV
Mouse PAIGB   (64)    GVLRPAAPGGIANPEKKMNCGTQCPNSQNLSSGPLTQKQNGLWATEAKRDAKRMSAREVAINV
Rat PAIGB     (64)    GVLRPAAPGGIANPEKKMNCGTQCPNSQSLSSGPLTQKQNGLWTTEAKRDAKRMSAREVAISV
Consensus     (64)    GVLRPAAPGGIANPEKKMNCGTQCPNSQSLSSGPLTQKQNGLWTTEAKRDAKRMSAREVAINV Section 3
                      127                    146
Human PAIGB   (127)   TDSIQQMDRSRITKNCMN-
Mouse PAIGB   (127)   TENIRQMDRSKRVTKNCIN-
Rat PAIGB     (127)   TENIRQMDRSKRVTKNCIN-
Consensus     (127)   TENIRQMDRSKRVTKNCIN-
```

FIG.4

PTH RESPONSIVE GENE

CROSS-REFERENCE TO RELATED APPLICATION

This application claims priority to U.S. Provisional Application Ser. No. 60/425,532, filed Nov. 12, 2002, incorporated herein by reference in its entirety.

FIELD OF THE INVENTION

The invention is in the field of molecular biology. More specifically, the invention pertains to methods and compositions for the diagnosis, prognosis, prevention, treatment, and evaluation of therapies for bone related disorders.

BACKGROUND OF THE INVENTION

Animals, including humans and other mammals, can be afflicted by a number of bone related disorders such as osteoporosis and Paget's disease. Although the cause of bone related disorders is poorly understood, it is believed that there may be an imbalance between bone formation and bone resorption (bone breakdown). For example, in animals suffering from an osteoporotic condition, bone resorption exceeds bone formation. The complex process of bone formation and bone resorption may be mediated by two cell types: osteoblasts, which is involved in bone formation and osteoclasts, which is involved in bone resorption.

A promising therapeutic approach to the treatment of bone related disorders would be the administration of agents which have been designed to modify the balance between the rate of bone formation and the rate of bone resorption in such a manner that the ratio of the former to the latter is increased, resulting in no net bone loss. For example, the bone loss may be suppressed by inhibiting bone resorption (e.g. inhibiting activity of osteoclasts) or inducing bone formation (e.g. inducing activity of osteoblasts). After the previously occurred bone losses have been restored, a steady state is reached where the rate of bone production and rate of bone resorption are equal. Such a modification may be effected by stimulating the physiological mechanism of bone deposition, i.e., bone formation, or by retarding the mechanism of bone resorption, or both. Drugs presently in use or in the experimental stages for accomplishing these purposes include hormone replacement therapy, selective estrogen receptor modulators (SERMs) (e.g., Raloxifene), bisphosphonates (e.g., alendronate) and calcitonin. These therapeutic treatments reduce bone resoption by decreasing osteoclast generation and reducing osteoclast activity (Canalis E, 2000, J Clin Invest., 106(2): pp 177-179). Although the resulting decrease in bone resorption leads to small increases in bone mineral density (BMD), these drugs do not increase bone matrix deposition or bone volume (Tashjian, A. H., et. al., J. Bone Miner. Res. 17: 1151-1161. 2002). One agent, parathyroid hormone (PTH), when administered once daily stimulates bone matrix formation (Cosman, F. et. al., Calcif. Tissue Int. 62: 475-480, 1998, Neer, R. M., et. al., N. Engl. J. Med. 344:1434-1441, 2001)

PTH and its biologically active fragment PTH 1-34, have been recognized since 1930 that they could exert strong bone forming effects. Interest in bone forming ability of PTH was revived in 1970s and 1980s after numerous clinical studies indicated a bone forming activity of PTH primarily within trabecular bone while with little or no effects on cortical bone (Bauer et al, 1929, J Exp Med, 49: pp 145-162, Selye H, 1932, Endocrinology, 16: pp 547-558, Dempster et al., 1993, Endocrine Reviews, 14(6): pp 690-709, Bauer et al, 1929, J Exp Med, 49: pp 145-162; Selye H, 1932, Endocrinology, 16: pp 547-558). More recent work has shown that the increase in bone formation by PTH increases not only bone mass but improves bone architecture and biomechanical properties (Brommage, R. et. al., J. Clin. Endocrinol. Metab. 84:3757:3763, 1999., Sato, M. et. al., Osteoporos. Int. 11:871-880, 2000., Burr, D. B., et. al., J. Bone Miner. Res. 16:157-165, 2001., Jerome, C. P., et. al., Bone 28:150-159, 2001). Although PTH has these anabolic (bone forming) properties its actions are complex because it can have catabolic (bone degradation) activities under certain treatment regimens (Dempster, D. W. et. al., Endocrine Reviews, 14:690-709, 1993).

A significant need exists to identify novel gene(s) and their protein products for the elucidation of the molecular mechanism of bone modulation or formation, for the screening and development of new drugs, for diagnosis, prognosis, prevention, and treatment of bone development and bone loss disorders, and evaluation of therapies for bone related disorders such as osteoporosis. Furthermore, there is currently a need in the industry for models of bone related disorders, including animal models, to enable screening and identification of compounds for the treatment of these diseases. The present invention overcomes these problems and provides the needed tools.

SUMMARY OF THE INVENTION

The present invention provides a novel PTH responsive gene (PAIGB) and its variants that are regulated by anabolic activity of PTH. The invention further provides isolated nucleic acid fragments encoding PAIGB protein or fragments thereof.

The present invention relates to an isolated nucleic acid fragment encoding a PAIGB polypeptide selected from the group consisting of: (a) an isolated nucleic acid fragment encoding SEQ ID NO: 2, 4, 6, 8 and 10, (b) an isolated nucleic acid fragment encoding an amino acid sequence having at least 85% identity with the SEQ ID NO: 2, 4, 6 8 and 10, (c) an isolated nucleic acid molecule that hybridizes with the isolated nucleic acid fragment of (a) under hybridization conditions of 6×SSC (1M NaCl), 45 to 50% formamide, 1% SDS at 37° C., and a wash in 0.5× to 1×SSC at 55 to 60° C.; and, (d) an isolated nucleic acid fragment that is complementary to (a), (b), or (c). The nucleic acid molecules and corresponding polypeptide fragments are contained in the accompanying sequence listing and described in Brief Description of the Invention.

In another embodiment, the present invention provides for PAIGB polypeptides.

In another embodiment, the instant invention relates to the chimeric constructs encoding PAIGB polypeptide.

In a further embodiment, the present invention concerns a host cell comprising a chimeric construct encoding a PAIGB polypeptide.

In an alternate embodiment, the present invention provides methods of obtaining a nucleic acid fragment encoding the PAIGB polypeptide comprising: (a) probing a genomic library with all or a portion of a nucleic acid fragment as set forth in SEQ ID NO:3; (b) identifying a DNA clone that hybridizes with the nucleic acid fragment of step (a); and determining the sequence of the nucleic acid fragment that comprises the DNA clone identified in step (b).

In another embodiment, the present invention provides for methods of obtaining PAIGB polypeptides.

In yet another embodiment, the present invention provides for a composition for regulating bone-forming activity in a mammal comprising at least one of (i) PAIGB nucleic acid fragment (ii) PAIGB polypetide, or (iii) an antibody formed from such polypetides or portions thereof.

In yet another embodiment, the present invention provides for an agent that alters the expression of PAIGB gene or polypeptide.

In yet another embodiment, the present invention provides for a method of determining whether an agent alters the expression of PAIGB mRNA, the method comprising: a) measuring the level of PAIGB mRNA present in a test sample not contacted with the agent; b) measuring the level of PAIGB mRNA present in the test sample contacted with the agent; and c) determining that the agent alters the expression of PAIGB mRNA when the level of PAIGB mRNA measured in step a) differs from the level of PAIGB mRNA measured in step b).

In yet another embodiment, the present invention provides for a method for screening agents for effectiveness in altering expression of a PAIGB nucleic acid fragment, the method comprising a) contacting a test sample comprising PAIGB nucleic acid fragment with an agent under condition suitable for the expression of the PAIGB nucleic acid fragment, b) detecting altered expression of the PAIGB nucleic acid fragment, and c) comparing the expression of the PAIGB nucleic acid fragment in the presence of varying amounts of the agent and in the absence of the compound.

In yet another embodiment, the present invention provides for a method of screening for agents useful for the treatment of bone related disorders, comprising a) contacting agent with a cultured host cell genetically engineered to express PAIGB gene and, b) detecting a change in the expression of PAIGB gene, PAIGB mRNA or PAIGB polypeptide levels.

In yet another embodiment, the present invention provides for a method for evaluating the efficacy of a treatment of a bone related disorder, in a subject, comprising: for a subject treated with a given protocol; assessing the expression level of a PAIGB nucleic acid fragment or PAIGB polypeptide wherein a change in the expression level of PAIGB nucleic acid fragment or PAIGB polypeptide after the treatment, relative to the level before the treatment, is indicative of the efficacy of the treatment of a bone disorder.

In yet another embodiment, the present invention provides for a method for identifying polypeptides, capable of binding to PAIGB, comprising applying a mammalian two-hybrid procedure in which a sequence encoding said PAIGB is carried by one hybrid vector and sequence from a cDNA or genomic DNA library is carried by the second hybrid vector, the vectors then being used to transform the host cell and the positive transformed cells being isolated, followed by extraction of the said second hybrid vector to obtain a sequence encoding a polypeptide which binds to said PAIGB.

In yet another embodiment, the present invention provides for monitoring the effectiveness of treatment of a subject with a bone related agent comprising the steps of (a) obtaining a pre-administration sample from a subject prior to administration of the agent; (b) detecting the level of expression of a PAIGB protein, mRNA, or genomic DNA in the pre-administration sample; (c) obtaining one or more post-administration samples from the subject; (d) detecting the level of expression or activity of the PAIGB protein, mRNA, or genomic DNA in the post-administration samples; (e) comparing the level of expression or activity of the PAIGB protein, mRNA, or genomic DNA in the pre-administration sample with the PAIGB protein, mRNA, or genomic DNA in the post administration sample or samples; and (f) altering the administration of the agent to the subject accordingly.

In yet another embodiment, the present invention provides for transgenic animal comprising the PAIGB DNA of the present invention.

In yet another embodiment, the present invention provides for a transgenic animal wherein said animal is a "Knock-out" animal in which one or both copies of one of the animal's PAIGB genes have been partially or completely deleted by homologous recombination or gene targeting, or have been inactivated by the insertion or substitution by homologous recombination or gene targeting of exogenous sequences.

In yet another embodiment, the present invention provides for a method for studying bone mass determinants, modulation of bone mass and/or effect of PAIGB on bone disorders using animal model of the present invention.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIG. 3 shows PAIGB cDNA alignment for human, mouse and rat sequences which includes the 5' UTR through to the stop codon (referred to in Example 5).

FIG. 4 shows the protein alignment of rat, mouse and human PAIGB (referred to in Example 5).

Figure 23:
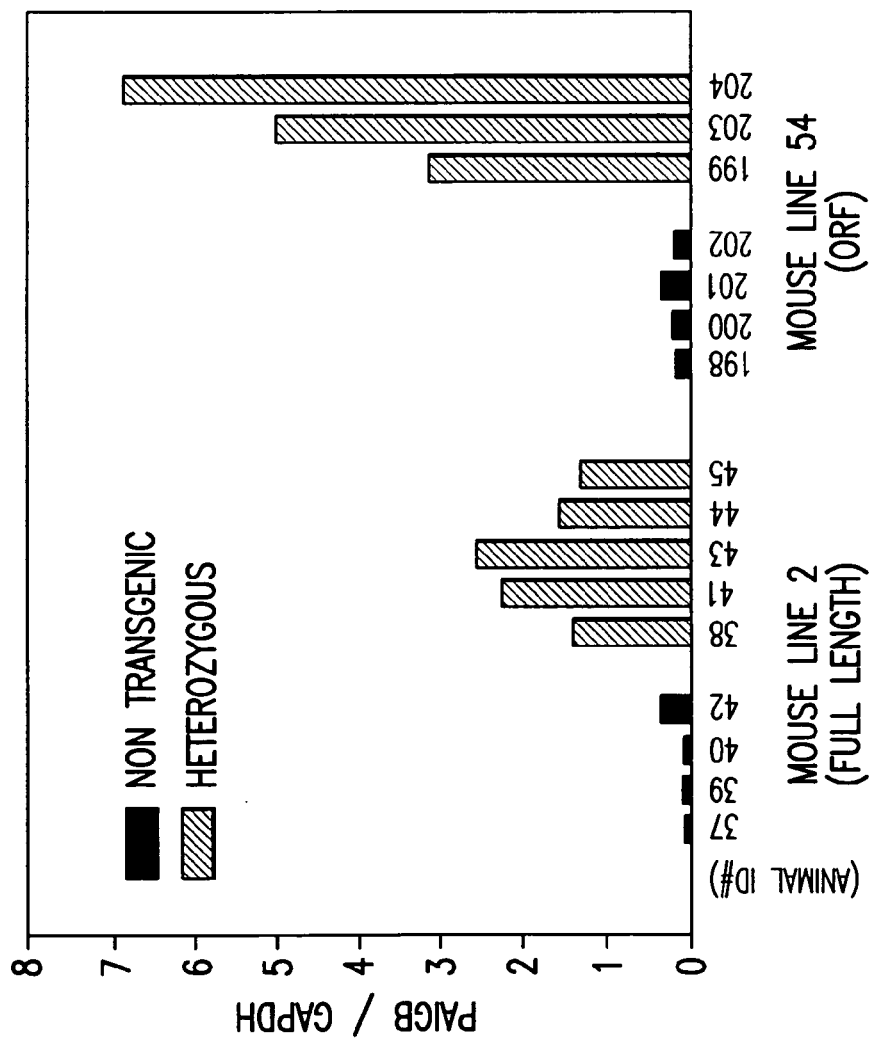

FIG. 23 demonstrates that the heterozygous PAIGB transgenic mice from line 2 and line 54 overexpress PAIGB mRNA compared to the non-transgenic mice in the tibia as determined by real time RT-PCR (referred to in Example 22).

Figure 24:
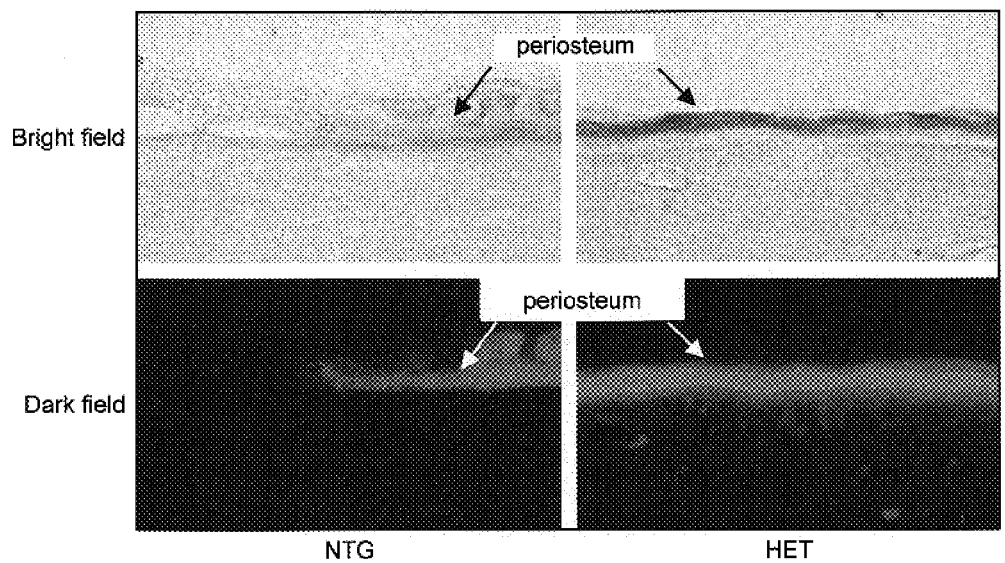

FIG. 24 demonstrates that the PAIGB heterozygous line 2 mice overexpress PAIGB protein in the osteoblastic cells in the periosteum of the calvarium compared to the non-transgenic mice (referred to in Example 22).

Figure 25:
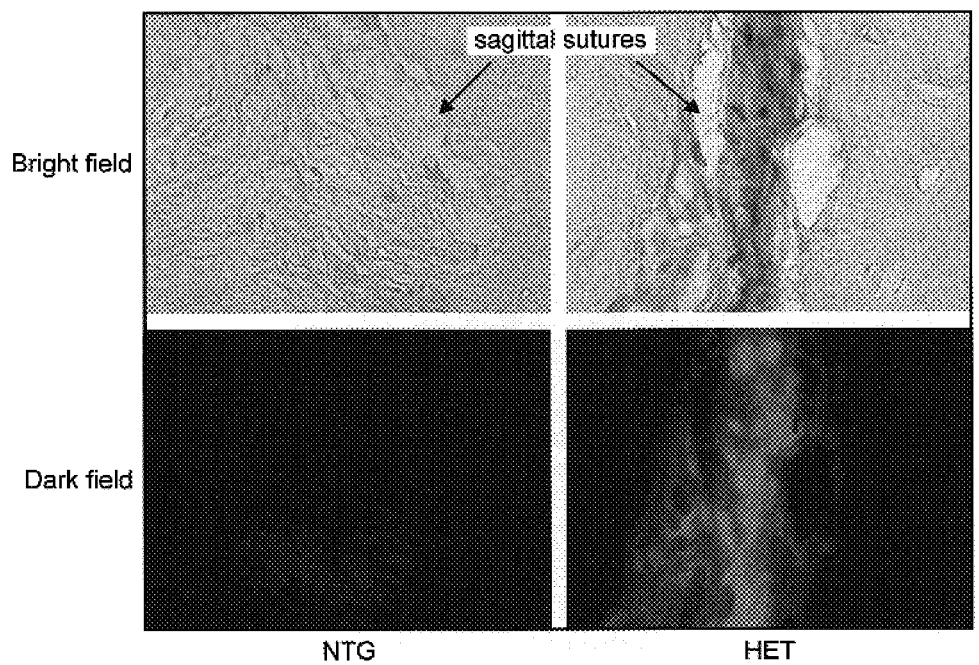

FIG. 25 demonstrates that the PAIGB heterozygous line 2 mice overexpress PAIGB protein in the osteoblastic cells in the sagittal suture area of the calvarium compared to the non-transgenic mice (referred to in Example 22).

Figure 26:
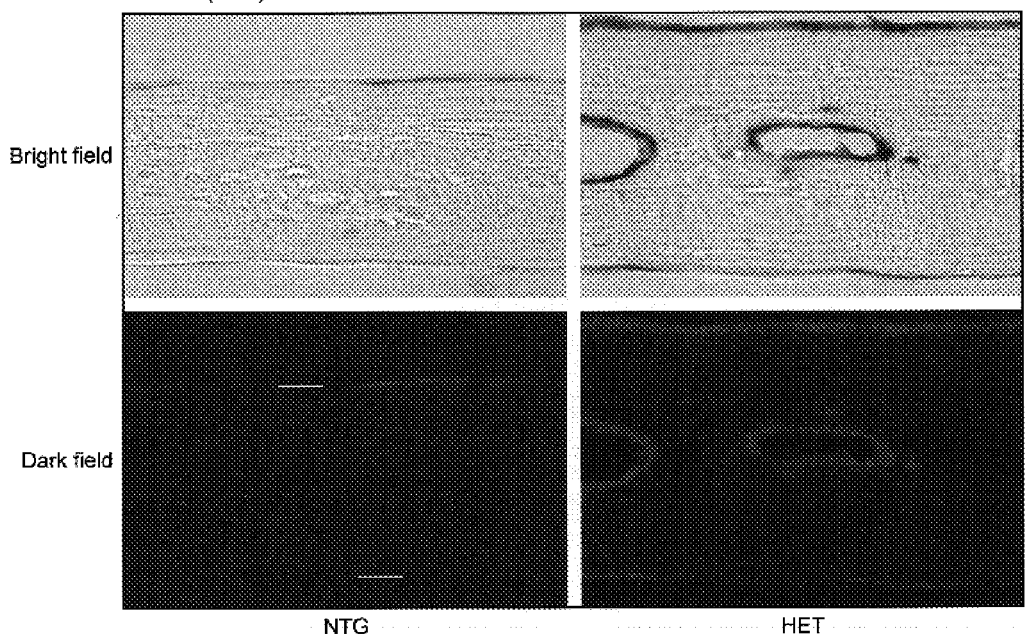

FIG. 26 demonstrates an increase in alkaline phosphatase activity in the periosteum and endosteum of the calvarium of the PAIGB heterozygous line 2 mice compared to non-transgenic mice. The figure further shows an increase in the calvarial thickness in the heterozygous compared to the non-transgenic mice (referred to in Example 22).

Figure 27:
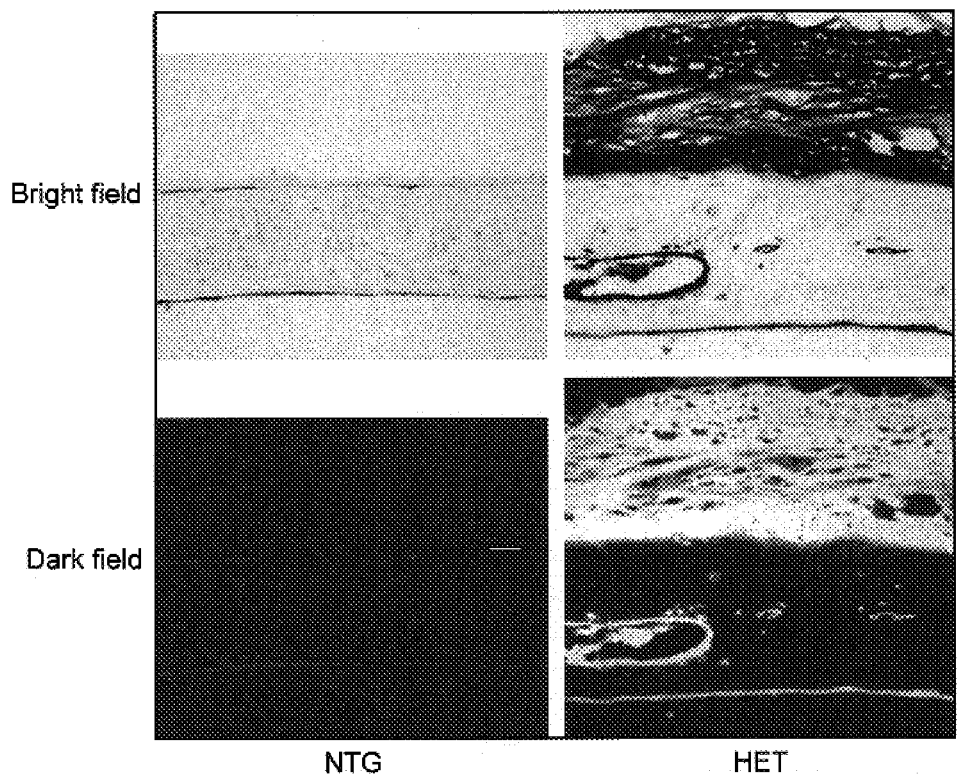

FIG. 27 demonstrates an increase in alkaline phosphatase activity in the periosteum and endosteum of the calvarium of the PAIGB heterozygous line 54 mice compared to non-transgenic mice. The figure further shows an increase in the calvarial thickness in the heterozygous compared to the non-transgenic mice (referred to in Example 22).

The following 63 sequence descriptions and sequence listings attached hereto comply with the rules governing nucleotide and/or amino acid sequence disclosures in patent applications as set forth in 37 C.F.R. §1.821-1.825. ("Requirements for Patent Applications containing nucleotide sequences and/or Amino Acid Sequence Disclosure—the Sequence Rules") and consistent with World Intellectual Property Organization (WIPO) Standard ST.25 (1998) and the sequence listing requirements of the EPO and PCT (Rules 5.2 and 4.95(a-bis) and Section 208 and Annex C of the Administrative Instructions). The Sequence Descriptions contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

SEQ ID NO:1 is a nucleotide sequence of rat PAIGB gene.

SEQ ID NO:2 is an amino acid sequence coded by rat PAIGB gene.

SEQ ID NO:3 is a nucleotide sequence of human PAIGB gene.

SEQ ID NO:4 is an amino acid sequence coded by human PAIGB gene.

SEQ ID NO:5 is a nucleotide sequence of human PAIGB exon 2 splice variant.

SEQ ID NO:6 is an amino acid sequence coded by human PAIGB exon 2 splice variant.

SEQ ID NO:7 is a nucleotide sequence of mouse PAIGB gene.

SEQ ID NO:8 is an amino acid sequence coded by mouse PAIGB gene.

SEQ ID NO:9 is a nucleotide sequence of mouse PAIGB exon 2 splice variant.

SEQ ID NO:10 is an amino acid sequence coded by mouse PAIGB exon 2 splice variant.

SEQ ID NO:11 is a PAIGB amino acid peptide sequence used to immunize animals for polyclonal antibody production.

SEQ ID NO:12 is a PAIGB amino acid peptide sequence used to immunize animals for polyclonal antibody production.

SEQ ID NO:13 is a PAIGB amino acid peptide sequence used to immunize animals for polyclonal antibody production.

SEQ ID NO:14 is a PAIGB amino acid peptide sequence used to immunize animals for polyclonal antibody production.

SEQ ID NO:15 is a mouse nucleotide sequence used to screen for a BAC clone.

SEQ ID NO:16 is a nucleotide sequence of a rat PAIGB TaqMan probe.

SEQ ID NO:17 is a rat PAIGB nucleotide sequence of a forward primer which was used in TaqMan analysis.

SEQ ID NO:18 is a rat PAIGB nucleotide sequence of a reverse primer which was used in TaqMan analysis.

SEQ ID NO:19 is a mouse PAIGB nucleotide sequence of a forward primer which was used in TaqMan analysis.

SEQ ID NO:20 is a mouse PAIGB nucleotide sequence of a reverse primer which was used in TaqMan analysis.

SEQ ID NO:21 is a mouse PAIGB nucleotide sequence of a probe 5' 6FAM used in TaqMan analysis.

SEQ ID NO:22 is a human PAIGB nucleotide sequence of a forward primer which was used in TaqMan analysis.

SEQ ID NO:23 is a human PAIGB nucleotide sequence of a reverse primer which was used in TaqMan analysis.

SEQ ID NO:24 is a human PAIGB nucleotide sequence of a probe 5' 6FAM used in TaqMan analysis.

SEQ ID NO:25 is a nucleotide sequence of a adapter primer AP1 which was used for 5' RACE.

SEQ ID NO:26 is a gene specific primer (GSP1) of PAIGB nucleotide sequence used for 5' RACE.

SEQ ID NO:27 is a gene specific primer (GSP2) of PAIGB nucleotide sequence used for 5' RACE.

SEQ ID NO:28 is a gene specific primer (GSP3) of PAIGB nucleotide sequence used for 5' RACE.

SEQ ID NO:29 is a mouse PAIGB nucleotide sequence used as a forward RT-PCR primer to clone the mouse PAIGB homolog.

SEQ ID NO:30 is a mouse PAIGB nucleotide sequence used as a reverse RT-PCR primer to clone the mouse PAIGB homolog.

SEQ ID NO:31 is a PAIGB nucleotide sequence of a forward RT-PCR primer used to clone mouse PAIGB.

SEQ ID NO:32 is a PAIGB nucleotide sequence of a RT-PCR reverse primer used to clone mouse PAIGB.

SEQ ID NO:33 is a 1,086 bp nucleotide sequence of human PAIGB.

SEQ ID NO:34 is a PAIGB human forward primer used in PCR to clone the exon 2 splice variant.

SEQ ID NO:35 is ae PAIGB human reverse primer used in PCR to clone the exon 2 splice variant.

SEQ ID NO:36 is a PAIGB human forward primer used in PCR with Origene cDNA expression panel.

SEQ ID NO:37 is a PAIGB human reverse primer used in PCR with Origene cDNA expression panel.

SEQ ID NO:38 is a mouse PAIGB nucleotide sequence used as a forward primer in the PCR of the Origene cDNA expression panel.

SEQ ID NO:39 is a mouse PAIGB nucleotide sequence used as a reverse primer in the PCR of the Origene cDNA expression panel.

SEQ ID NO:40 is a nucleotide sequence of mouse PAIGB clone which was used to generate in situ riboprobe.

SEQ ID NO:41 is a human PAIGB exon 2 forward primer used for RT-PCR.

SEQ ID NO:42 is a human PAIGB exon 2 reverse primer used for RT-PCR.

SEQ ID NO:43 is a rat PAIGB exon 2 forward primer used for RT-PCR.

SEQ ID NO:44 is a rat PAIGB exon 2 reverse primer used for RT-PCR.

SEQ ID NO:45 is a rat PAIGB exon 2 forward primer used in Taqman to assess PAIGB transgene expression in transgenic animals.

SEQ ID NO:46 is a rat PAIGB exon 2 reverse primer used in Taqman to assess PAIGB transgene expression in transgenic animals.

SEQ ID NO:47 is a rat PAIGB probe used in Taqman to assess PAIGB transgene expression in transgenic animals.

SEQ ID NO:48 is a rat PAIGB siRNA sense strand oligonucleotide.

SEQ ID NO:49 is a rat PAIGB siRNA antisense strand oligonucleotide for SEQ ID NO 48.

SEQ ID NO:50 is a rat PAIGB siRNA sense strand oligonucleotide.

SEQ ID NO:51 is ae rat PAIGB siRNA antisense strand oligonucleotide for SEQ ID NO 50.

SEQ ID NO:52 is a rat PAIGB siRNA sense strand oligonucleotide.

SEQ ID NO:53 is a rat PAIGB siRNA antisense strand oligonucleotide for SEQ ID NO 52.

SEQ ID NO:54 is a rat PAIGB siRNA sense strand oligonucleotide.

SEQ ID NO:55 is a rat PAIGB siRNA antisense strand oligonucleotide for SEQ ID NO 54.

SEQ ID NO:56 is a human PAIGB siRNA sense strand oligonucleotide.

SEQ ID NO:57 is a human PAIGB siRNA antisense strand oligonucleotide for SEQ ID NO 56.

SEQ ID NO:58 is a human PAIGB siRNA sense strand oligonucleotide.

SEQ ID NO:59 is a human PAIGB siRNA antisense strand oligonucleotide for SEQ ID NO 58.

SEQ ID NO:60 is a human PAIGB siRNA sense strand oligonucleotide.

SEQ ID NO:61 is a human PAIGB siRNA antisense strand oligonucleotide for SEQ ID NO 60.

SEQ ID NO:62 is a human PAIGB siRNA sense strand oligonucleotide.

SEQ ID NO:63 is a human PAIGB siRNA antisense strand oligonucleotide for SEQ ID NO 62.

DETAILED DESCRIPTION OF THE INVENTION

Applicants have succeeded in identifying and characterizing a novel PTH responsive gene and its variants that are regulated by anabolic activity of PTH. This newly identified gene is called PTH Anabolic Induced Gene in Bone (PAIGB). PAIGB gene was identified both on the basis of expression of PAIGB upon intermittent administration of fragment 1-34 of human PTH into rats as well as comparison of the nucleotide sequences to the public NCBI database (GeneBank) using algorithms well known in the art.

In one embodiment, Applicants provide evidence that PAIGB is regulated by anabolic activity of PTH and should represent a molecule that mediates anabolic PTH activity. PAIGB's expression in bone was dramatically increased when PTH was administered in intermittent manner whereas continuous PTH administration did not induce any changes in the expression level of this novel gene.

In another embodiment, the expression of PAIGB in normal non-treated or non-diseased bone was very low or undetectable when measured by Taq-man analysis. However, after intermittent PTH treatment, the level of mRNA for PAIGB was induced significantly in a dose and time dependent manner. Furthermore, there was no induction of PAIGB expression with continuous administration of PTH. The increased expression of PAIGB during intermittent PTH treatment reflects the increased bone formation induced by PTH treatment. This invention further describes the identification and signaling events involved in regulation of gene expressed upon PTH treatment in the manner to induce bone formation.

In yet another embodiment, the novel PTH responsive gene of the present invention, PAIGB, was expressed in limited fashion with high level of expression in brain, and low levels of expression in kidney and lung. PTH administered in an intermittent manner did not induce any changes in message for PAIGB in kidney, heart and brain, which data indicates that the PTH induced PAIGB expression is specific to bone tissues. Interestingly, expression of PAIGB in bone correlated with the changes in BMD (bone mineral density) With intermittent PTH administeration. The level of PAIGB expression as well as osteoblast specific expression especially in the periosteum clearly indicates a valid role for PAIGB.

In yet another embodiment, the PTH induction of PAIGB expression was PTH receptor specific. Furthermore, the effect of PTH on PAIGB expression was mediated via cAMP accumulation and subsequent activation of PKA; thus confirming again that PAIGB is involved in molecular mechanisms that underlay PTH bone forming activities.

In yet another embodiment, the expression of PAIGB polypeptide is detected using various techniques such as Western blotting, immunohistochemical methods, immunofluorescence microscopy and flow cytometry.

The present invention relates to genetically modified animals baring alterations to the PAIGB gene. These animals model PAIGB altered expression associated with bone diseases, display a major phenotype characterized by the bone anabolic function, and are useful for identifying compounds for the treatment of human disease. Therefore, the invention also relates to methods of using the animals for identifying compounds effective for the treatment of bone related disorders and to the compounds themselves.

Definition of Abbreviations and Terms:

The following definitions are provided for the full understanding of terms and abbreviations used in this specification.

As used herein and in the appended claims, the singular forms "a", "an", and "the" include the plural reference unless the context clearly indicates otherwise. Thus, for example, a reference to "a host cell" includes a plurality of such host cells, and a reference to "an antibody" is a reference to one or more antibodies and equivalents thereof known to those skilled in the art, and so forth.

The abbreviations in the specification correspond to units of measure, techniques, properties or compounds as follows: "Sec" means second(s), "min" means minutes, "h" means hour(s), "d" means day(s), "kg" means kilogram(s), "g" means gram(s), "mg" means milligram(s), "µg" means microgram(s), "ng" means nanogram(s), "kDa" means kilodalton(s), "° C." means degree(s) Celsius, "cm" means centimeter(s), "µL" means microliter(s), "mL" means milliliter(s), "pL" means pico liters", "mM" means millimolar, "M" means molar, "mmole" means millimole(s), "kb" means kilobase, "bp" means base pair(s), "RT" means room temperature, "nm" means nanometer, "SEM" means standard error of the mean, "Δ" means change, "ct" means threshold cycle, and "IU" means International Units.

"High performance liquid chromatography" is abbreviated HPLC.

"Rapid amplification of differentially expressed genes" is abbreviated RADE.

"High throughput screening" is abbreviated HTS.

"Polyacrylamide gel electrophoresis" is abbreviated PAGE.

"Polymerase chain reaction" is abbreviated PCR.

"Reverse transcriptase polymerase chain reaction" is abbreviated RT-PCR.

"Enzyme linked immunosorbent assay" is abbreviated ELISA

"Radioimmunoassay" is abbreviated RIA.

"Mass-spectroscopy" is abbreviated MS.

"Tandem mass-spectroscopy" is abbreviated MS/MS.

SQ 22536 adenylate cyclase inhibitor is abbreviated SQInh.

Liquid chromatography is abbreviated LC.

Liquid chromatography tandom mass spectroscopy is abbreviated LC-MS-MS.

"Sodium dodecyl sulfate" is abbreviated SDS.

"Tris buffered Saline Tween 20" is abbreviated TBST.

"Tris buffered Saline" is abbreviated TBS "Sodium dodecyl sulfate" is abbreviated SDS.

"Glyceraldehyde-3-phosphate dehydrogenase" is abbreviated GAPDH.

"Untranslated region" is abbreviated UTR.

"Open reading frame" is abbreviated ORF.

"Parathyroid hormone" is abbreviated PTH.

"PTH Anabolic Induced Gene in Bone" is abbreviated PAIGB.

"Bone Mineral Density" is abbreviated BMD.

"Gene specific primer" is abbreviated GSP.

"Subcutaneous" is abbreviated sc or s.c.

"Prostaglandin $E_2$" is abbreviated PGE2.

"Non-transgenic" is abbreviated NTG.

"Heterozygous" is abbreviated HET.

In the context of this disclosure, a number of terms shall be utilized. As used herein, the term "nucleic acid molecule" refers to the phosphate ester form of ribonucleotides (RNA molecules) or deoxyribonucleotides (DNA molecules), or any phosphoester analogs, in either single stranded form, or a double-stranded helix. Double stranded DNA-DNA, DNA-RNA and RNA-RNA helices are possible. The term nucleic acid molecule, and in particular DNA or RNA molecule, refers to the primary and secondary structure of the molecule, and does not limit it to any particular tertiary forms. Thus, this term includes double-stranded DNA found, inter alia, in linear (e.g., restriction fragments) or circular DNA molecules, plasmids, and chromosomes. In discussing the structure of particular double-stranded DNA molecules, sequences may be described according to the normal convention of giving only the sequence in the 5' to 3' direction along the nontranscribed strand of DNA (i.e., the strand having a sequence homologous to the mRNA).

A "recombinant nucleic acid molecule" is a nucleic acid molecule that has undergone a molecular biological manipulation, i.e., non-naturally occurring nucleic acid molecules. Furthermore, the term "recombinant DNA molecule" refers to a nucleic acid sequence which is not naturally occurring, or can be made by the artificial combination of two otherwise separated segments of sequence, i.e., by ligating together pieces of DNA that are not normally continguous. By "recombinantly produced" is meant artificial combination often accomplished by either chemical synthesis means, or by the artificial manipulation of isolated segments of nucleic acids, e.g., by genetic engineering techniques using restriction enzymes, ligases, and similar recombinant techniques as described by, for example, Sambrook et al., (Molecular Cloning, second edition, Cold Spring Harbor Laboratory, Plainview, N.Y.; (1989)), Ausubel et al., Current Protocols in Molecular Biology, Current Protocols (1989), and DNA Cloning: A Practical Approach, Volumes I and II (ed. D. N. Glover) IREL Press, Oxford, 1985. Such is usually done to replace a codon with a redundant codon encoding the same or a conservative amino acid, while typically introducing or removing a sequence recognition site. Alternatively, it may be performed to join together nucleic acid segments of desired functions to generate a single genetic entity comprising a desired combination of functions not found in the common natural forms. Restriction enzyme recognition sites are often the target of such artificial manipulations, but other site specific targets, e.g., promoters, DNA replication sites, regulation sequences, control sequences, or other useful features may be incorporated by design. Examples of recombinant nucleic acid molecule include recombinant vectors, such as cloning or expression vectors which contain DNA sequences encoding phi gene proteins which are in a 5' to 3' (sense) orientation or in a 3' to 5' (antisense) orientation.

The terms "polynucleotide", "nucleotide sequence", nucleic acid, nucleic acid molecule, nucleic acid sequence, oligonucleotide, or any fragment thereof, refers to series of nucleotide bases (also called "nucleotides") in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and antisense polynucleotide. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil, or containing carbohydrate, or lipids.

An "anti-sense" copy of a particular polynucleotide refers to a complementary sequence that is capable of hydrogen bonding to the polynucleotide and can therefor, be capable of modulating expression of the polynucleotide. These are DNA, RNA or analogs thereof, including analogs having altered backbones, as described above. The polynucleotide to which the anti-sense copy binds may be in single-stranded form or in double-stranded form. A DNA sequence linked to a promoter in an "anti-sense orientation" may be linked to the promoter such that an RNA molecule complementary to the coding mRNA of the target gene is produced.

The term "sense" refers to sequences of nucleic acids that are in the same orientation as the coding mRNA nucleic acid sequence. A DNA sequence linked to a promoter in a "sense orientation" is linked such that an RNA molecule which contains sequences identical to an mRNA is transcribed. The produced RNA molecule, however, need not be transcribed into a functional protein.

"RNA transcript" refers to the product resulting from RNA polymerase-catalyzed transcription of a DNA sequence. When the RNA transcript is a complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense RNA" refers to an RNA transcript that includes the mRNA and can be translated into a polypeptide by the cell. "Anti-sense RNA" refers to an RNA transcript that is complementary to all or part of a target primary transcript or mRNA and that can block the expression of a target gene (U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

A "sense" strand and an "anti-sense" strand when used in the same context refer to single-stranded PAIGB polynucleotides which are complementary to each other. They may be opposing strands of a double-stranded polynucleotide, or one strand may be predicted from the other according to generally accepted base-pairing rules. Unless otherwise specified or implied, the assignment of one or the other strand as "sense" or "antisense" is arbitrary.

"siRNA" refers to small interfering RNAs, that are capable of causing interference and can cause post-transcriptional silencing of specific genes in cells, for example, mammalian cells (including human cells) and in the body, for example, mammalian bodies (including humans). The phenomenon of RNA interference is described and discussed in Bass, Nature 411: 428-29 (2001); Elbahir et al., Nature 411: 494-98 (2001); and Fire et al., Nature 391: 806-11 (1998), where methods of making interfering RNA also are discussed. An "siRNA" or "RNAi" forms a double stranded RNA, which double stranded RNA has the ability to reduce or inhibit expression of a gene or target gene when the siRNA expressed in the same cell as the gene or target gene. "siRNA" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. The sequence of the siRNA can correspond to the full length target gene, or a subsequence thereof.

The polynucleotides may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The nucleic acids may also be modified by many means known in the art. Non-limiting examples of such modifications include methylation, "caps", substitution of one or more naturally occurring nucleotides with an analog, and internucleotide modifications such as, for example, those with uncharged linkages (e.g., methyl phosphonates, phosphotriesters, phosphoroamidates carbamates) and with charged linkages (e.g., phosphorothioates, phosphorodithioates). Polynucleotides may contain one or more additional covalently linked moieties, such as, for example, proteins (e.g., nucleases, toxins, antibodies, signal peptides, poly-L-lysine), intercalators (e.g., acridine, psoralen), chelators (e.g., metals, reactive metals, iron, oxidative metals), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

The terms "nucleic acid" or "nucleic acid sequence", "nucleic acid molecule", "nucleic acid fragment" or "polynucleotide" may be used interchangeably with gene, mRNA encoded by a gene and cDNA.

The term "polynucleotide encoding polypeptide" encompasses a polynucleotide which may include only the coding sequence as well as a polynucleotide which may include additional coding or non-coding sequence.

A nucleic acid molecule is "hybridizable" to another nucleic acid molecule, such as cDNA, genomic DNA, or RNA, when a single stranded form of the nucleic acid molecule can anneal to the other nucleic acid molecule under the appropriate conditions of temperature and solution ionic strength (Sambrook, J. et al. eds., *Molecular Cloning: A Laboratory Manual* (2d Ed. 1989) Cold Spring Harbor Laboratory Press, NY. Vols. 1-3 (ISBN 0-87969-309-6)). The conditions of temperature and ionic strength determine the "stringency" of the hybridization. For preliminary screening for homologous nucleic acids, low stringency hybridization conditions, corresponding to a $T_m$ of 55° C., can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SSC. High stringency hybridization conditions correspond to the highest $T_m$, e.g., 50% formamide, 5× or 6×SSC. Hybridization requires that the two nucleic acids contain complementary sequences, although depending on the stringency of the hybridization, mismatches between bases are possible. The appropriate stringency for hybridizing nucleic acids depends on the lenth of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (Sambrook et al. eds., *Molecular Cloning: A Laboratory Manual* (2d Ed. 1989) Cold Spring Harbor Laboratory Press, NY. Vols. 1-3 (ISBN 0-87969-309-6), 9.50-9.51). For hybridization with shorter nucleic acids, i.e., oligonucleotides, the position of mismatches becomes more important, and the length of the oligonucleotide determines its specificity (Sambrook et al. eds., *Molecular Cloning: A Laboratory Manual* (2d Ed. 1989) Cold Spring Harbor Laboratory Press, NY. Vols. 1-3 (ISBN 0-87969-309-6) 11.7-11.8).

The term "complementary" is used to describe the relationship between nucleotide bases that are capable to hybridizing to one another. For example, with respect to DNA, adenosine is complementary to thymine and cytosine is complementary to guanine.

"Identity" or "similarity", as known in the art, are relationships between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. Both identity and similarity can be readily calculated by known methods such as those described in: *Computational Molecular Biology*, Lesk, A. M., ed., Oxford University Press, New York, 1988; *Biocomputing: Informatics and Genome Projects*, Smith, D. W., ed., Academic Press, New York, 1993; *Sequence Analysis in Molecular Biology*, von Heinje, G., Academic Press, 1987; *Computer Analysis of Sequence Data*, Part I, Griffin, A. M., and Griffin, H. G., eds., Humana Press, New Jersey, 1994; and *Sequence Analysis Primer*, Gribskov, M. and Devereux, J., eds., M Stockton Press, New York, 1991. Methods commonly employed to determine identity or similarity between sequences include, but are not limited to those disclosed in Carillo, H., and Lipman, D., SIAM *J Applied Math*., 48:1073 (1988). Methods to determine identity and similarity are codified in publicly available computer programs. Preferred computer program methods to determine identity and similarity between two sequences include, but are not limited to, GCG program package (Devereux, J., et al., *Nucleic Acids Research* 12(1): 387 (1984)), BLASTP, BLASTN, and FASTA (Atschul, S. F. et al., *J Molec. Biol.* 215: 403 (1990)).

"Homologous" refers to the degree of sequence similarity between two polymers (i.e. polypeptide molecules or nucleic acid molecules). The homology percentage figures referred to herein reflect the maximal homology possible between the two polymers, i.e., the percent homology when the two polymers are so aligned as to have the greatest number of matched (homologous) positions.

The term "percent homology" refers to the extent of amino acid sequence identity between polypeptides. The homology between any two polypeptides is a direct function of the total number of matching amino acids at a given position in either sequence, e.g., if half of the total number of amino acids in either of the sequences are the same then the two sequences are said to exhibit 50% homology.

The term "fragment", "analog", and "derivative" when referring to the polypeptide of the present invention (e.g. SEQ ID NOs:2, 4, 6, 8, 10), refers to a polypeptide which may retain essentially the same biological function or activity as such polypeptide. Thus, an analog includes a precursor protein which can be activated by cleavage of the precursor protein portion to produce an active mature polypeptide. The fragment, analog, or derivative of the polypeptide of the present invention (e.g. SEQ ID NOs:2, 4, 6, 8, 10) may be one in which one or more of the amino acids are substituted with a conserved or non-conserved amino acid residue and such amino acid residue may or may not be one encoded by the genetic code, or one in which one or more of the amino acid residues includes a substituent group, or one in which the polypeptide is fused with a compound such as polyethylene glycol to increase the half life of the polypeptide, or one in which additional amino acids are fused to the polypeptide such as a signal peptide or a sequence such as polyhistidine tag which is employed for the purification of the polypeptide or the precursor protein. Such fragments, analogs, or derivatives are deemed to be within the scope of the present invention.

"Conserved" residues of a polynucleotide sequence are those residues that occur unaltered in the same position of two or more related sequences being compared. Residues that are relatively conserved are those that are conserved amongst more related sequences than residues appearing elsewhere in the sequences.

Related polynucleotides are polynucleotides that share a significant proportion of identical residues.

Different polynucleotides "correspond" to each other if one is ultimately derived from another. For example, messenger RNA corresponds to the gene from which it is transcribed. cDNA corresponds to the RNA from which it has been produced, such as by a reverse transcription reaction, or by chemical synthesis of a DNA based upon knowledge of the RNA sequence. cDNA also corresponds to the gene that encodes the RNA. Polynucleotides also "correspond" to each other if they serve a similar function, such as encoding a related polypeptide, in different species, strains or variants that are being compared.

The polypeptide and the polynucleotides of the present invention are preferably provided in an isolated form, and may be purified to homogeneity by procedures well-known in the art.

The term "isolated" means that the material is removed from its original or native environment (e.g., the natural environment if it is naturally occurring). Therefore, a naturally-occurring polynucleotide or polypeptide present in a living animal is not isolated, but the same polynucleotide or polypeptide, separated by human intervention from some or all of the coexisting materials in the natural system, is isolated. For example, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA and combined with carbohydrate, lipids, protein or other materials. Such polynucleotides could be part of a vector and/or such polynucleotides or polypeptides could be part of a composition, and still be isolated in that such vector or composition is not part of the environment in which it is found in nature. Similarly, the term "substantially purified" refers to a substance, which has been separated or otherwise removed, through human intervention, from the immediate chemical environment in which it occurs in Nature. Substantially purified polypeptides or nucleic acids may be obtained or produced by any of a number of techniques and procedures generally known in the field.

The terms "substantially pure" and "isolated" are not intended to exclude mixtures of polynucleotides or polypeptides with substances that are not associated with the polynucleotides or polypeptides in nature.

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme.

"Codon degeneracy" refers to divergence in the genetic code permitting variation of the polynucleotide sequence without effecting the amino acid sequence of an encoded polypeptide. Accordingly, the present invention relates to any nucleic acid fragment that encodes all or a substantial portion of the amino acid sequence of instant PAIGB protein as set forth in SEQ ID NOs: 2, 4, 6, 8, 10. The skilled artisan is well aware of the "codon-bias" exhibited by a specific host cell to use nucleotide codons to specify a given amino acid. Therefore, when synthesizing a gene for improved expression in a host cell, it is desirable to design the gene such that its frequency of codon usage approaches the frequency of preferred codon usage of the host cell.

A "substantial portion" of an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computer automated sequence comparison and identification using algorithms such as BLAST (Basic Local Alignment Search Tool; Altschul, S. F., et al., (1993) J. Mol. Biol. 215:403-410; see also www.ncbi.nlm.nih.gov/BLASTO.

Accordingly, a "substantial portion" of a nucleotide sequence comprises enough of the sequence to specifically identify and/or isolate a nucleic acid fragment comprising the sequence. The present specification teaches partial or complete amino acid and nucleotide sequences encoding one or more particular PAIGB variants. The skilled artisan, having the benefit of the sequences as reported herein, may now use all or a substantial portion of the disclosed sequences for purposes known to those skilled in this art. Accordingly, the present invention comprises the complete sequences as reported in the accompanying Sequence Listing, as well as substantial portions of those sequences as defined above.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well known procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determining preferred codons can be based on a survey of genes derived from the host cell where sequence information is available.

"Gene" refers to a nucleic acid fragment that expresses a specific protein, including regulatory sequences preceding (5' noncoding sequences) and following (3' non-coding sequences) the coding sequence. "Native gene" refers to a gene as found in nature with its own regulatory sequences. "Chimeric gene" or "chimeric construct" refers to any gene or a construct, not a native gene, comprising regulatory and coding sequences that are not found together in nature. Accordingly, a chimeric gene or chimeric construct may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Gene control sequence" refers to the DNA sequences required to initiate gene transcription plus those required to regulate the rate at which initiation occurs. Thus a gene control sequence may consist of the promoter, where the general transcription factors and the polymerase assemble, plus all the regulatory sequences to which gene regulatory proteins bind to control the rate of these assembly processes at the promoter. For example, the control sequences that are suitable for prokaryotes may include a promoter, optionally an operator sequence, and a ribosome binding site. Eukaryotic cells may utilize promoters, enhancers, and/or polyadenylation signals.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions.

"Bone specific promoter" refers to promoters such as the osteonectin promoter described by McVey et al., J. Biol. Chem., 263:1,111-11,116 (1988) or BMP.

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency.

The term "operatively linked" refers to the association of two or more nucleic acid fragments on a single nucleic acid fragment so that the function of one is affected by the other. For example, a promoter is operatively linked with a coding sequence when it is capable of affecting the expression of that coding sequence (i.e., that the coding sequence is under the transcriptional control of the promoter). Coding sequences can be operatively linked to regulatory sequences in sense or antisense orientation.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "expression" refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein.

"Overexpression" refers to the production of a gene product in an organism that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in organisms in amounts or proportions that differ from that of normal or non-transformed organisms. Over expression of the polypeptide of the present invention may be accomplished by first constructing a chimeric gene or chimeric construct in which the coding region is operatively linked to a promoter capable of directing expression of a gene or construct in the desired tissues at the desired stage of development. For reasons of convenience, the chimeric gene or chimeric construct may comprise promoter sequences and translation leader sequences derived from the same genes. 3' Non-coding sequences encoding transcription termination signals may also be provided. The instant chimeric gene or chimeric construct may also comprise one or more introns in order to facilitate gene expression. Plasmid vectors comprising the instant chimeric gene or chimeric construct can then be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene or chimeric construct. The skilled artisan will also recognize that different independent transformation events will result in different levels and patterns of expression (Jones et al. (1985) *EMBO J.* 4:2411-2418; De Almeida et al. (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

A "cassette" refers to a DNA coding sequence or segment of DNA that codes for an expression product that can be inserted into a vector at defined restriction sites. The cassette restriction sites are designed to ensure insertion of the cassette in the proper reading frame. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct."

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal. Host cell can be used as a recipient for vectors and may include any transformable organisms that is capable of replicating a vector and/or expressing a heterologous nucleic acid encoded by a vector.

"Clone" refers to a population of cells derived from a single cell or common ancestor by mitosis The term "expression system" refers to a host cell and compatible vector under suitable conditions, e.g. for the expression of a protein coded for by foreign DNA carried by the vector and introduced to the host cell. Common expression systems include but are not limited to *E. coli* host cells and plasmid vectors, insect host cells and Baculovirus vectors, and mammalian host cells and vectors.

The term "modified phenotype" refers to a change in the form, character, or intensity of a physical or biochemical characteristic displayed by host cells under a particular set of environmental factors. A phenotype might be displayed by a given host cell in response to any number of environmental factors including, but not limited to temperature, exposure to certain molecules, or signaling by and extracellular molecule (e.g., a hormone), or another cell. In certain embodiments a given predetermined phenotype, and any modifications of that phenotype may be those which occur naturally in a given host cell. In another embodiments, a host cell is engineered such that a more easily detectable phenotype is substituted into a transcriptional pathway of interest. For example, a reporter gene may be inserted in operable association with a promoter in a cellular regulatory pathway of interest. In either case, it is preferred that the phenotype of interest, and any modifications of that phenotype that are contemplated, are "predetermined," i.e., they are known and well characterized, and are readily detectable in the host cell used to screen and/or select for regulator molecules thereof of the present invention.

"Transformation" refers to the transfer of a nucleic acid fragment into the genome of a host organism, resulting in genetically stable inheritance. Host organisms containing the transformed nucleic acid fragments are referred to as "transgenic" organisms.

The term "gene inducible system" refers to the use of ligands to regulate gene expression. Several regulatory systems have been developed that utilize small molecules to induce gene expression (reviewed in Clackson T. Curr Opin Chem Biol. 1997;1:210-218; Lewandoski M. Nat Rev Genet. 2001; 2:743-755). A gene inducible system is a molecular tool which allows for low to undetectable basal expression of a target gene when the system is not activated and increased expression levels of the target gene when the system is activated.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides include but are not limited to intracellular localization signals.

Polypeptides of the present invention also includes variants of the aforementioned polypeptides, including all allelic forms and splice variants. Such polypeptides vary from the reference polypeptide by insertions, deletions, and substitutions that may be conservative or non-conservative, or any combination thereof. The term "variant" refers to a "Variant" or "variants" refer to variations of the nucleic acid or amino acid sequences of PAIGB molecule. Encompassed within the term "variant(s)" are nucleotide and amino acid substitutions, additions, or deletions of PAIGB molecules. Also, encompassed within the term "variant(s)" are chemically modified natural and synthetic PAIGB molecules. For example, variant may refer to polypeptides that differ from a reference polypeptide respectively. Generally, the differences between the polypeptide that differs in amino acid sequence from reference polypeptide, and the reference polypeptide are limited so that the amino acid sequences of the reference and the variant are closely similar overall and, in some regions, identical. A variant and reference polypeptide may differ in amino acid sequence by one or more substitutions, deletions, additions, fusions and truncations, that may be conservative or non-conservative, which may be present in any combination. For example, variants may be those in which several, for instance from 50 to 30, from 30 to 20, from 20 to 10, from 10 to 5, from 5 to 3, from 3 to 2, from 2 to 1 or 1 amino acids are inserted, substituted, or deleted, in any combination. Additionally, a variant may be a fragment of a polypeptide of the invention that differs from a reference polypeptide sequence by being shorter than the reference sequence, such as by a terminal or internal deletion. A variant of a polypeptide of the invention also includes a polypeptide which retains essentially the same biological function or activity as such polypeptide e.g., precursor proteins which can be activated by cleavage of the precursor portion to produce an active mature polypeptide. These variants may be allelic variations characterized by differences in the nucleotide sequences of the structural gene coding for the protein, or may involve differential splicing or post-translational modification. Variants also include a related protein having substantially the same biological activity, but obtained from a different species.

The skilled artisan can produce variants having single or multiple amino acid substitutions, deletions, additions, or replacements. These variants may include, inter alia: (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more one or more amino acids are added to the polypeptide or protein, or (iii) one in which one or more of the amino acid residues includes a substituent group, or (iv) one in which the mature polypeptide is fused with another compound, such as a compound to increase the half-life of the polypeptide (for example, polyethylene glycol), or (v) one in which the additional amino acids are fused to the mature polypeptide such as a leader or secretory sequence or a sequence which is employed for purification of the mature polypeptide or a precursor protein sequence. A variant of the polypeptide may also be a naturally occurring variant such as a naturally occurring allelic variant, or it may be a variant that is not known to occur naturally. Among polypeptide variants in this regard are variants that differ from the aforementioned polypeptides by amino acid substitutions, deletions or additions. The substitutions, deletions or additions may involve one or more amino acids. Alterations in the sequence of the amino acids may be conservative or non-conservative amino acid substitutions, deletions or additions. All such variants defined above are deemed to be within the scope of those skilled in the art from the teachings herein and from the art.

Polypeptides of the present invention includes variants of the aforementioned polypeptides, including all allelic forms and splice variants. Also encompassed by the present invention are splice variants derived from the PAIGB (SEQ ID NO: 5, or 9) nucleic acid sequences. A splice variant refers to variant PAIGB nucleic acids and polypeptides produced by differential processing of a primary transcript(s) of genomic DNA, resulting in the production of more than one type of mRNA. cDNA derived from differentially processed genomic DNA will encode PAIGB polypeptides that have regions of complete amino acid identity and regions having different amino acid sequences. Alternative RNA splicing occurs when a primary RNA transcript undergoes splicing, generally for the removal of introns, which results in the production of more than one mRNA molecule each of which may encode different amino acid sequences. Thus, the same genomic sequence can lead to the production of multiple, related mRNAs and proteins. Both the resulting mRNAs and proteins are referred to herein as "splice variants". Splice variants may be found within a single tissue type or between tissues (tissue-specific variants).

A splice variant may comprise, for example, any one of the sequences of PAIGB (SEQ ID NO: 5, 6, 9, or 10) disclosed herein. Splice variants can also comprise other combinations of introns/exons of PAIGB which can be determined by those of skill in the art. Splice variants can be determined experimentally, for example, by isolating and analyzing cellular RNAs (e.g., Southern blotting or PCR), or by screening cDNA libraries using the PAIGB-related nucleic acid probes or primers described herein. In another approach splice variants can be predicted using various methods, computer programs, or computer systems available to practitioners in the field.

The term variant may also refer to a polynucleotide whose sequence diverges from the nucleotide sequences of the present invention, e.g. SEQ ID NOs: 1, 3, 5, 7, and 9. Polynucleotide sequence divergence may result from mutational changes such as deletion, substitutions, additions of one or more nucleotides. Each of these changes may occur alone, or in combination, one or more times in a given sequence.

"Muteins" refer to PAIGB proteins or polypeptides that have minor changes in amino acid sequence caused, for example, by site-specific mutagenesis or other manipulations; by errors in transcription or translation; or which are prepared synthetically by rational design. These minor alterations result in amino acid sequences wherein the biological activity of the protein or polypeptide is altered as compared to wild-type or naturally occurring polypeptide or protein.

"PAIGB molecule" refers to PAIGB polypeptides, PAIGB peptides, fragments or variants thereof or PAIGB peptides, and nucleic acids that encode PAIGB polypeptides, PAIGB peptides, fragments or variants thereof. "PAIGB molecule" also refers to PAIGB polynucleotides, gene and variants thereof.

An "analog" of a PAIGB DNA, RNA or a polynucleotide, refers to a molecule resembling naturally occurring polynucleotides in form and/or function (e.g. in the ability to engage in sequence-specific hydrogen bonding to base pairs on a complementary polynucleotide sequence) but which differs from DNA or RNA in, for example, the possession of an unusual or non-natural base or an altered backbone. See for example, Uhlmann et al. 0 990) Chemical Reviews 90:543-584.

The term "modulate" refers to the suppression, enhancement, or induction of a function. For example, "modulation" or "regulation" of gene expression refers to a change in the activity of a gene. Modulation of expression can include, but is not limited to, gene activation and gene repression.

"Modulate" or "regulate" may also refer to methods, conditions, or agents which increase or decrease the biological activity of a protein, enzyme, inhibitor, signal transducer, receptor, transcription activator, co-factor, and the like. This change in activity can be an increase or decrease of mRNA translation, mRNA or DNA transcription, and/or mRNA or protein degradation, which may in turn correspond to an increase or decrease in biological activity. Such enhancement or inhibition may be contingent on the occurrence of a specific event, such as activation of a signal transduction pathway and/or may be manifest only in particular cell types. The modulator is intended to comprise any compound, e.g., antibody, small molecule, peptide, oligopeptide, polypeptide, or protein, preferably small molecule or peptide.

"Modulated activity" refers to any activity, condition, disease or phenotype which is modulated, e.g., by a biologically active form of a protein. Modulation may be effected by affecting the concentration of biologically active protein, e.g., by regulating expression or degradation, or by direct agonistic or antagonistic effect as, for example, through inhibition, activation, binding, or release of substrate, modification either chemically or structurally, or by direct or indirect interaction which may involve additional factors.

The terms "compound", "drug", "pharmacologically active agent", "active agent", "agent", "composition" or "medicament" are used interchangeably herein to refer to a compound or compounds or composition of matter which, when administered to a subject (human or animal) induces a desired pharmacologic and/or physiologic effect by local and/or systemic action. The agent herein may induce PAIGB molecule and may contain PTH anabolic effect.

The term "pharmaceutically acceptable carrier" encompasses any of the pharmaceutical carriers, such as phosphate buffered saline solution, water, and emulsions, such as an oil/water or water/oil emulsion, and various types of wetting agents. The composition also can include stabilizers and preservatives. For examples of carriers, stabilizers and adjuvants, see Martin, Remington's Pharm. Sci., 5th Ed. (Mack Publ. Co., Easton 0 975)).

The term "pharmaceutically acceptable salts" refers to salts prepared from pharmaceutically acceptable non-toxic acids, including inorganic salts, and organic salts. Suitable non-organic salts include but are not limited to inorganic and organic acids such as acetic, benzenesulfonic, benzoic, camphorsulfonic, citric, ethenesulfonic, fumaric, gluconic, glutamic, hydrobromic, hydrochloric, isethionic, lactic, malic, maleic, mandelic, methanesulfonic, mucic, nitric, pamoic, pantothenic, phosphoric, succinic, sulfuric, tartaric acid, p-toluenesulfonic and the like.

By "intermittent" administration, injection or treatment is meant that the compounds or compositions containing them are provided to the subject sporadically with periods between dosages or until the results are assessed. For example, there may be a one-day interval, a three-day interval, or a five-day interval between any two days on which the compounds or compositions are administered, or only a single dose is administered, or there is a period after dosage until results are assessed. That is, while on day 1 multiple dosages may occur (or only one) there may be no dosage the next day. Or if the dosage is on a daily basis, an interval may be permitted to elapse before results are assessed. The timeframe over which treatment is administered may be measured by the time between initial administration and assessment of the results. Many variations of intermittent administration will be apparent to those skilled in the art; the present invention is intended to encompass such variations.

As used herein, the term "treatment" is defined as the application or administration of an agent (e.g. therapeutic agent or a therapeutic composition) to a subject, or application or administration of an agent to a subject, or an isolated tissue or cell line from a subject, who may have a disease, a symptom of disease or a predisposition toward a disease, with the purpose to cure, heal, alleviate, relieve, alter, remedy, ameliorate, improve or affect the disease, the symptoms of disease or the predisposition toward disease. The term "therapeutic agents" refers to any molecule, compound, or treatment that assists in the treatment of a disease, e.g., a bone-related disorder. Accordingly, a therapeutic agent includes, but is not limited to, small molecules, peptides, antibodies, ribozymes and antisense oligonucleotides.

The compositions of the present invention may also include a compound in a pharmaceutically acceptable form that prevents and/or reduces the symptoms of a particular disease, such as a bone related disorder. It is contemplated that the therapeutic composition of the present invention will be provided in any suitable form. The form of the composition will depend on a number of factors, including the mode of administration. The composition may contain diluents, adjuvants and excipients, among other ingredients.

The bone strength may be determined by bone density (grs of mineral/cm$^3$ of volume) and bone quality (mineralization, bone architecture, bone turnover, micro fractures). As a measure for bone strength, Bone Mineral Density (BMD) is usually used. For example, a bone can be declared osteoporotic if its BMD is exceeds 2.5 standard deviations below the mean of BMD of young white adult women (World Health Organization, 1994, Assessment of Fracture Risk and it's Application to Screening for Postmenopausal Osteoporosis. Technical Report Series 843. Geneva: World Health Organization).

The term "PTH" refers to the parathyroid hormone and its derivatives. Parathyroid hormone to be used in the present invention may occur in various forms such as PTH of a native type, PTH produced by genetic engineering techniques, or PTH synthesized chemically. Human PTH(1-84) composed of 84 amino acid residues. Examples of PTH derivatives are partial peptides of the PTH as defined above, the constituent amino acids of the PTH of partial peptides thereof which may be partly replaced by other amino acids, the constituent amino acids of the PTH or partial peptides thereof which may be partly depleted, as well as peptides that have at least amino acid added to the PTH or partial peptides thereof; the peptides as PTH derivatives may have similar activities to the PTH itself. Examples of partial peptides of PTH include human PTH(1-34), human PTH(1-64),) human PTH(35-84) and bovine PTH(1-34). PTH(1-34) refers to a partial peptide of PTH that is composed of 34 amino acids as counted from the N terminus of PTH. hPTH refers to human PTH.

"PTH responsive gene" refers to a gene whose expression can be affected by PTH.

"Bone related disorder or disease" refer to bone formation disorder, bone resorption disorder and/or bone density disorder. Examples of bone related disorders include but are not limited to fractures and non-fracture related conditions known to those skilled in the art, which respond therapeutically to the composition described herein, degenerative bone disorder, neurodegeneration, myodegeneration, osteodegeneration, osteopenias, osteoporosis, bone cancer, arthritis, rickets, bone fracture, periodontal disease, bone segmental defects, osteolytic bone disease, primary and secondary hyperparathyroidism, Paget's disease, osteomalacia, hyperostosis, and osteopetrosis.

"Bone related agents" refer to agent which influence bone metabolism, e.g. bone forming or bone breakdown activity or both. "Bone related agents" may induce anabolic or catabolic effect, may inhibit bone resorption and result in increased BMD, or may maintain the balance between bone formation and bone resorption.

Bone forming activity can be induced by increasing osteoblastic activity, osteoblastic differentiation from osteoprogenitor cells, and increasing osteoblast profilteration, decreasing osteoblast apoptosis and any combination of thereof. In addition, "bone forming activity" refer to decreasing bone resorption or increasing new bone formation or combination of both. Bone forming activity can be induced in various bone tissues or cells.

"Bone anabolic agent" refers to an agent which induces or increases bone forming activity e.g., parathyroid hormone.

Parathyroid hormone (PTH) and it's signaling system are principal regulators of bone remodeling in the adult skeleton (Masiukiewicz and Insogna (1998) Aging 10:232-239; Mierke and Pellegrini (1999) Curr Pharm Des 5:21-36). It has a vital role in the homeostasis of calcium within the blood stream and acute in vivo effect of PTH is to increase bone resorption, although sustained increases in its circulating levels accelerate both formation and resorption. The PTH signaling pathway is also be involved in the regulation of chondrogenesis during bone formation (Vortkamp et al. (1996) Science 273:613-622; Lanske et al. (1999) J Clin Invest 104:399-407). "PTH signaling pathway" refers to any pathway in which PTH is involved such as PKC or PKA pathway. Activation of these pathways by PTH in bone cells modulates a number of biological responses that can be measured by a variety of methods that are known to those skilled in the art. Some of these activities that can be measured include but are not limited to the induction of cAMP, induction of inositol trisphosphate (IP3), induction of intracellular free $Ca^{+2}$ and modulation of gene transcription of a number of reported genes (reviewed in Swarthout, J. T., Gene 282:1-17. 2002).

"Bone tissue" refers to calcified tissues (e.g. calvariae, tibia, femur, vertebrae, teeth), bone trabeculae, the bone marrow cavity, which is the cavity other than the bone trabeculae, the cortical bone, which covers the outer peripheries of the bone trabeculae and the bone marrow cavity, and the like. Bone tissue also refers to bone cells that are generally located within a matrix of mineralized collagen; blood vessels that provide nutrition for the bone cells; bone marrow aspirates, joint fluids, bone cells that are derived from bone tissues; and may include fatty bone marrow. Bone tissue includes bone products such as whole bones, sections of whole bone, bone chips, bone powder, bone tissue biopsy, collagen preparations, or mixtures thereof. For the purposes of the present invention, the term "bone tissue" is used to encompass all of the aforementioned bone tissues and products, whether human or animal, unless stated otherwise.

The term "biological sample" is broadly defined to include any cell, tissue, biological fluids, organ, multicellular organism, and the like. A biological sample, may be derived, for example, from cells or tissue cultures in vitro. Alternatively, a biological sample may be derived from a living organism or from a population of single cell organisms. A biological sample may be a live tissue such as live bone. The term "biological sample" is also intended to include samples such as cell, tissue, biological fluids, isolated from a subject, as well as samples present within a subject. That is, the detection method of the invention can be used to detect PAIGB mRNA, protein, or genomic DNA in a biological sample in vitro as well as in vivo. For example, in vitro techniques for detection of PAIGB mRNA include Northern hybridizations and in situ hybridizations. In vitro techniques for detection of PAIGB protein include enzyme linked immunosorbent assays (ELISAs), Western blots, immunoprecipitations and immunofluorescence. In vitro techniques for detection of PAIGB genomic DNA include Southern hybridizations. Furthermore, in vivo techniques for detection of PAIGB protein include introducing into a subject a labeled anti-PAIGB antibody. For example, the antibody can be labeled with a radioactive marker whose presence and location in a subject can be detected by standard imaging techniques.

"Antibody" is meant to include but not limited to polyclonal, monoclonal, chimeric, human, humanized, bispecific, multispecific, primatizedTM antibodies. The term "antibodies" preferably refers to polyclonal and/or monoclonal antibodies and fragments thereof, and immunologic binding equivalents thereof, that can bind to the PAIGB proteins and fragments thereof or to nucleic acid sequences from the; PAIGB region or a portion thereof. The term antibody is used both to refer to a homogeneous molecular entity, or a mixture such as a serum product made up of a plurality of different molecular entities. Proteins may be prepared synthetically in a protein synthesizer and coupled to a carrier molecule and injected over several months into rabbits. Rabbit sera is tested for immunoreactivity to the PAIGB protein or fragments thereof. Monoclonal antibodies may be made by injecting mice with the proteins, or fragments thereof. Monoclonal antibodies will be screened by ELISA and tested for specific immunoreactivity with PAIGB protein or fragments thereof. Harlow et al., Antibodies: A Laboratory Manual, Cold Spring Harbor Laboratory, Cold Spring Harbor, NY (1988).

A "test sample" refers to a biological sample from a subject of interest. For example, a test sample can be a cell sample, or tissue sample. A "test sample" and "biological sample" are used interchangeably herein.

In one embodiment, the biological sample contains protein molecules from the test subject. Alternatively, the biological sample can contain mRNA molecules or genomic DNA molecules from the test subject. A biological sample may be a bone sample isolated by conventional means from a subject.

In another embodiment, the methods further involve obtaining a control biological sample from a control subject, contacting the control sample with a compound or agent capable of detecting PAIGB protein, mRNA, or genomic DNA, such that the presence of PAIGB protein, mRNA or genomic DNA is detected in the biological sample, and comparing the presence of PAIGB protein, mRNA or genomic DNA in the control sample with the presence of PAIGB protein, mRNA or genomic DNA in the test sample.

"Test compound" (used interchangeably herein with "test agent") refers to a compound, composition or extract to be tested by at least one method of the present invention for at least one activity for at least one activity such as putative modulation of a biological process or specific binding capability.

A "test compound" can be administered to a subject for the purpose of determining its effects on the subject. A test compound can be administered as a pure preparation or as a mixture with one or more other molecules. For example, a test compound can be combined with, or dissolved in, an agent that facilitates uptake of the compound by the subject, such as an organic solvent, for example, DMSO or ethanol; or an aqueous solvent, for example, water or a buffered aqueous solution; or food.

A "test compound" also refers to a compound or a collection of compounds that are to be screened for their ability to affect a particular biochemical system. Test compounds may include a wide variety of different compounds, including chemical compounds, mixtures of chemical compounds, e.g., polysaccharides, small organic or inorganic molecules or any combinations thereof; biological macromolecules, e.g., peptides, proteins, nucleic acids such as DNA, RNA or combinations thereof, antisense molecules or ribozymes; or an extract made from biological materials such as bacteria, plants, fungi, or animal cells or tissues, naturally occurring or synthetic compositions, antibodies or fragments or active fragments thereof. Test compounds that include nucleic acid molecules can be provided in a vector, such as a viral vector, such as a retrovirus, adenovirus or adeno-associated virus, a liposome, a plasmid or with a lipofection agent. Test compounds, once identified, can be agonists, antagonists, partial agonists or inverse agonists of a target. Depending upon the particular embodiment being practiced the test compounds are provided, e.g., injected, free in solution, or are optionally attached to a carrier, or a solid support, e.g., beads. A number of suitable solid supports are employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, glass beads, polyaminemethylvinylether maleic acid copolymer, amino acid copolymer, ethylene-maleic acid copolymer, nylon, silk, etc. Additionally, for the methods described herein, test compounds can screened individually, or in groups.

The present invention further relates to the kits for detecting the presence of PAIGB molecule in a biological sample. For example, the kit can comprise a labeled compound or agent capable of detecting PAIGB polypeptide or mRNA in a biological sample; means for determining the amount of PAIGB in the sample; and means for comparing the amount of PAIGB in the sample with a standard. The compound or agent can be packaged in a suitable container. The kit can further comprise instructions for using the kit to detect PAIGB polypeptide or nucleic acid.

The present invention also relates to the vectors that include nucleic acid molecules of the present invention, host cells that genetically engineered with vectors of the present invention such as cloning vector or expression vector and to the production of polypeptides of the present invention by recombinant techniques.

Nucleic Acid Molecules:

The nucleic acid fragments of the present invention may be used to isolate cDNAs or genes from the same or other species. Isolation of homologous genes using sequence dependent protocols is well known in the art and include but are not limited to methods of nucleic acid hybridization, and methods of DNA and RNA amplifications such as polymerase chain reaction or ligase chain reaction. In particular, the polynucleotides of the present invention may be used to identify genes that are regulated during bone differentiation. For example, PAIGB may be down regulated by known methods in the art (e.g. by introducing antisence RNA or RNAi technologies) and the effect of this down regulation on differentiation related genes would indicate the position of the gene in PTH induction of bone synthesis or PTH signaling pathway.

In general, a sequence of ten or more contiguous amino acids or thirty or more nucleotides may be used in order to putatively identify a polypeptide or nucleic acid sequence as homologous to a known protein or gene. For example, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers.

Furthermore, genes encoding similar polypeptides to that of the present invention, either as cDNA or genomic DNAs, could be isolated directly by using all or a portion of the present nucleic acid fragments as DNA hybridization probes to screen libraries from any desired sources such as bacteria, mammalian cell, λ phage using methodology well-known to those skilled in the art (Sambrook, J., Fritsch, E. F. and Maniatis, T., Molecular. Cloning: A Laboratory Manual (1989), Cold Spring Harbor Laboratory Press, Cold Spring Harbor (referred to throughout as "Maniatis")). Moreover, the entire sequences can be used directly to synthesize DNA probes by methods known to the skilled artisan such as random primers DNA labeling, or end-labeling techniques, nick translation, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full-length cDNA or genomic fragments under conditions of appropriate stringency.

Two short segments of the instant nucleotide sequences may be used in polymerase chain reaction protocols to amplify longer nucleic acid fragments encoding homologous genes from DNA or RNA. Alternatively, the second primer sequence may be based upon sequences derived from the cloning vector. For example, the skilled artisan can follow the RACE protocol to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., PNAS USA (1989) 86:5673; Loh et al., Science (1989) 243:217).

In PCR-type amplification techniques, the primers have different sequences and are not complementary to each other. Depending on the desired test conditions, the sequences of the primers may be designed to provide for both efficient and faithful replication of the target nucleic acid. Methods of PCR primer design are common and well-known in the art. (Thein and Wallace, "The use of oligonucleotide as specific hybridization probes in the diagnosis of 12 genetic disorders" (1986) pp. 33-50,—in Human Genetic Diseases: A Practical Approach, K. E. Davis (Ed.). ML Press, Herndon, Va.); Rychlik, W., PCR Protocols: Current Methods and Applications. (1993) 15:31-39.) Alternatively, the instant sequences may be used as hybridization reagents for the identification of homologs. The basic components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected (cDNA, genomic DNA or RNA). The probe length can vary from 5 bases to tens of thousands of bases, the length depending upon the specific test to be done. Only portion of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

A "polymerase chain reaction" ("PCR") is a reaction in which replicate copies are made of a target polynucleotide using one or more primers, and a catalyst of polymerization, such as a reverse transcriptase or a DNA polymerase, and particularly a thermally stable polymerase enzyme.

Generally, a PCR may involve reiteratively forming three steps: "annealing", in which the temperature is adjusted such that oligonucleotide primers are permitted to form a duplex with the polynucleotide to be amplified; "elongating", in which the temperature is adjusted such that oligonucleotides that have formed a duplex are elongated with a DNA polymerase, using the polynucleotide to which they have formed the duplex as a template; and "melting", in which the temperature is adjusted such that the polynucleotide and elongated oligonucleotides dissociate. The cycle is then repeated until the desired amount of amplified polynucleotide is obtained. Methods for PCR are taught in U.S. Pat. No. 4,683,195 to Mullis and U.S. Pat. No. 4,683,202 to Mullis et al. Elements within a gene include but are not limited to promoter regions, enhancer regions, repressor binding regions, transcription initiation sites, ribosome binding sites, translation initiation sites, protein encoding regions, introns and exons, and termination sites for transcription and translation.

Hybridization methods are well known in the art (Maniatis, particularly Chapter 11 and Table 11.1). Typically, the probe and sample are mixed under conditions which will permit nucleic acid hybridization. This involves contacting the probe and sample in the presence of an inorganic or organic salt under appropriate temperature and ionic strength conditions. The probe and sample nucleic acids will be in contact for a long enough time that any possible hybridization between the probe and sample nucleic acid may occur. The concentration of probe or target in the mixture will determine the time necessary for hybridization to occur. The greater the probe or target concentration, the shorter the hybridization incubation time needed. Optionally, a chaotropic agent maybe added. The chaotropic agent stabilizes nucleic acids by inhibiting nuclease activity. Furthermore, the chaotropic agent allows sensitive and stringent hybridization of short oligonucleotide probes at room temperature (Van Ness et al., Nucl. Acids Res. (1991) 1,9:5143-5151). Suitable chaotropic agents include guanidinium, chloride, guamidiniurn thiocyanate, sodium thiocyanate, lithium tetrachloroacetate, sodium perchlorate, rubidium, tetrachloroacetate, potassium iodide, and cesiurri trifluoroacetate, and the like. Typically, the chaotropic agent will be present at a final concentration of about 3M. If desired, one can add formamide to the hybridization mixture, typically 30-50% (v/v).

Various hybridization solutions may be used. Typically, these comprise from about 20 to 60% volume i.e, preferably 30%, of a polar organic solvent. A common hybridization solution employs about 30-50% v/v formamide, about 0.15 to 1 M sodium chloride, about 0.05 to 0.1 M buffers, such as sodium citrate, Tris-HCl, PIPES or HEPES (pH range about 6-9), about 0.05 to 0.2% detergent, such as sodium dodecylsulfate, or between 0.5-20 mM EDTA, FICOLL (Pharmacia Inc.) (about 300-500 kilodaltons), polyvinylpyrrolidone (about 250-500 kilodaltons), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic saccharidic polymers, such as dextran sulfate and anionic polymers such as polyacrylate or polymethylacrylate.

Nucleic acid hybridization may be adapted to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

The present invention particularly contemplates nucleic acid sequences that hybridize under stringent conditions to the PAIGB coding sequences described herein and complementary sequences thereof. For the purposes of this invention, the term "stringent conditions" means hybridization will occur only if there is at least 80% and preferably at least 85% and most preferably at least 90% identity between the nucleic acid sequences. Accordingly, the present invention also includes isolated nucleic fragments that are complementary to the complete sequences as reported in the accompanying Sequence Listing as well as those that are at least 90% identical to such sequences, and polynucleotides having sequences that are complementary to the aforementioned polynucleotides. The polynucleotides of the present invention that hybridize to the complement of PAIGB coding sequences described herein preferably encode polypeptides that retain substantially the same biological function or activity as the PAIGB polypeptide encoded by the cDNA of SEQ ID NO:1, 3, 5, 7 and 9.

It may also be desirable to reduce or eliminate expression of genes encoding the polypeptide of the present invention for some applications. In order to accomplish this, a chimeric gene or a chimeric construct designed for co-suppression of the instant polypeptide can be constructed by linking a gene or gene fragment encoding that polypeptide to a promoter sequences. Alternatively, a chimeric gene or chimeric construct designed to express antisense RNA for all or part of the instant nucleic acid fragment can be constructed by linking the gene or gene fragment in reverse orientation to a promoter sequences. Either the co-suppression or antisense chimeric genes could be introduced into desired host cell via transformation wherein expression of the corresponding endogenous genes are reduced or eliminated.

The polynucleotide of the present invention, may be in the form of RNA or in the form of DNA, which DNA includes cDNA and synthetic DNA. The DNA may be single stranded or double stranded. If it is single stranded, it may be the coding strand or non-coding (antisense) strand. The coding sequence may be identical to the coding sequence of SEQ ID NOs:1, 3, 5, 7, 9 or may be a different coding sequence which the coding sequence, as a result of degeneracy or redundancy of the genetic code, encodes for the same polypeptide.

The present invention also includes variants of the hereinabove described polynucleotides which encode fragments, analogs, and derivatives of the polynucleotides characterized by the deduced amino acid sequence of SEQ ID NO:5, and 9. The variant of the polynucleotide may be a naturally occurring allelic variant of the polynucleotide or a non-naturally occurring variant of the polynucleotide.

The polynucleotide of the present invention, may have a coding sequence which is a naturally occurring allelic variant of the coding sequence characterized by the DNA sequence of the SEQ ID NO:1 and 9. An Allelic variant is an alternate form of a polynucleotide sequence which which may have a substitution, deletion, or addition of one or more nucleotides, which does not substantially alter the function of the encoded polypeptide.

The polynucleotide which encodes for the mature polypeptide, i.e. PAIGB protein, may include only the coding sequence for the mature polypeptide or the coding sequence for the mature polypeptide and additional sequence such as gene control sequence, regulatory or secretory sequence.

The present invention therefore includes polynucleotides wherein the coding sequence for the mature polypeptide may be operatively linked in the same reading frame to a polynucleotide sequence which aids in expression and secretion of a polypeptide from a host cell. The polynucleotide may also encode for a precursor protein.

Polynucleotides which encode polypeptides include those containing predetermined mutations by, e.g., homologous recombination, site-directed or PCR mutagenesis, and recombinant PAIGB proteins or polypeptide fragments of other animal species, including but not limited to vertebrates (e.g., rabbit, rat, murine, porcine, camelid, reptilian, caprine, avian, fish, bovine, ovine, equine and non-human primate species) as well as invertebrates, and alleles or other naturally occurring variants and homologs of PAIGB of the foregoing species and of human sequences.

The polynucleotide of the present invention may have the coding sequence fused in frame to a marker sequence, such as hexa-histidine tag (Qiagen Inc.), at either 3' or 5' terminus of the gene to allow purification of the polypeptide of the present invention.

Host Cells:

Host cells can be engineered with the vectors of the present invention. The host organism (recombinant host cell) may be any eukaryotic or prokaryotic cell, or multicellular organism. They may be derived from mammals, yeast, fungi, or viruses. Suitable host cells may include but are not limited to mammalian cells (e.g. monkey kidney (COS-7), human kidney (293), hamster ovary (CHO), human liver (HepG2), human cervical (HeLa), mouse fibroblast (NIH3T3), mouse fibroblast (MG-63)), mammalian osteoblasts (e.g. Primary osteoblasts, human osteoblast cell (e.g. TE-85, U2OS and SAOS-2), rat osteoblast cells (e.g. UMR 106, ROS 17/2.8), mouse osteoblast cells (e.g. MC3T3), and mesenchymal stem cells. Furthermore, various strains of *E. coli* (e.g., DH5alpha, BL21, DH10B), yeast cells (e.g. *Schizasaccharomyces, Saccharomyces Cerevisice, Pichia Pastoris, Pichia Methanolica*) and insect cells SF9 or SF21—*Spodoptera Frugiperda*, S2 Schneider Cells, High Five Cells from *Trichoplusia ni* egg) may be used as host cells for molecular biological manipulation.

The vectors may be cloning vectors or expression vectors such as in the form of a plasmid, a cosmid, or a phage or any other vector that is replicable and viable in the host cell. The engineered host cells can be cultured in conventional nutrient media modified as appropriate for activating promoters, selecting transformants or amplifying the polynucletide of the present invention. The culture conditions such as pH, temprature, and the like, are those suitable for use with the host cell selected for expression of the polynucleotide are known to the ordinarily skilled in the art.

Plasmids generally are designated herein by a lower case "p" preceded and/or followed by capital letters and/or numbers, in accordance with standard naming conventions that are familiar to those of skill in the art. The plasmids herein are either commercially available, publicly available on unrestricted bases, or can be constructed from available plasmids by routine application of well-known, published procedures. Additionally, many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

The appropriate DNA sequence may be inserted into the vector by a variety of the procedures known in the art.

The DNA sequence in the expression vector may be operatively linked to an appropriate expression control element(s) to direct mRNA synthesis. The expression control elements are known in the art and include, but are not limited to, inducible promoters, constitutive promoters, secretion signals, and other regulatory elements. Preferably, the inducible promoter is readily controlled, such as being responsive to a nutrient in the host cell's medium. Examples of promoters are SV40, human cytomegalovirus (CMV) promoters (e.g. pcDNA 3.1 vector or any form of the pcDNA series), SP6, T7, and T3 RNA polymarase promoters. The gene may be placed under the control of a promoter, ribosome binding site (for bacterial expression), suitable gene control sequence, or regulatory sequences so that the DNA sequence encoding the protein is transcribed into RNA in the host cell transformed by a vector containing this expression construct. Such promoters include but are not limited to SV40, human cytomegalovirus (CMV) promoters (e.g. pcDNA 3.1 vector or any form of the pcDNA series), SP6, T7, and T3 RNA polymerase promoters. In some cases it may be desirable to add sequences, which cause the secretion of the polypeptide from the host cell, with subsequent cleavage of the secretory signal.

The expression vector may also include a ribosome binding site for translation initiation, a transcription terminator, and an appropriate sequences for amplifying the expression. The expression vector may also include one or more selectable marker genes to provide a specific phenotype for the selection of transformed host cells such as neomycin resistance for eukaryotic cells or ampicillin resistance for E. coli.

Vectors and promoters suitable for use in yeast expression are described in EP 73,675A. Examples of vectors include but not are limited to pCMV SPORT6, pCDNA3.1DN5-His-TOPO, and pCDNA3.1/CT-GFP-TOPO. Appropriate non-native mammalian promoters might include the early and late promoters from SV40 (Fiers et al, Nature, 273:113 (1978)) or promoters derived from Moloney murine leukemia virus, mouse tumor virus, avian sarcoma viruses, adenovirus II, bovine papilloma virus or polyoma. In addition, the construct may be joined to an amplifiable gene (e.g., DHFR) so that multiple copies of the gene may be made. For appropriate enhancer and other expression control sequences, see also *Enhancers and Eukaryotic Gene Expression* (Cold Spring Harbor Press, Cold Spring Harbor, N.Y., 1983). Preferred bone related promoters include CMVbAc-tin or type I collagen promoters to drive expression of the human HBM, Zmax1 or LRP6 cDNA. Other preferred promoters for mammalian expression are from cytomegalovirus (CMV), Rous sarcoma virus (RSV), Simian virus 40 (SV40), and EF-1a (human elongation factor 1a-subunit).

In addition, PAIGB may be over-expressed under viral promoter in different cell lines to identify its role in various cell functions. For example, PAIGB can be over-expressed in osteoblastic cell lines and its role in calcification may then be monitored by the standard techniques.

Furthermore, genes that are regulated during bone differentiation may be monitored when PAIGB is over-expressed. In addition the effects of PAIGB down regulation (by introducing anti-sense RNA or RNAi technologies) on differentiation related genes might indicate the position of this protein in PTH induction of bone synthesis.

Production of Recombinant Peptides or Polypeptides Using a cDNA or Other Recombinant Nucleic Acids:

The present invention further relates to a method of production of the polypeptides of the present invention. The polypeptide of the present invention may be produced by growing suitable host cells transformed by expression vector described above under conditions whereby the polypeptide of the interest is expressed. The polypeptide may then be isolated and purified. Methods of the purification of proteins from cell cultures are known in the art and include but not limited to ammonium sulfate precipitation, anion or cation exchange chromatography, and affinity chromatography.

The polypeptide of the present invention may be synthesized by peptide synthesizers. In addition, cell-free translation systems may be employed to produce the polypeptides of the present invention using the RNAs derived from the nucleic acid molecules of the present invention.

The polypeptide of the present invention include the full length PAIGB protein and polypeptide fragments thereof. These proteins may be mammalian proteins and or human proteins. Alternative embodiments include polypeptide fragments having a consecutive amino acid sequence of at least about 3, 5, 7, 8, 9, 10, 15, 20, 25, 30, 40, 50, 60, 70, 80, 90, 100 amino acid residues from a common polypeptide sequence; amino acid sequence variants of a common polypeptide sequence wherein an amino acid residue has been inserted N- or C-terminal to, or within, the polypeptide sequence or its fragments; and amino acid sequence variants of the common polypeptide sequence or its fragments, which have been substituted by another conserved residue.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences added and/or with targeting sequences that are already present removed. While the references cited give examples of each of these, the list is not exhaustive and more targeting signals of utility may be discovered in the future.

Protein Expression Detection:

For protein expression detection, antibodies that are specific for the PAIGB polypeptides or fragments thereof may be used, for example, in flow cytometric analysis, immunohistochemical staining or immunofluorescence microscopy. Screening for the expression of the fragments, mutants or variants of PAIGB polypeptide can be accomplished using one or more of several different assays. For example, appropriate cells, such as human osteoblast cells, can be introcuded into cells by methods known in the art, e.g. cDNA transfection, viral infection using the the cloned variants. The cells can be analyzed for cell surface PAIGB expression using by direct or indirect immunofluorescence and flow cytometry. Cell surface expression of the transfected cells may be evaluated using a monoclonal antibody specificall reactive with a PAIGB polypeptide. It will be understood that cDNA, synthetically produced DNA or chromosomal DNA may also be employed to transiently transfect the cell by utilizing methods and protocols known and practiced by those having skill in the art. For example, the protein levels of PAIGB from cell lysates can be quantitated by conventional ELISA and RIA based assays using antibodies to PAIGB. Various methods for ELISA or RIA assays are readily available and known in the art.

Antibody and Antibody Fragments:

Availability of the present nucleotide and deduced amino acid sequences facilitates immunological screening of cDNA expression libraries. The polypeptides of the present invention or cells expressing them may be used as immunogen to prepare antibodies by methods known to those skilled in the art. The foregoing antibodies can be used in methods known in the art relating to the localization and activity of the PAIGB, e.g., for Western blotting, imaging PAIGB in situ, measuring levels thereof in appropriate physiological or biological samples, etc. using any of the detection techniques mentioned above or known in the art. In one embodiment, antibodies that are both specific for the PAIGB protein and interfere with its activity may be used to modulate or inhibit PAIGB protein function. Such antibodies may be generated using standard techniques described herein, against the PAIGB protein itself or against peptides corresponding to portions of the protein. Such antibodies include but are not limited to polyclonal, monoclonal, Fab fragments, single chain antibodies, or chimeric antibodies.

In another embodiment, the antibodies of the present invention can be used in flow cytometry studies, in immunohistochemical staining, and in immunoprecipitation which serve to aid the determination of the level of expression of an PAIGB in a normal cell or tissue or, cell or tissue from a subject suffering from or susceptible to bone disease. For example, synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, Adv. ImmunoL 36:1 (1984); and Maniatis).

Furthermore, the polypeptides of SEQ ID NOs: 2, 4, 6, 8, 10 or any portion of SEQ ID NOs: 2, 4, 6, 8, 10 and/or encoded by SEQ ID NOs:1, 3, 5, 7, 9 or cells expressing any of the aforementioned polypeptides may be used as immunogens. These antibodies can be polyclonal or monoclonal and may include chimeric, single chain, and Fab fragments or the products of the Fab expression library. The antibodies are useful for detecting the polypeptide of the present invention in situ in cells or in vitro in cell extracts.

Accordingly, PAIGB polypeptide is expressed and rabbit polyclonal antibodies are produced. More particularly, RADAIEPRYYESWTRE (SEQ ID NO:11) EDGLPSNGVPRS (SEQ ID NO:12), EAKRDAKRMPAKE (SEQ ID NO:13) and QMDRSRRITKNCVN (SEQ ID NO:14) sequences are synthesized and used to immunize the animals. The produced antibodies are a useful tool to analyze expression of PAIGB at protein level. The results of such analysis serve as a valuable marker to rapidly monitor the potential effectiveness of a bone anabolic agent prior to observing changes in BMD.

Screening, Diagnostics and Therapeutics:

Various uses of the PAIGB of the present invention include but are not limited to therapeutic modulation of pathophysiologic PTH signaling pathway (e.g. gene delivery approaches, gene silencing approaches, protein therapeutics antibody therapeutics), diagnostic utility, pharmaceutical drug targets, identification of agonists or antagonists, and study of the molecular mechanisms of PTH action.

For example, the polypeptides of the present invention can be used as targets to facilitate design and/or identification of compounds that may be useful as drugs in treating existing osteoporosis or in prevention therapy to reduce risk of fracture and osteoporosis development in pre-menopausal women.

These compounds may be used in treatment of osteoporosis of women in menopause to prevent further deterioration of bone by inducing bone formation. It may be given as a mono-therapy and/or in combination with already existing therapies that inhibits bone loss or as an additional therapy to estrogen.

These compounds may be used to treat bone related disorders resulting from alterations in signaling pathway involved in regulation of PAIGB expression by PTH. For example, the compound(s) that acts on PAIGB altering its function in a mode to support bone formation may be used as a prevention therapy in both men and women to increase the strength of their bone and lower the risk of bone fracture. The compound may also mimic PAIGB function and increase bone forming activity.

In addition, the polynucleotides and polypeptides of the present invention may be used to identify additional targets (e.g. interacting proteins) that may influence signaling pathway involved in regulation of PAIGB expression by PTH. More particularly, the polynucleotides and polypeptides of the present invention can represent a target for developing new compounds that would mimic the anabolic effects of PTH. Such a compound would represent a novel therapeutic agent where effects of continuous exposure to PTH would not be a question since the activity of the developed compound would be specific to PTH's anabolic activity. Such a compound would be an agent or compound as defined supra herein above.

In one embodiment, a polynucleotide probe capable hybridizing with the polynucleotide having the nucleic acid sequence forth in SEQ ID NO: 1, 3, 5, 7 and 9 can be used as in diagnostic process detecting a PAIGB polynucleotide in a sample derived from a mammalian host cell comprising detecting the presence or absence of the PAIGB in the sample.

Furthermore, large-scale production of cloned PAIGB would enable the screening of large numbers of PAIGB analogs, and would facilitate the development of new or improved agonists and/or antagonist compounds in the clinical therapy of metabolic bone disorders. More specifically, the screening of large numbers of analogs for PAIGB activity could lead to development of improved drugs for use in clinical therapy of osteoporosis or other bone related disorders.

All of the compounds of the invention may be in the form of the pharmaceutically acceptable salts or esters. Salts may be, for example, $Na^+$, $K^+$, $Ca^{+2}$, $Mg^{+2}$ and the like; the esters are generally those of alcohols of 1-6 carbons.

PAIGB Promoter to Screen for Activation:

Identification and isolation of the transcription regulatory elements (promoter) responsible for the tissue specific regulation of PAIGB provides a tool for screening agents (e.g., drugs, compounds, peptides) which promote the expression of PAIGB. The regulation of the promoter may be achieved by modulating the expression and/or activity of factors (coactivators or corepressors) that do not directly bind to the response element but which influences transcriptional activity (Trans-acting factor). Transcriptional activity may also be regulated by modulation the expression and/or activity of factors that directly bind to the DNA regulatory response elements (Cis acting factors). A high through-put screen can involve testing agents for their ability to activate the tissue specific regulatory elements within the PAIGB promoter. Such an agent induces the transcriptional levels of PAIGB and is useful for the treatment of osteoporosis. In order to utilize the tissue specific PAIGB DNA regulatory elements to screen agents, the promoter elements are isolated and cloned into reporter plasmids (luciferase, β-galactasidase, chloramphenicol transferase, etc.) using techniques and plasmids that are known in the art. DNA regulatory elements which confers full transcriptional activity selectively in osteoblastic cells would be identified by transiently expressing the DNA reporter constructs containing the regulatory elements in osteoblastic and non-osteoblastic cells. Transcritional activity is measured in osteoblastic cells treated with known osteoblast differentiation agents or agents which promote osteoblast activity. These agents include but are not limited to PTH, dexamethasone, prostaglandin $E_2$, vitamin $D_3$ and bone morphogenic protein 2 (BMP-2). Having the PAIGB bone specific promoter isolated and introduced into osteoblastic cells (transiently, stablely, virally) by methods known in the art. Any agent may be screened for their ability to activate this PAIGB promoter driven reporter.

Gene Inducible System:

A further application of the nucleic acids, vectors and regulatory regions according to the invention described hereinabove is their use as chemically inducible expression systems (gene inducible system or controlled expression of target genes) for a variety of target genes. To this end, the nucleic acids can be expressed in host cells as described above. The target genes are cloned into expression vectors, which are provided with a suitable promoter with regulatory regions. These expression vectors are then also introduced into the host cells. An inducible stable cell line (gene inducible system) could be used: 1) to evaluate the effects of PAIGB overexpression on osteoblast function (regarding expression of osteoblast specific genes), cell proliferation and apoptosis, 2) to screen for agents that interact with PAIGB and thereby modulate its activity, 3) as a secondary screen to demonstrate that the activity of a small molecule is dependent on the expression of PAIGB, 4) to evaluate the influence of other bone related hormones/factors (estrogen, PGE2, BMP's, PTH, dexamethasone, vitamin D3 etc.) on osteoblast function when PAIGB is highly expressed, 5) as a source of PAIGB protein, 6) to identify proteins that interact with PAIGB, 7) as a transient transfections for biological validation, 8) to express different forms of PAIGB, and 8) in gene transfer (Abruzzese R V et al. Human Gene Therapy. 1999;10:1499-1507; Abruzzese R A et al. Molecular Therapy. 2000;2:276-287).

In particular, PAIGB can be used in gene inducible system in a transient transfection assays to determine whether bone related agents have effects on bone metabolism that are dependent on PAIGB molecule expression, or effect PTH signaling pathway.

PAIGB polynucleotides can be used in a gene inducible system to create transgenic animals. Stable cell lines can further be established from tissues of such transgenic animals.

A gene inducible system of the present invention can be used for development of animal models where Cre recombinase expression can be made MFP-dependent in bone tissue (e.g. type I collagen, osteocalcin promoters) for temporally regulated bone-specific deletion of floxed genes (Andras Nagy, Genesis 26:99-109, 2000).

A gene inducible system can be a molecular tool which allows for low to undetectable basal expression of a target gene when the system is not activated and increased expression levels of the target gene when the system is activated reviewed in Clackson T. Curr Opin Chem Biol. 1997;1:210-218; Lewandoski M. Nat Rev Genet. 2001; 2:743-755). Accordingly, the components comprise an effector (regulator protein) that can be activated by a ligand and a target gene (PAIGB gene) that binds the effector. The mifepristone-inducible system is based on a truncated human progesterone receptor (PR) ligand binding domain (LBD) which has lost the ability to be activated by progesterone but has gained the ability to be activated by antiprogestins such as Mifepristone (MFP). When the truncated ligand binding domain of the progesterone receptor is joined to DNA binding (e.g. yeast GAL4) and activation domains (e.g. VP16; the p65 subunit of human NFKB), a ligand-specific transcription factor (regulator protein) is produced that specifically induces transcription of genes linked to promoters with cognate GAL4 DNA binding sites (Wang Y et al. Proc. Natl. Acad. Sci. USA. 1994;91:8180-8184; Delort J et al. Human Gene Therapy. 1996;7:809-820).

The antiprogestin-regulated system is an example of a gene inducible system that can utilize constitutive promoters (e.g. CMV, TK) for ubiquitous expression of the effector or tissue-specific promoters to drive expression of the effector in a preferred tissue (e.g. bone tissues and cells). In the presence of ligand, the effector dimerizes and binds to its cognate DNA binding sequences in the target gene (PAIGB gene) that contains a minimal E1b TATA promoter and several copies of the GAL4 DNA binding element. When such binding of the effector occurs, transcription of the PAIGB gene is increased leading to an increase in PAIGB expression Trangenic animals can be created using gene inducible technology known in the art (Wang Y., et al, *Nature Biotechnol.* 1997;15:239-243).

Knock-out animals can be created using gene inducible system as described in the art (Kellendonk C. et al. *J. Mol. Biol.* 1999; 285:175-182, Minamino et al., Circ. Res. 2001, 88: 587-592).

Pharmaceutical Compositions:

This invention also provides compositions containing any of the above-mentioned proteins, muteins, fragments, antibodies, nucleic acid molecules encoding such proteins, muteins, antibodies or fragments thereof, as well as vectors and host cells that express such nucleic acid molecules, and an acceptable solid or liquid, carrier buffer, or diluent.

The compositions of the present invention can be administered to an individual in need of facilitated neural, muscle cartilage and bone growth by numerous routes, including but not limited to intravenous, subcutaneous, intramuscular, intrathecal, intracranial and topical. The composition may be administered directly to an organ or to organ cells by in vivo or ex vivo methods.

These compositions may be in soluble or microparticular form, or may be incorporated into microspheres or microvesicles, including micelles and liposomes.

Pharmaceutical compositions of the invention may comprise one or more additional active components and, preferably, include a pharmaceutically acceptable carrier. The additional active component may be provided to work in combination with an active based on a one or more PAIGBs, as described above. In alternative embodiments, the additional active is added since it works on the same disease or disorder as PAIGBs but by a different mode of action from those actives based on PAIGBs, or the additional active may work on other diseases or disorders present in a human or animal.

Active compounds for use in the methods of the invention can be incorporated into pharmaceutical compositions suitable for administration. As used herein, the language "active compounds" includes PAIGB nucleic acid molecules, PAIGB proteins or fragments thereof, and anti-PAIGB antibodies, as well as identified compounds that modulate PAIGB gene expression, synthesis, and/or activity. Such compositions typically comprise the compound, nucleic acid molecule, protein, antibody as well as vectors and host cells that express such nucleic acid molecules, and a pharmaceutically acceptable carrier. The compositions of the present invention may contain one or more other active compounds in combination with one or more bone related agents. For example, an agent that induces PAIGB molecule may be combined with estrogen, bisphosphonates, tissue selective estrogens.

An effective amount of one or more active ingredient is used which is sufficient to accomplish the desired regulatory effect on a bone-forming activity or apoptosis activity. An effective amount can be determined by conventional dose-response curves for the desired activity. When the compositions are used pharmaceutically, they are combined with a "pharmaceutically acceptable carrier" for diagnostic and therapeutic use. The formulation of such compositions is well known to persons skilled in this field. Pharmaceutical compositions of the invention may comprise one or more additional active components and, preferably, include a pharmaceutically acceptable carrier.

Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The term "pharmaceutically acceptable carrier" refers to a carrier that does not cause an allergic reaction or other untoward effect in patients to whom it is administered. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of one or more of the active components of the composition. The use of such media and agents for pharmaceutically active substances is well known in the art. Except insofar as any conventional media or agent is incompatible with the active ingredient, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral, inhalation, buccal, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL®) (BASF, Parsippany, N.J.) or phosphate buffered saline (PBS). The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

In certain embodiments, antibodies that binds all or a portion of an PAIGB protein are employed in the composition to treat of any of the bone related diseases or disorders. Polyclonal and monclonal antibodies can be prepared by conventional methods. Generally, an antibody is raised against an amino acid sequence (a) that is specific to a PAIGB protein (or proteins) and (b) that is also more likely to be antigenic. One can select a sequence specific for a PAIGB polypeptide by performing sequence analysis and using any conventional programs for sequence alignment and sequence comparisons. An amino acid sequence that is hydrophilic at one or more ends, preferably at both ends, is generally preferred for raising antibodies. In addition to employing amino acids that are hydrophilic, in preferred embodiments the hydrophilic amino acids are also basic (non-acidic). One can also employ any amino acid that increases antigenicity. For example, often prolines are employed in the center portion of the sequence. Antigenicity can be measured by an increase in decrease in the amount of antibody that is produced when generating antibodies against an initial test sequence, which is specific a PAIGB protein(s). In certain embodiments of the present invention, the antibody is raised against a sequence comprising at least 8 consecutive amino acids of an PAIGB protein(s), and preferably a sequence comprising at least 10 consecutive amino acids of an PAIGB protein(s). In further preferred embodiments, the antibody is raised against amino acid sequence comprising about 15 to about 30 amino acids.

Use of PAIGB Molecules for Evaluating the Efficacy of Drugs

The present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (a) obtaining a pre-administration sample from a subject prior to administration of the agent; (b) detecting the level of expression of a PAIGB protein, mRNA, or genomic DNA in the pre-administration sample; (c) obtaining one or more post-administration samples from the subject; (d) detecting the level of expression or activity of the PAIGB protein, mRNA, or genomic DNA in the post-administration samples; (e) comparing the level of expression or activity of the PAIGB protein, mRNA, or genomic DNA in the pre-administration sample with the PAIGB protein, mRNA, or genomic DNA in the post administration sample or samples; and (f) altering the administration of the agent to the subject accordingly. For example, increased administration of the agent may be desirable to increase the expression or activity of PAIGB to raise levels than the mRNA expression that was detected before increased administration of the agent, i.e., to increase the effectiveness of the agent. According to such an embodiment, PAIGB expression or activity may be used as an indicator of the effectiveness of an agent, even in the absence of an observable phenotypic response.

The present invention further provides methods for evaluating the efficacy of drugs and monitoring the progress of patients involved in clinical trials for the treatment of bone related disorders. Monitoring the influence of agents (e.g., drugs) on the expression or activity of a PAIGB protein (e.g., the modulation of cell proliferation and/or migration) can be applied not only in basic drug screening, but also in clinical trials. For example, the effectiveness of an agent determined by a screening assay as described herein to increase PAIGB gene expression, or protein levels, can be monitored in clinical trials of subjects exhibiting increased PAIGB gene expression, or protein expression levels. Alternatively, the effectiveness of an agent determined by a screening assay to increase PAIGB gene expression, or protein expression levels can be monitored in clinical trials of subjects exhibiting increased PAIGB gene expression, or protein expression levels. In such clinical trials, the expression or activity of a PAIGB gene, and other genes that have been implicated in, for example, a PAIGB associated disorder can be used as a "read out" or markers of the phenotype a particular cell, e.g., a bone. In addition, the expression of a PAIGB gene, or the level of PAIGB protein expression may be used as a read out of a particular drug or agent's effect on a bone associated disease state.

For example, and not by way of limitation, genes, including PAIGB that are modulated in cells by treatment with an agent (e.g., compound, drug or small molecule) which modulates PAIGB expression or activity (e.g., identified in a screening assay as described herein) can be identified. Thus, to study the effect of agents on PAIGB associated disorders (e.g., bone associated), cells can be isolated and RNA prepared and analyzed for the levels of expression of PAIGB and other genes implicated in the PAIGB associated disorder, respectively. The levels of gene expression (e.g., a gene expression pattern) can be quantified by northern blot analysis or real-time quantitative RT-PCR, as known in the art, or alternatively by measuring the amount of protein produced, by one of the methods as known in the art, or by measuring the levels of activity of PAIGB or other genes. In this way, the gene expression pattern can serve as a marker, indicative of the physiological response of the cells to the agent. Accordingly, this response state may be determined before, and at various points during treatment of the individual with the agent.

Use of PAIGB Molecules as Biochemical Marker:

The PAIGB molecules of the invention are also useful as markers of bone related disorders or disease states, as markers for precursors of disease states, as markers for predisposition of disease states, as markers of drug activity, or as markers of the pharmacogenomic profile of a subject. Using the methods described herein, the presence, absence and/or quantity of the PAIGB molecules of the invention may be detected, and may be correlated with one or more biological states in vivo. For example, the PAIGB molecules of the invention may serve as biochemical markers for one or more bone disorders or disease states or for conditions leading up to disease states. As used herein, biochemical marker correlates with the absence or presence of a disease or disorder, or with the progression of a disease or disorder (e.g., with the decreased BMD). Therefore, these markers may serve to indicate whether a particular course of treatment is effective in lessening a disease state or disorder.

The present invention incorporates by reference methods and techniques well known in the field of molecular and cellular biology. These techniques include, but are not limited to techniques described in the following publications: Old, R. W. & S. B. Primrose, *Principles of Gene Manipulation: An Introduction To Genetic Engineering* (3d Ed. 1985) Blackwell Scientific Publications, Boston. Studies in Microbiology; V.2:409 pp. (ISBN 0-632-01318-4), Sambrook, J. et al. eds., *Molecular Cloning: A Laboratory Manual* (2d Ed. 1989) Cold Spring Harbor Laboratory Press, NY. Vols. 1-3. (ISBN 0-87969-309-6), Miller, J. H. & M. P. Calos eds., *Gene Transfer Vectors For Mammalian Cells* (1987) Cold Spring Harbor Laboratory Press, NY. 169 pp. (ISBN 0-87969-198-0). The DNA coding for the protein of the present invention may be any one provided that it comprises the nucleotide sequence coding for the above-mentioned protein of the present invention.

Identification of Agents with Potential Bone Anabolic Effect:

In one embodiment, the invention includes methods for identifying test agents or compounds regulating PAIGB activity. In the method, the agents regulating the bone-forming activity in a mammal are assayed by first incubating a sample comprising a PAIGB in a test medium containing the test agent. The next step is to determine the PAIGB activity wherein an increase in activity relative to PAIGB alone indicates the agent is a PAIGB activator and a decrease in activity indicates the agent is a PAIGB inhibitor.

Expression of PAIGB mRNA may be used as a tool to identify agents that alter PAIGB molecule expression. In one example, these agents (e.g. PTH 1-34) are anabolic and increase levels of PAIGB in bone tissue or in bone cells such as mesenchymal lineage (e.g. bone marrow mesenchymal stem cells, preosteoblastic or mature osteoblastic cells such as ROS 17/2.9, UMR106, MC3T3, SAOS-2, MG-63, TE85 and U2OS) that have osteogenic or bone forming activity. Specifically, a high through-put screen involves treating these osteoblastic cells with an agent such as a small molecule compound (e.g. 10-30 uM), natural product or peptide based compounds. The cells is treated in growth media containing 10% FBS for 4 to 18 hr. The media is removed and the cells is washed with PBS followed by the isolation of total RNA using an automated RNA extraction instrument (e.g., Applied Biosystems PRISM 6700). Typical yields of RNA from $1 \times 10^6$ cells is 20 ug total RNA. Following RNA isolation, 100 ng of RNA is analyzed by real time PCR (TaqMan analysis) as previously described in this application or other known methods in the art. Accordingly, total RNA may be isolated from a subject bone tissue, preferably a mammal, most preferably a human. Various techniques known in the art such as bone marrow aspirate, or bone core biopsy may be used to provide tissues for the analysis. The agents which induce PAIGB mRNA expression would indicate agents with bone anabolic potential.

Once the PAIGB inducing agent has been identified, the compound can be tested for its ability to induce the functional activity of the bone cell by inducing the expression of bone specific genes (including but not limited to alkaline phosphatase, osteocalcin, bone sialoprotein and Type I collagen) in bone marrow mesenchymal stem cells, preosteoblastic or mature osteoblastic cells. The compound can also be tested for its ability to induce mineralization in vitro using bone marrow stem cells, pre-osteoblastic and mature osteoblasts as assessed by Von Kossa or Alizarin Red staining. A bone anabolic agent may also elicit its effects by either increase osteoprogenitor cell or osteoblastic cell proliferation or by suppression of apoptosis in these cells. There are many methods in the art that are commercially available to measure these parameters including but are not limited to $^3$H-thymidine incorporation, 5-bromo-2'-deoxyuridine (BrdU) incorporation, 3-(4,5 dimethylthiazol-2-yl)-5-(3-carboxymethoxyphenyl)-2-(4-sulfophenyl)-2H-tetrazolium salt (MTS) assay, Caspase 3/7 assay, TUNEL assay (terminal deoxynucleotidyltransferase dUTP nick end labeling) (Darzynkiewicz, Z. et. al., Cytometry 27:1-20. 1997) or Annexin V assay (Martin, S. J., et. al., J. Exp. Med. 182:1545-1556, 1995 and Raynal, P. et. al., Biochim. Biophys. Acta. 1197: 63-93, 1994). The compounds could then be tested in vivo for their ability to promote bone formation using animal models known in the art including local injection of agent to mouse calvariae, systemic administration of agent in mature mice or young rats and system administration to ovariectomized rats or mice with established osteopenia.

Two Hybrid Screening

The mammalian and yeast two-hybrid systems are useful for studying protein:protein interactions. See, e.g., U.S. Pat. No. 6,251,602, U.S. Pat. No. 5,989,808, Chien et al., *Proc. Natl. Acad. Sci. USA* 88:9578-82 (1991); Fields et al., *Trends Genetics* 10:286-92 (1994); Harper et al., *Cell* 75:805-16 (1993); Vojtek et al., *Cell* 74:205-14 (1993); Luban et al., *Cell* 73:1067-78 (1993); Li et al., *FASEB J.* 7:957-63 (1993); Zang et al., *Nature* 364:308-13 (1993); Golemis et al., *Mol. Cell. Biol.* 12:3006-14 (1992); Sato et al., *Proc. Natl Acad. Sci. USA* 91:9238-42 (1994); Coghlan et al., *Science* 267: 108-111 (1995); Kalpana et al., *Science* 266:2002-6 (1994); Helps et al., *FEBS Lett.* 340:93-8 (1994); Yeung et al., *Genes & Devel.* 8:2087-9 (1994); Durfee et al., *Genes & Devel.* 7:555-569 (1993); Paetkau et al., *Genes & Devel.* 8:2035-45; Spaargaren et al., 1994 *Proc. Natl. Acad. Sci. USA* 91:12609-13 (1994); and Ye et al., *Proc. Natl. Acad. Sci. USA* 91:12629-33 (1994).

Variations of the system are available for screening yeast phagemid (see, e.g., Harper, Cellular Interactions and Development: A Practical Approach, 153-179 (1993); Elledge et al., *Proc. Natl. Acad. Sci. USA* 88:1731-5 (1991)) or plasmid (Bartel, 1993 and Bartel, *Cell* 14:920-4 (1993)); Finley et al., *Proc. Natl. Acad. Sci. USA* 91:12980-4 (1994)) cDNA libraries to clone interacting proteins, as well as for studying known protein pairs.

Yeast strains with integrated copies of various reporter gene cassettes, such as for example GAL.fwdarw.LacZ, GAL.fwdarw.HIS3 or GAL.fwdarw.URA3 (Bartel, in Cellular Interactions and Development: A Practical Approach, 153-179 (1993); Harper et al., *Cell* 75:805-16 (1993); Fields et al., *Trends Genetics* 10:286-92 (1994)) may be co-transformed with two plasmids, each expressing a different fusion protein. One plasmid encodes a fusion between protein "X" and the DNA binding domain of, for example, the GAL4 yeast transcription activator (Brent et al., *Cell* 43:729-36 (1985); Ma et al., *Cell* 48:847-53 (1987); Keegan et al., *Science* 231:699-704 (1986)), while the other plasmid encodes a fusion between protein "Y" and the RNA polymerase activation domain of GAL4 (Keegan et al., 1986). The plasmids may be transformed into a strain of the yeast that contains a reporter gene, such as lacZ, whose regulatory region contains GAL4 binding sites. If proteins X and Y interact, they reconstitute a functional GAL4 transcription activator protein by bringing the two GAL4 components into sufficient proximity to activate transcription.

Either hybrid protein alone is unable to activate transcription of the reporter gene, the DNA-binding domain hybrid, because it does not provide an activation function, and the activation domain hybrid, because it cannot localize to the GAL4 binding sites. Interaction of the two test proteins reconstitutes the function of GAL4 and results in expression of the reporter gene. The reporter gene cassettes contains minimal promoters that contain the GAL4 DNA recognition site (Johnson et al., *Mol. Cell. Biol.* 4:1440-8 (1984); Lorch et al., *J. Mol. Biol.* 186:821-824 (1984)) cloned 5' to their TATA box. Transcription activation is scored by measuring either the expression of β-galactosidase or the growth of the transformants on minimal medium lacking the specific nutrient that permits auxotrophic selection for the transcription product, e.g., URA3 (uracil selection) or HIS3 (histidine selection). See, e.g., Bartel, 1993; Durfee et al., *Genes & Devel.* 7:555-569 (1993); Fields et al., *Trends Genet.* 10:286-292 (1994); and U.S. Pat. No. 5,283,173.

Additional methodologies for Two-Hybrid Analysis or screening would be apparent to the skilled artisan. See for example, Finley et al., "Two-Hybrid Analysis of Genetic Regulatory Networks," in *The Yeast Two-Hybrid System* (Paul L. Bartel et al., eds., Oxford, 1997); Meijia Yang, "Use of a Combinatorial Peptide Library in the Two-Hybrid Assay," in The Yeast Two-Hybrid System (Paul L. Bartel et al., eds., Oxford, 1997); Gietz et al., "Identification of proteins that interact with a protein of interest: Applications of the yeast two-hybrid system," *Mol. & Cell. Biochem.* 172:67-9 (1997); K. H. Young, "Yeast Two-Hybrid: So Many Interactions, (in) so Little Time," *Biol. Reprod.* 58:302-311 (1998); R. Brent et al., "Understanding Gene and Allele Function with Two-Hybrid Methods," *Annu. Rev. Genet.* 31:663-704 (1997). It will be appreciated that protein networks can be elucidated by performing sequential screens of activation domain-fusion libraries.

Generally, these methods may include two proteins to be tested for interaction which are expressed as hybrids in the nucleus of a cell. One of the proteins is fused to the DNA-binding domain (DBD) of a transcription factor and the other is fused to a transcription activation domain (AD). If the proteins interact, they reconstitute a functional transcription factor that activates one or more reporter genes that contain binding sites for the DBD.

For example, the possible PAIGB interacting proteins can be identified by two hybrid methodology. A vector can be made containing transcription factor DBD plus protein X. When placed into a cell with a reporter gene, this fusion protein can bind to the reporter gene promoter, but it cannot activate transcription. A second vector can be made where unknown cDNAs are placed adjacent to the activation domain of a transcription factor. When placed into a cell containing the reporter gene, it cannot activate transcription, since it has no DNA binding domain. When the two vectors are placed into the same cell, a transcription factor is formed that can activate the reporter gene—if the protein made by the second plasmid binds to the X protein.

Full length (long and short form) or different portions of PAIGB may be cloned into two hybrid vectors. These vectors include but are not limited to pAS, pAS2-1, pGBT9, pGBKT7. The cloned PAIGB would represent bait for known or unknown protein(s) that is expressed as a fusion protein with known binding domain (e.g., GAL4 or LexA) (Serebriiskii I. G., et. al. BioTechniques 30: 634-655. 2001). The cDNA cloned into the activation domain (e.g., GAL4 or VP16) (Serebriiskii I. G., et. al. BioTechniques 30: 634-655.

2001) vectors may be from cDNA library made from different osteoblastic cell lines, bone, brain and other tissues where PAIGB is expressed.

Once the interacting partner is identified the full-length cDNA may be isolated and cloned. In addition interaction may be confirmed in mammalian two-hybrid system. Also, experiments may be performed that would more clearly define the binding domain within PAIGB as well as if PTH and/or other bone-forming agents regulate the interaction.

If the interacting partner of PAIGB is a novel gene expressed in osteoblasts additional experimental approach may be undertaken to position that protein in PTH signaling. However, if the PAIGB interacting partner is known gene of a known biological function, it may indicate the role of PAIGB in PTH signaling and induction of bone formation.

Genitically Modified Animals Baring Alterations to the PAIGB Gene:

Genetically engineered animals would include gene knock-outs, gene knock-ins and transgenics. The term "animal" when referred in transgenic animals includes all vertebrate animals, except humans. It also includes an individual animal in all stages of development, Including embryonic and fetal stages. A "transgenic animal" is an animal containing one or more cells bearing genetic information received, directly or indirectly, by deliberate genetic manipulation at a sub-cellular level, such as by microinjection or infection with recombinant virus. This introduced DNA molecule may be integrated within a chromosome, or it may be extra-chromosomally replicating DNA.

The genes may be obtained by isolating them from genomic sources, by preparation of cDNAs from isolated RNA templates, by directed synthesis, or by some combination thereof.

To be expressed, a gene is operably linked to a regulatory region. Regulatory regions, such as promoters, may be used to increase, decrease, regulate or designate to certain tissues or to certain stages of development the expression of a gene. The promoter need not be a naturally occurring promoter.

The methods enabling the introduction of DNA into cells are generally available and well-known in the art. The methods enabling the introduction of DNA into cells are generally available and well-known in the art. Different methods of introducing transgenes can be used. Generally, the zygote is the best target for microinjection. For example, in the mouse, the male pronucleus reaches the size of approximately 20 μm in diameter, which allows reproducible injection of 1-2 pL of DNA solution. The use of zygotes as a target for gene transfer has a major advantage. In most cases, the injected DNA will be incorporated into the host gene before the first cleavage (Brinster, et al., 1985). Consequently, nearly all cells of the transgenic non-human animal will carry the incorporated transgene. Generally, this will also result in the efficient transmission of the transgene to offspring of the founder since 50% of the germ cells will harbor the transgene. Microinjection of zygotes is a preferred method for incorporating transgenes in practicing the invention.

Retroviral infection can also be used to introduce a transgene into a non-human animal. The developing non-human embryo can be cultured in vitro to the blastocyst stage. During this time, blastomeres may be targets for retroviral infection (Jaenich, R. 1976). Efficient infection of the blastomeres is obtained by enzymatic treatment to remove the zona pellucida (Hogan et al., 1986). The viral vector system used to introduce the transgene is typically a replication-defective retrovirus carrying the transgene (Jahner et al., 1985; Van der Putten et al., 1985). Transfection is easily and efficiently obtained by culturing the blastomeres on a monolayer of virus-producing cells (Van der Putten, supra; Stewart et al., 1987). Alternatively, infection can be performed at a later stage. Virus or virus-producing cells can be injected into the blastocoele (Jahner et al., 1982). Most of the founder animals will be mosaic for the transgene since incorporation occurs only in a subset of the cells which formed the transgenic non-human animal. Furthermore, the founder animal may contain retroviral insertions of the transgene at a variety of positions in the genome; these generally segregate in the offspring. In addition, it is also possible to introduce transgenes into the germ line, albeit with low efficiency, by intrauterine retroviral infection of the midgestation embryo (Jahner et al., (1982) supra).

A third type of target cell for transgene introduction commonly used to develop knock-out and knock-in animals is the embryonal stem cell (ES). "Embryonic stem cells" or "ES cells" as used herein are cells or cell lines usually derived from embryos which are pluripotent meaning that they are undifferentiated cells (Evans, M. J., et al., 1981; Bradley, A., et al. 1984; Gossler, et al., 1986; and Robertson, et al., 1986). These cells are also capable of incorporating exogenous DNA by homologous recombination and subsequently developing into any tissue in the: body when incorporated into a host embryo. It is possible to isolate pluripotent cells from sources other than embryonic tissue by methods which are well understood in the art. Transgenes can be efficiently introduced into ES cells by DNA transfection or by retrovirus-mediated transduction. The resulting transformed ES cells can thereafter be combined with blastocysts from a non-human animal. The ES cells colonize the embryo and contribute to the germ line of the resulting chimeric animal (For review see Jaenisch, R., 1988).

Embryonic stem cells in mice have enabled researchers to select for transgenic cells and perform gene targeting. This allows more genetic engineering than is possible with other transgenic techniques. For example, mouse ES cells are relatively easy to grow as colonies in vitro. The cells can be transfected by 25 standard procedures and transgenic cells clonally selected by antibiotic resistance (See, for example, Doetschman et al., 1994, Gene transfer in embryonic stem cells: In Pinkert (Ed.) Transgenic Animal Technology: A Laboratory Handbook, Academic Press Inc., New York, pp. 115-146. Furthermore, the efficiency of this; process is such that sufficient transgenic colonies (hundreds to thousands) can be produced to allow a second selection for homologous recombinants. Mouse ES cells can then be combined with a normal host embryo and, because they retain their potency, can develop into all the tissues in the resulting chimeric animal, including the germ cells. The transgenic modification can then be transmitted to 5 subsequent generations.

Methods for deriving embryonic stem (ES) cell lines in vitro from early preimplantation mouse embryos are well known. See for example, Evans et al., 1981 Nature 29:154-156 and Martin, 1981, Proc. Nat. Aca. Sci. USA' 78:7634 7638. ES cells can be passaged in an undifferentiated state, provided that a feeder 10 layer of fibroblast cells or a differentiation inhibiting source is present. The term "somatic cell" indicates any animal or human cell which is not a sperm or egg cell or is capable of becoming a sperm or egg cell. The term "germ cell" or "germ-line cell" refers to any cell which is either a sperm or egg cell or is capable of developing into a sperm or egg cell and can therefore pass its genetic information to offspring. The term "germ cell-line transgenic animal" refers to a transgenic animal in which the genetic information was incorporated in a germ line cell, thereby conferring the ability to transfer the information to offspring. If such: offspring in fact possess some or all of that information, then they, too, are transgenic animals.

The genetic alteration of genetic information may be foreign to the species of animal to which the recipient belongs, or foreign only to the particular individual recipient. In the last case, the altered or introduced gene may be expressed differently than the native gene.

As used herein, a "transgene" is a DNA sequence introduced into the germline of an animal by way of human intervention.

As used herein, a "phenotype" refers to an observable property of an organism (in contrast to the genotype, i.e. genetic composition of the organism). In one embodiment, a "phenotype" refers to the entire physical, biochemical, and physiological makeup of a cell, e.g., having any one trait or any group of traits.

General methods for creating transgenic animals are known in the art, and are described in, for example, *Strategies in Transgenic Animal Science* (Glenn M. Monastersky and James M. Robl eds., ASM Press; Washington, D.C., 1995); *Transgenic Animal Technology: A Laboratory Handbook* (Carl A. Pinkert ed., Academic Press 1994); *Transgenic Animals* (Louis Marie Houdebine, ed., Harwood Academic Press, 1997); *Overexpression and Knockout of Cytokines in Transgenic Mice* (Chaim O. Jacob, ed., Academic Press 1994); *Microinjection and Transgenesis: Strategies and Protocols* (Springer Lab Manual) (Angel Cid-Arregui and Alejandro Garcia-Carranca, eds., Springer Verlag 1998); and *Manipulating the Mouse Embryo: A Laboratory Manual* (Brigid Hogan et al., eds., Cold Spring Harbor Laboratory Press 1994). The methods for evaluating the presence of the introduced DNA as well as its expression are also readily available and well-known in the art. Such methods include, but are not limited to DNA (Southern) hybridization to detect the exogenous DNA, polymerase chain reaction (PCR), polyacrylamide gel electrophoresis (PAGE) and Western blots to detect DNA, RNA and protein. The methods include immunological and histochemical techniques to detect expression of a PAIGB gene.

To determine if PAIGB plays a role in bone related disorders, transgenic mice were created that overexpressed the full-length gene (exons 1,2,3) in bone. The transgenic mice can also be created that overexpress any fragments of the above sequences in bone, e.g. the exon 2 splice variant. To establish a broad overexpression of both forms of PAIGB in bone as well as non-bone tissues, a ubiquitous promoter (e.g. CMV β-actin) can be used. In addition, expression of PAIGB can be made conditional using the Mifepristone-dependent gene inducible system. Bone-specific overexpression of the rat cDNA can be driven by promoters such as the rat 3.6 kb type I collagen or rat 1.7 kb osteocalcin promoter. The rat 3.6 kb type I collagen promoter is useful for providing early expression in developing bone whereas the rat 1.7 kb osteocalcin promoter, may confer a more bone-restricted pattern of expression. The same constructs are also used to generate transgenic rats. For conditional expression of PAIGB, the osteocalcin promoter (Capparelli, F. B., Endocrinol. 138:2109-2116, 1997) drives the gene inducible system and the Gal4 minimal promoter drives PAIGB. Independent transgenic lines are crossed and double-transgenic mice are treated with Mifepristone to regulate PAIGB expression on demand. Phenotyping of the transgenic animals may involve a combination of in vivo and ex vivo assays. Such phenotyping may include BMD analysis (pQCT), micro artitechture analysis (bone volume, conductivity density, trabecular number, trabecular spacing, trabecular thickness, etc) as determined by microCT analysis. Other analysis include determining mineral apposition rate as determined by calcein incorporating into actively mineralyzing bone. Furthermore, the effect of transgene on bone phenotype can be assessed on histological level by measuring osteoblast number, osteoclast number, as well as the number of apoptotic osteoblastic cells. An anabolic effect provides the proof of concept that PAIGB molecule is indeed a potential new target for osteoporosis. Furthermore, these transgenic animals are used to determine if PAIGB overexpression can rescue ovariectomiced induced osteopenia in rats and mice in these established osteopenia models (Y. P. Kharode et al. J. Bone Min. Res. 14 (1): S523, 1999., Y. P. Kharode et al. J. Bone Min. Res. 16 (1): S540, 2001).

Transgenic animals can be used for the analysis of the bone phenotype of various bones of the skeleton including flat bones (skull, scapula, mandible and ileum) and long bones or axial bones (tibia, femur and humerus) and such with various histomorphometric parameters known in the art. Bone phenotype can be characterized by the production of osteocalcin, alkaline phosphatase, type I collagen and by changes in bone mass and bone parameters. Osteocalcin, alkaline phosphatase and type I collagen are known markers for osteoblasts, or bone tissue.

Bone parameter refers to bone density, bone strength, trabecular number, bone size, bone tissue connectivity and the like.

In addition, PAIGB transgenic animals can be tested if they are protected from bone loss in various bone loss models including ovariectomy induced osteopenia, glucocorticoid induced osteopenia, and various disuse models and such which are known in the art. The effectiveness of combination of various bone anabolic agents (e.g. identified small molecules) can be investigated and determined to further modify the bone phenotype in an anabolic fashion (synergistically, additively) or in a catabolic manner.

PAIGB transgenic animals can be used for identifying agents effective for the treatment of bone related disorders. An agent may be administered to the transgenic animal of present invention. Alteration in PAIGB expression in cells of the treated animal can be measured, and compared with PAIGB expression in untreated control animals.

PAIGB transgenic animals can be used to study the role of PAIGB in osteoprogenitor and osteoblastic cell activity, proliferation rates and apoptosis rates which collectively influence bone formation.

The invention also provides animals in which the PAIGB gene has been inactivated. This can occur in mice for example as a test model for in vivo testing of the results of inactivated PAIGB. The results in wild type animals, i.e. corresponding to the knock out animal with the exception of the inactivated PAIGB gene, can be compared with the results in the knock out animal to ascertain whether an agent or compound has been tested. Also on the basis of the data provided in the prior art a knock out system, e.g. using genetic modification, can be achieved. For example, one or both copies of one of the animal's PAIGB genes can be partially or completely deleted by homologous recombination or gene targeting, or can be inactivated by the insertion or substitution by homologous recombination or gene targeting of exogenous sequences.

In one embodiment, the present invention provides for the gene information for to develop knock out PAIGB mouse. In addition, a knock-out animal may be developed by introducing a mutation in the PAIGB sequence, thereby generating an animal which does not express the functional PAIGB gene anymore. Such knock-out animal is useful e.g. for studying the role of PAIGB in bone related disorders.

To circumvent possible lethality problems, the cre/loxP (Andras Nagy, Genesis 26:99-109, 2000) system can be used. This allows tissue specific or inducible inactivation of the target gene.

Accordingly, a conditional 129Sv/Ev mouse knockout is created that is dependent on expression of Cre recombinase specifically in bone. PAIGB gene expressed in brain and a null allele expressed in this tissue may result in embryonic lethality. Therefore, conditional approach is selected to produce a PAIGB null animal. Deletion of the targeted allele in bone is performed by crossing gene-targeted animals with transgenic mice expressing Cre specifically in bone. 129Sv/Ev transgenic mice are created where Cre will be driven by either the rat 3.6 kb type I collagen promoter or the rat 1.7 kb osteocalcin promoter. The functionality of these Cre transgenic animals is tested in crosses with the ROSA transgenic mice (these mice have a Lac Z reported flanked with lox P sites) that results in lacZ expression in bone as an indicator of Cre activity. In addition, a Z/EG double reporter transgenic mouse containing lacZ and EGFP may be utilized. Mouse BAC clones are obtained from Invitrogen by hybridization screening using a 790 bp PAIGB probe comprising exon 1 and additional 5' sequence (SEQ ID NO:15). If the PAIGB gene is confirmed to be present, the BAC clone may be used to construct the gene-targeting vector. The gene-targeting vector includes a neomycin selection cassette flanked with frt sites (for flp recombinase-dependent removal if necessary) and lox P sites positioned upstream and downstream of the region to be deleted.

The expected phenotype is one where bone development is not normal or may resemble the loss of bone seen in bone diseases. Phenotyping of the targeted animals involves a combination of in vivo and ex vivo assays. The failure to develop normal bone or remodel bone normally in the adult provides the role of PAIGB in bone development its use as a novel target for bone related disorders.

Knock-out animals can be used to analyze the bone phenotype of various bones of the skeleton including flat bones (skull, scapula, mandible and ileum) and long bones or axial bones (tibia, femur and humerus) and such with various histomorphometric parameters known in the art.

In addition, PAIGB knock-out animals can be used to analyze the effects, specificity and dependency of various agents such as small molecules on modulation of PAIGB activity.

Furthermore, PAIGB knock-out animals can be used to asses osteoprogenitor and osteoblastic cell activity, proliferation rates and apoptosis rates in the absence of PAIGB.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion, embodiments and these Examples, one skilled in the art can ascertain the art will readily appreciate that many modifications are possible in the exemplary embodiments without materially departing from the novel teachings of this inventions, and without departing from the spirit and scope thereof, can make various changes and modifications of the invention to adapt it to various usages and conditions. Accordingly, all such modifications are intended to be included within the scope of this invention as defined in the following claims.

General Methods

Rapid Amplification of Differentially Expressed Genes (RADE)

Total RNA was isolated and each RNA sample was then treated with 20 units of DNAse (Ambion, Austin, Tex.). After RNA cleaning, samples were split into three reverse transcription (RT) reactions. Each RT reaction contained 4 μg RNA, 1000 units SuperScript II RT (Gibco), 100 μM dNTPs and 0.2 μM anchor primer in a final volume of 100 μl. Anchor primers had the sequence (5'→3') $T_{11}A$, $T_{11}C$, or $T_{11}G$. For differential display each cDNA sample was subjected, in duplicate, to 80 PCR reactions using the appropriate anchor primer and one of 80 arbitrary primers (HAPs 1-80; Genhunter). PCR reactions contained in a final volume of 20 ul, 20 ng cDNA, 2 μM dNTPs, 0.2 μM anchor primer, 0.2 μM arbitrary primer, 1 unit Taq polymerase (Applied Biosystems (AB), Foster City, Calif.), and 2.5 μCi [α-$^{33}$P] dATP (2000 Ci/mmole). PCR conditions were as follows: 1 cycle of 92° C./2', 40 cycles of [92° C./15", 40° C./2', 72° C./30"], and 1 cycle of 72° C./5'. PCR samples were then loaded onto a 50 cm 6% sequencing gel and run at 200 volts constant. Differentially expressed bands were excised from the dried gel. Identical primers and PCR conditions as in the original reaction were used in order to re-amplify DNA samples recovered from differential display gel. Products were ligated into pGem-T Easy (Promega Madison, Wis.).

RNA Isolation

RNA isolation was performed on bone as well as from different cell lines used during experimentation. RNA was isolated from rat tibiae as follows. Following euthanasia by $CO_2$ asphyxiation tibiae were dissected free of soft tissue as rapidly as possible with autoclaved instruments, wiped with autoclaved gauze soaked in ethanol and the epiphysis broken off at the proximal growth plate by hand and discarded. The tibia was then cut transversely with bone cutters just distal to the proximal growth plate and just proximal to the distal tibia-fibula junction to expose the trabecular bone and the bone marrow. The trabecular bone and marrow cavity was flushed with ice cold sterile PBS using a Lancer liquid transfer pipette (Oxford Labware, St. Louis, Mo.) to remove the marrow and the cleaned bone placed in liquid nitrogen.

A Bessman tissue pulverizer (Fisher Scientific, Pittsburgh, Pa.), rinsed in 100% ethanol and pre-cooled in liquid nitrogen, was used to reduce 4 tibiae at a time to a powder which was then transferred into 50 ml tubes containing 4 ml Trizol reagent (Gibco BRL, Rockville, Md.). The powder was then further homogenized using a hand-held Tissue-Tearer homogenizer (Fisher scientific, Pittsburgh, Pa.) before the tube was placed on dry ice until RNA could be recovered. RNA was recovered on the same day; or the samples were stored in the Trizol at −80° C.

Frozen samples were brought to room temperature and centrifuged at 12,000 g for 10 min to remove excess mineral. The supernatant was collected and 0.2 ml of chloroform was added per 1 ml of Trizol. The tube was shaken vigorously and allowed to stand 2-3 min at room temperature before being centrifuged at 12,000×g at 4° C. for 15 min. The aqueous (upper) layer was then transferred to a new tube and 0.5 ml isopropanol added per 1 ml Trizol used. This was incubated at RT for 10 min and then centrifuged at 4° C., 12,000×g for 10 min. The supernatant was removed and the RNA pellet washed with cold 75% ethanol: 25% RNAse-free water (1 ml ethanol per 1 ml Trizol used) by being vortexed and then centrifuged at 7,500×g for 5 min at 4° C. After removal of the supernatant, the pellet was briefly dried, resuspended in sterile water and stored at −80° C.

In other experiments ROS 17/2.8 and UMR106 rat osteoblastic cells (ATCC# CRL1661), C3HT101/2 (mouse fibroblast from ATCC# CCL226) and human U2OS osteoblastic cells (ATCC# HTB96) were used. Treated cells were washed twice with PBS and the RNA was isolated with either Trizol (Invitrogen) or RNA-Bee reagent (TEL-TEST Inc, Friendswood, Tex.). Final isolation of RNA was performed according to manufacturer protocol.

Northern Blot

Isolated RNA was run on 1.2% agorase gel in 1×MOPS ((3-[N-morpholino]propanesulfonic acid) buffer) and formaldehyde. RNA gel was run in 1×MOPS (Sigma). RNA was transferred on nylon membrane (S&S) using Turbo-blot according to instruction provided by manufacturer (S&S). RADE fragment(s) as well as GAPDH or ciclophylin were labeled using random prime labeling kit (Gibco, BRL) according to provided instructions. Hybridization with labeled probes was performed using ExpressHyb (Sigma), at 68° C. over night. Blots were washed 2 times at room temperature for 15 min in low stringency buffer (2×SSC, 0.1% SDS), and 1 time at 65° C. for 15 min in low stringency buffer (0.1×SSC, 0.1% SDS). Blots were exposed over night using Kodak film.

RT-PCR and Real-Time PCR (TaqMan)

RNA samples were subject to RT-PCR and Taq-man analysis using probe and primers to PAIGB polynucleotide sequences and GAPDH as well as 18S ribosomal RNA. RT-PCR was done using TaKaRa kit (Panvera, Shiga, Japan) according to manufacturer recommendation. RT reaction was done under following conditions: 30° C. for 10 min, 42° C. for 50 min, 99° C. for 5 min and 4° C. for 5 min. PCR conditions were: 94° C. for 5 min, 35 cycles of 94° C. for 2 min, 62° C. for 30", 72° C. for 1 min and 30 sec, and 72° C. for 10 min. The PCR products were separated on 1% agarose gel.

Applicants performed multiplex real time PCR (TaqMan) analysis on previously DNAsed samples using gene specific probe and primers and 18S ribosomal RNA probe and primer sets purchased from Applied Biosystem. (Foster City, Calif.) The samples were DNAsed according to the protocol provided by Ambion (DNA-free kit). TaqMan probe and primers for PAIGB was identify using Primer Express computer program. The sequence for rat PAIGB TaqMan probe was 6FAM-5'CCCACATTCCTAMCACATCCTCCT-GCAA (SEQ ID NO: 16) forward and reverse primers were 5'CCATGCTCTGATATGGACCCTT 3' (SEQ ID NO:17) and 5' TCAAACTCAGGCTGTGCCATAC 3' (SEQ ID NO:18) respectively. The final concentrations for probes were 500 nM and 40 nM for PAIGB and 18S ribosomal RNA or GAPDH respectively. The concentrations of the primers were 500 nM for PAIGB forward and reversed primers while 18S primers were 10 and 20 nM for forward and reversed primer respectively or 40 nM for GAPDH primers. Standards for rat samples were made from rat tibia or brain RNA in the range of 250 ng to 0.1 ng, while standards for mouse specific TaqMan were made from mouse brain RNA and human standards from human brain RNA (Clonetech, Palo Alto, Calif.) spanning the same range of concentration. Primers and probes for mouse PAIGB were: forward 5' TGTGAGGAGGCTTGGTACTCAG 3' (SEQ ID NO:19), reverse, 5' GAGATTCCACTGCAATCATTGG 3' (SEQ ID NO:20) anti-sense and probe 5' 6FAM-TGACACGGAC-CCTGTGGCACMGA (SEQ ID NO:21). Primers and probes for human PAIGB were: forward 5' ATGCTTGTG-GCCAATGCA 3' (SEQ ID NO:22), reverse 5' GATA-GAGAGGGAAAACAGTCMGMGA 3'(SEQ ID NO:23), and PROBE 5' 6FAM-ACCCCTCAGGGCTCAGCTAGA-CATTGC 3'(SEQ ID NO: 24). The Taq-man analysis was done using ABI 7700 Sequence Detector under following conditions: 30 min at 48° C., 10 min at 95° C. and 40 cycles of 15 sec at 95° C. and 60 sec at 60° C. Analysis of real-time PCR analysis was performed using (Sequence Detector, Macintosh) program.

5' RACE

The 5' RACE was done on RNA samples form rat brain and tibia using Clontech 5' RACE kit according to manufacturer recommendation. Briefly, 3 rounds of 5' RACE were performed using adapter primer AP1 5'CCATCCTAAT-CAGA CTCACTATAGGGC 3' (SEQ ID NO:25) and gene specific primers: GSP1 5' GATTCCACTGCA ATGGTTG-GTCCT 3' (SEQ ID NO:26), GSP2 5' MCCGGGATG-GTCGTCACCGCGTG 3' (SEQ ID NO:27) and GSP3 5'CTGTCCATCTGCCGGATATTCTCTG 3' (SEQ ID NO:28). PolyA RNA was used to synthesize first cDNA strand. Second strand cDNA were synthesized and adapters ligated to it. 5' RACE PCR was done using AP 1 (adaptor primer 1) and gene specific primers as forward and reverse primer respectively using following conditions: 94° C. for 30 sec, 5 cycles of 94° C. for 5 sec, 72° C. for 4 min, 5 cycles at 94° C. for 5 sec, 70° C. for 4 min and 25 cycles of 94° C. for 5 sec and 68° C. for 4 min, PCR reaction was ligated into T-A cloning vector. The DNA isolated from clones containing inserts different sizes was subject to sequencing.

Screening the cDNA Library

Lambda ZAP II rat brain cDNA library was used in order to obtain full-length cDNA clone representing PAIGB. This library was chosen for it allows efficient in vivo excision from lambda ZAP II vector and re-circularization of any cloned insert contained within a lambda vector to form a phagemid (pBluescript SK(−)) containing the clone insert. The library screen was done according to manufacturer recommendations (Stratagene, La Jolla, Calif.). Three rounds of screening were performed using RADE insert as probe. Once the positive clones were identified inserts were subject to sequencing using T3 and T7 primers as well as internal primers.

Cell Culture

Five cell types were primarily used in our experiments. Rat osteoblast cell line (ROS 17/2.8) that expresses moderate levels of PTH receptor 1 (Rodan et al, Rev. Eukaryotic Gene Expression 1:85-98, 1991) were used to perform in vitro experiments. ROS cells were maintained under standard cell culture conditions: 10% heat inactivated FBS in Dulbecco's Modified Eagle Medium with Nutrient Mixture F-12 (DMEM/F12) media, 1% Penicillin/Streptomycin and 1% Glutamax. Mouse cell line $C_3H10T\frac{1}{2}$ (ATCC# CCL226) as a representative of mouse osteoprogenitor cell line were maintained in Eagles Minimal Essential Media (EMEM) with the addition of 10% heat inactivated FBS and 1% Penicillin/Streptomycin and 1% Glutamax. UMR106 rat osteoblastic cells (ATCC# CRL1661) were cultured in Dulbecco's Modified Eagle Medium (DMEM) supplemented with 10% heat inactivated FBS, 1% Penicillin/Streptomycin and 1% Glutamax. The U2OS human osteoblastic cells (ATCC# HTB96) were cultured in McCoy's 5A Medium Modified supplemented with 10% FBS, 1% Penicillin/Streptomycin and 1% Glutamax. The human HOB-03-CE6 cell line (Bodine, V. N. P., et. al., J. Cell. Biochem., 65: 368-387,1997) was maintained in phenol red free DMEM/F12 media supplemented with 10% heat inactivated FBS and 1% Penicillin/Streptomycin and 1% Glutamax.

The compounds used in in vitro cell cuture experiments were: human PTH (1-34) purchased from Biachem (Torrance, Calif.), SQ 22536 (Calbiochem La Jolla, Calif.), Forskolin, Isoproterenol and prostaglandin $E_2$ ($PGE_2$) were purchased from Sigma (St. Louis, Mo.), Calcitonin (Salmon T-3660) (Sigma, St. Louis, Mo.), bone morphogenic protein 2 and 6 (BMP2, BMP6) and the inhibitor of PKC 19-27 was obtained from Calbichem (La Jolla, Calif.).

Measurements of Total and Trabecular BMD in Proximal Tibia

The total density of the proximal tibia was evaluated in anesthetized rats using peripheral quantitative computed tomography (pQCT) with XCT-960M (Stratec Medizintechnik, Pforzheim, Germany). The baseline and post-treatment measurements were performed in anesthetized rats as follows: The right hind limb was passed through a polycarbonate tube with a diameter of 25 mm and taped to an acrylic frame with the ankle joint at a 90° angle and the knee joint at 180°. The polycarbonate tube was affixed to a sliding platform that maintained it perpendicular to the aperture of the pQCT. The platform was adjusted so that the distal end of the femur and the proximal end of the tibia would be in the scanning field. A two dimensional scout view was run for a length of 10 mm and a line resolution of 0.2 mm. After the scout view was displayed on the monitor, the proximal end of the tibia was located. The pQCT scan was initiated 3.4 mm distal from this point. The pQCT scan was 1 mm thick, had a voxel (three dimensional pixel) size of 0.140 mm, and consisted of 145 projections through the slice. After the pQCT scan was completed, the image was displayed on the monitor. A region of interest including the tibia but excluding the fibula was outlined. The soft tissue was automatically removed using an iterative algorithm. The density of the remaining bone (Total density) was reported in $mg/cm^3$. The change in total density was calculated for each animal by subtracting post-treatment and baseline total density values.

Animal Work

Female Wister rats 4 weeks of age were treated with vehicle (saline) and human PTH (1-34) at a dose of 40 µg/kg of body weight for eight days. Prior to PTH administration animals were ovariectomized (OVX). Three weeks post OVX total BMD was measured to determine if osteopenia was established. Subcutaneous injection of PTH once a day represented intermittent administration of PTH, while osmotic pump with release rate of 40 µg/kg/day implanted under the skin represented continuous way of PTH administration. On the eight day of treatment, 6 hours post treatment animals were scarified and samples were collected for further analysis. Each treatment group contained 8 animals.

Example 1

Effect of Total BMP by Intermittent Adminstration of PTH (1-34)

Figure 1:
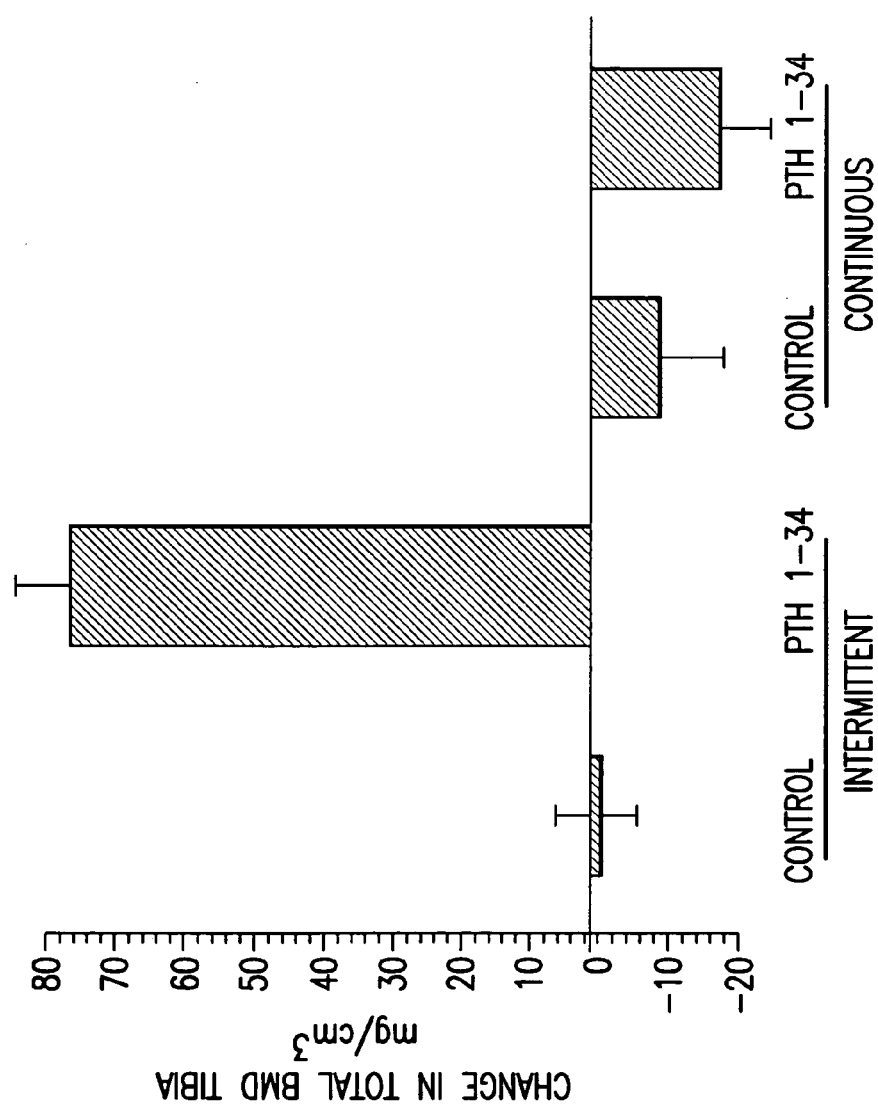
FIG. 1 shows the effect of PTH 1-34 on total BMD in the tibia by intermittent injection of PTH (referred to in Example 1).

PTH (1-34) in a dose of 40 µg/kg was administered for eight days to the 3 weeks OVX rats in intermitted and continuous manner to induce anabolic and catabolic PTH effects respectively. As described in General Method section, intermittent administration of PTH was presented by once a day subcutaneous injection of PTH while continues administration was presented with osmotic pumps implanted under the skin with release rate of 40 µg/kg a day. Total bone mineral density was measured using pQCT. Intermittent PTH injection induced significant increases in total BMD, with Δ BMD of 80 $gr/cm^2$ (FIG. 1). Continuous PTH administration did not induce any changes in already osteopenic bones (FIG. 1). Thus, PTH exerts its effect on bone anabolic and catabolic (i.e., causing a decrease in BMD) depending of the way of its administration.

Example 2

RADE

Figure 2A:
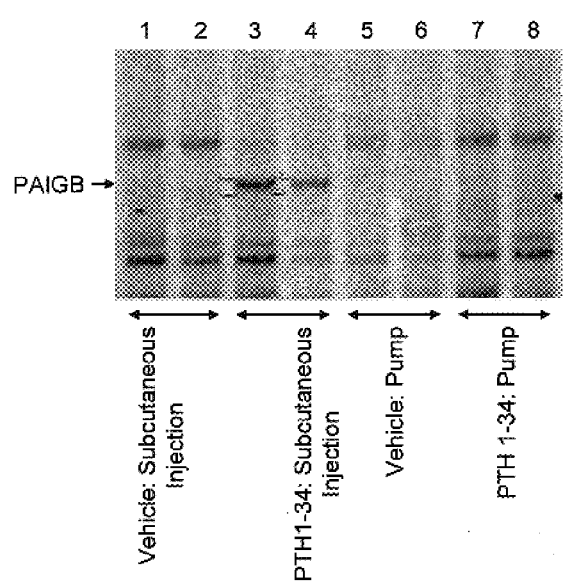
FIG. 2A shows the identification of PAIGB from a RADE experiment using rat tibia RNA obtained from intermittent and continuous administration of PTH 1-34 (referred to in Example 2).
Figure 2B:
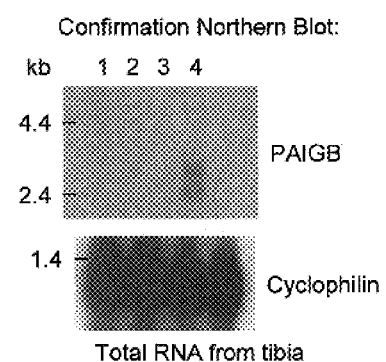
FIG. 2B shows the confirmation Northern Blot of PAIGB being regulated by intermittent administration of PTH 1-34 (referred to in Examples 2 and 7).

Total RNA from bone samples after intermittent and continuous administration was isolated and submitted to differential display analysis. Twenty-four differentially express genes were identified with differential changes of 2 fold and more. PAIGB gene from RADE was induced in the RNA from bones after intermittent injection (FIG. 2) while continuous PTH injection did not induce any changes in expression level of PAIGB. Basal level of expression of this gene was very low as seen in the FIG. 2A (lanes 1, 2, 5, 6) and 2B (lanes 1, 3). Our results showed that PAIGB expression was induced only when PTH was administered in intermittent manner. DNA that represented PAIGB was isolated from RADE gel and subjected to PCR. A band of 400 bp correlated well to estimate size of PCR product from RADE gel. After T-A cloning 400 bp band was sequenced and submitted to a bioinformatic analysis (BLAST search (NCBI)). The initial BLAST search indicated that PAIGB did not match to any known gene. The EST data-base search identified two sequences, one from rat Acc # AA850640 and one from mouse Acc # A1070533 that were 98 and 99% identical to PAIGB sequence respectively which further confirmed that PAIGB is an expressed gene.

Example 3

Cloning of Rat PAIGB

The full length of cDNA for PAIGB was cloned by screening brain λZAP cDNA library (Startagene) as well as using 5' RACE (Invitrogen). Three rounds of 5' RACE were performed on RNA samples from bone after intermittent PTH treatment as well as from brain (initial limited Northern blot analysis on Clontech (CA) multiple tissues blot indicated expression of PAIGB in brain). Original radiolabeled PAIGB (400 bp) was used as a probe for library screen. The DNA from four sets of plasmids containing inserts of different size was isolated and sequenced from both ends until the sequences overlapped at least 100 bp. Based on sequence and alignments between different clones the 2.2-kb clone containing ORF was obtained. The full-length sequence is shown in SEQ ID NO: 1.

Example 4

Cloning of Mouse and Human PAIGB

Rat sequence for PAIGB was submitted to blast analysis using mouse and human EST databases. Several ESTs that were identified matched 98% to rat PAIGB in both 5' and 3' end. The DNA sequence identity within the open reading frame (ORF) of human PAIGB compared to rat and mouse is 87%. Furthermore, the amino acid sequence identity of human PAIGB compared to rat and mouse is 82%. When comparing rat PAIGB to mouse there is 95% DNA sequence identity within the ORF and 97% sequence identity at the amino acid level. Mouse specific primers were designed (SEQ ID NO: 29,30,31,32) for RT-PCR to clone the mouse homologue of PAIGB (SEQ ID NO: 7). A 1,086 bp fragment of human PAIGB (SEQ ID NO: 33) was cloned using internally designed primers. The full-length sequence (SEQ ID NO: 3) was later obtained from Invitrogen. The cDNA clone was provided in the pCMVSPORT6 plasmid along with the nucleotide sequence. The human PAIGB sequence was aligned to full-length rat PAIGB sequence to assess the level of identity and similarity.

Example 5

Bioinformatic Analysis of Human, Rat and Mouse PAIGB

Human PAIGB sequence from human HOB O3-CE6 cDNA (1,086 bp, SEQ ID NO: 33) was used to search public data bases. A 2824 bp fragment was found using Incyte LifeSeq Gold Database (Incyte, Palo Alto, Calif.) with the hit template ID-474616.19. The E value is 0.0 and the identity is 1093/1094 (99%). It encodes for a 145 amino acid protein. By using 474616.19 to blastn Celera human genome sequence database, it was found that human full-length PAIGB has three exons and the first methione is in exon 1.

Mouse PAIGB was found by using human protein sequence to blastn Celera mouse genome fragment sequence database. Furthermore, a full-length rat clone was sequenced, and its sequence matched the human and mouse orthologues.

Figure 3:
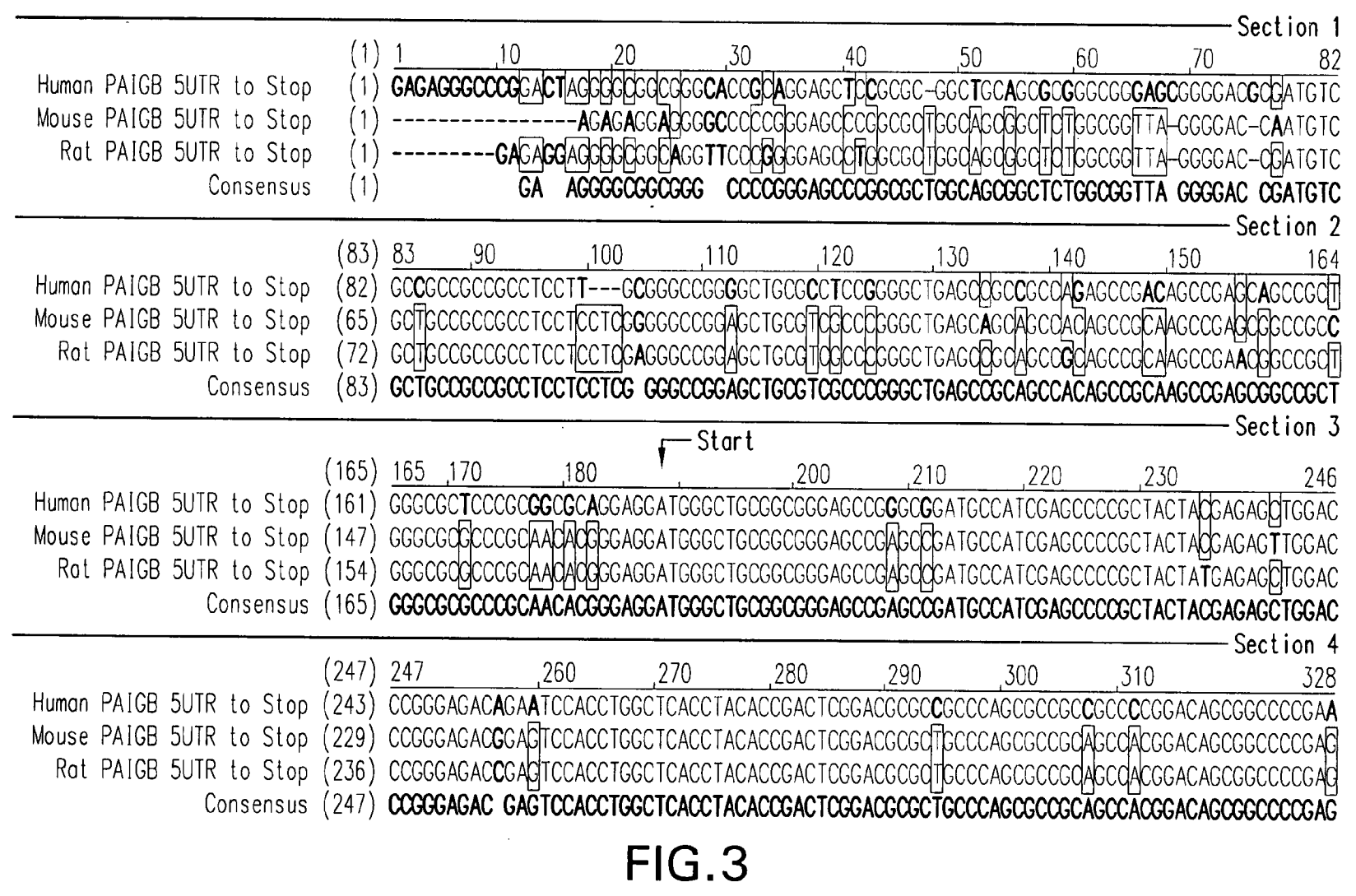

In order to confirm the start of transcription, 5' sequences of mouse, and human were extracted from Celera database and compared to each other as well as to rat sequence. There is a long 5' reading frame before the first methione in all three species. By using 474616.19 to blast public EST database EST AU120917 was identified that added 5 bp to the 5' end and the reading frame kept open (Expect=0.0, Identities=740/744 (99%)). However, in the mouse 5' sequence that has high homology to the human 5' transcribed sequence, a stop codon was found. This indicated that Applicants obtained the full-length gene in mouse. The cDNA and protein alignments are shown for human, mouse and rat in FIGS. 3 and 4.

The generated gene sequence was identified by conducting a BLAST (Basic Local Alignment Search Tool; Altschul et al., *J. Mol. Biol.* 215:403-410 (1993); see also www.ncbi.nlm.nih.gov/BLAST/) search for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL, and DDBJ databases). The 4.5×DNA sequence obtained was analyzed using the BLASTN algorithm provided by the National Center for Biotechnology Information (NCBI). For convenience, the expected value of observing a match of a cDNA sequence to a sequence contained in the searched databases merely by chance as calculated by BLAST are reported herein as "E" values. The E value estimates the statistical significance of the match, specifying the number of matches with a given score, that are expected in a search of a database of this size absolutely by chance.

Example 6

Identification and Cloing of Human and Mouse PAIGB Splice Variant

Cloning the human (SEQ ID NO:5) and mouse PAIGB (SEQ ID NO:9) was performed using human and mouse brain mRNA (Clontech, Palo Alto, Calif.) as a template for the reverse transcription reaction (Takara, Panvera, Shiga, Japan). The reverse transcription reaction was subjected to PCR amplification using human (SEQ ID NO:34, 35) and mouse (SEQ ID NO:31, 32) specific primers, elongase (Invitrogen, Carlsbad, Calif.) and supplemented with GC melt (Clontech, Palo Alto, Calif.). The PCR products were subsequently cloned into the pCR Blunt II TOPO vector (Invitrogen, Carlsbad, Calif.). The cloned sequences comprised human and mouse PAIGB, which contained exons 1, 3 and were missing exon 2.

Example 7

Northern Blot and RT-PCR Analysis of PAIGB Expression

Figure 5:
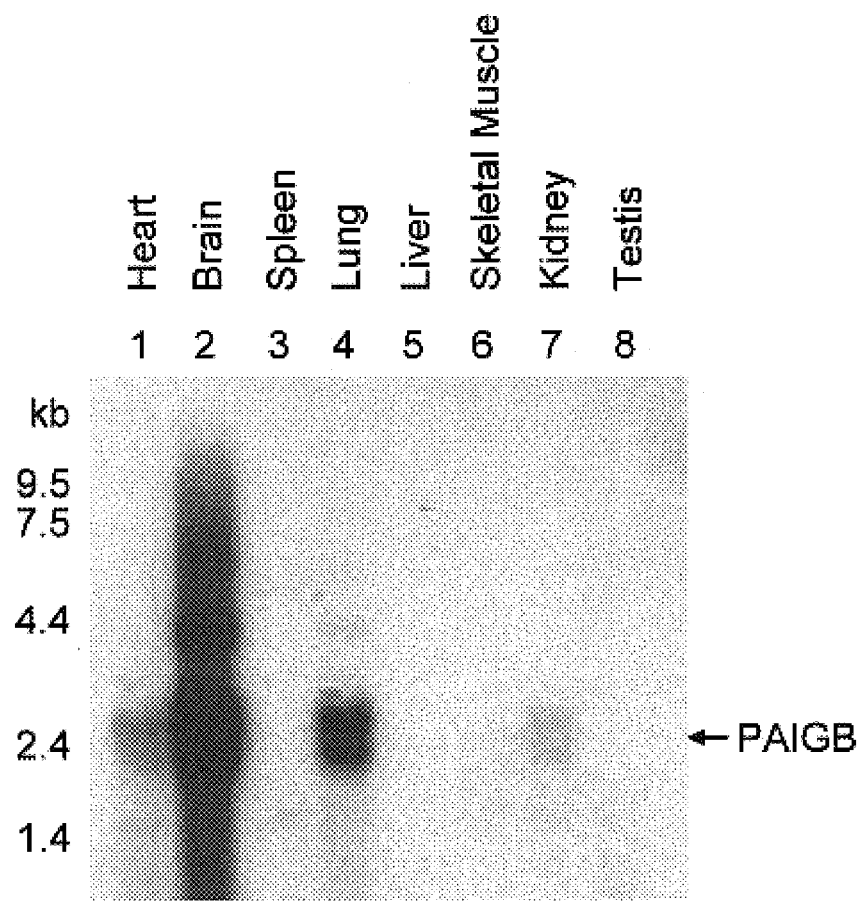
FIG. 5 shows a mouse multiple tissue Northern Blot demonstrating the expression pattern of PAIGB (referred to in Example 7).

In order to confirm the results from RADE experiments data, Northern blot analysis was done on RNA samples from rat tibia after intermittent and continuous PTH injections. As shown on FIG. 2B, the PAIGB expression was detected only in the samples from intermittently treated rats but not in vehicle or in rats that received continuous PTH treatment. Phosphor-imager analysis revealed increase of 36 fold when compared from tibia RNA samples of vehicle treated rats. In addition a multiple tissue northern blot was performed on the samples provided by commercially available blots. The northern blot analysis indicated very abundant expression of PAIGB in brain, but little expression in heart and lung. Spleen, liver, skeletal muscle, kidney and testis did not show any expression of PAIGB (FIG. 5).

Figure 6:
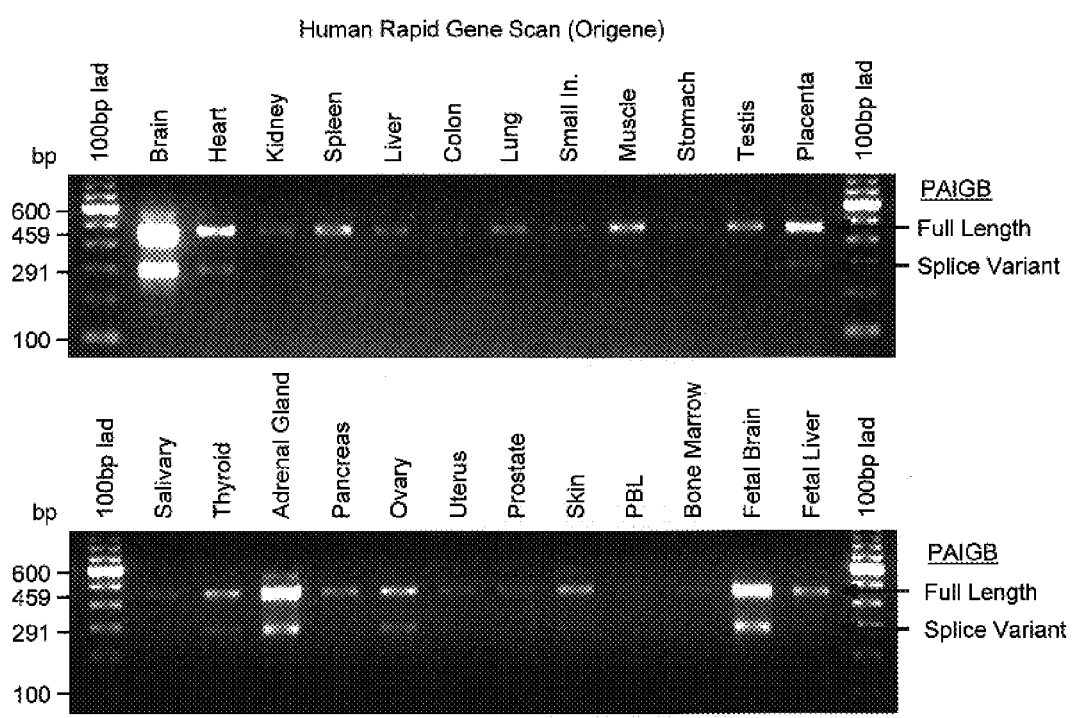
FIG. 6 shows the expression pattern of PAIGB full length and splice variant using a human Origene cDNA panel (referred to in Example 7).
Figure 7:
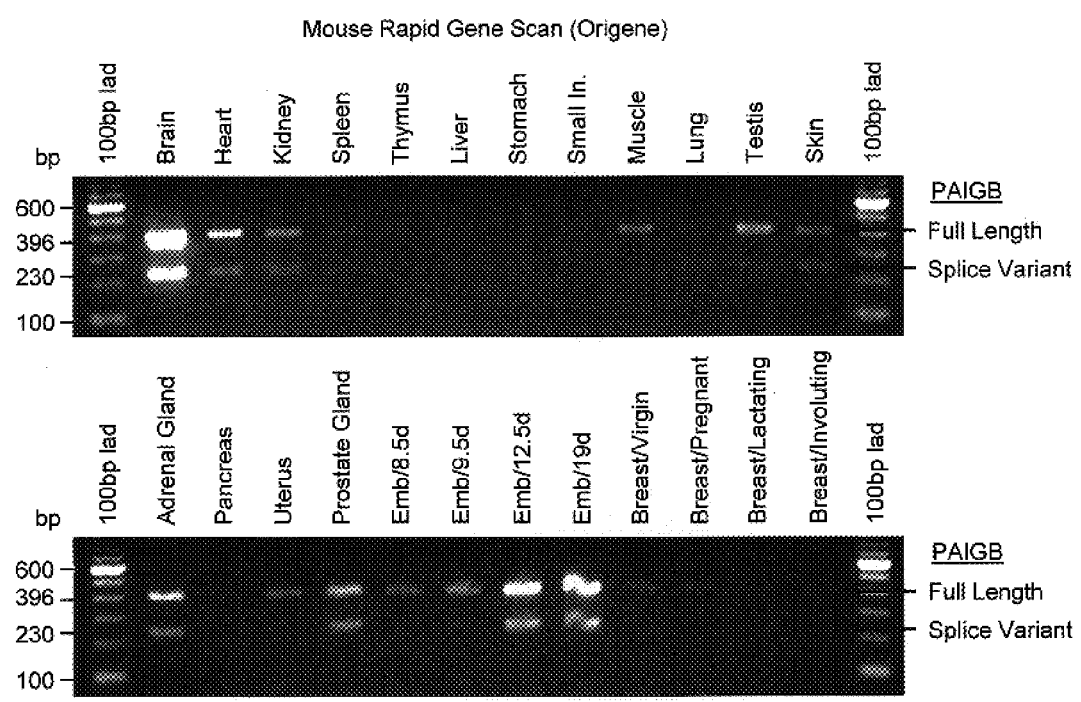
FIG. 7 shows the expression pattern of PAIGB full length and splice variant using a mouse Origene cDNA panel (referred to in Example 7).

To determine expression pattern of human and mouse full length and analog for PAIGB Applicants used human and mouse primers described in General methods (SEQ ID NO: 36, 37, 38, 39). Origene cDNA panel from 24 tissues of human and mouse origin was used. Data shown on FIGS. 6 and 7 indicate that expression pattern of human and mouse PAIGB are similar as seen in the mouse multiple tissue northern blot. High level of expression in brain with less expression in heart and liver. In addition, the Origene panel demonstrated significant levels of PAIGB expression in the adult adrenal gland and in samples from 12.5 and 19 days old embryos. These data indicate expression of PAIGB in the late stages of embryonic development. In addition, the data indicates that in most of the tissues examined both the PAIGB full length and exon 2 splice variant are co-expressed.

Example 8

Figure 8:
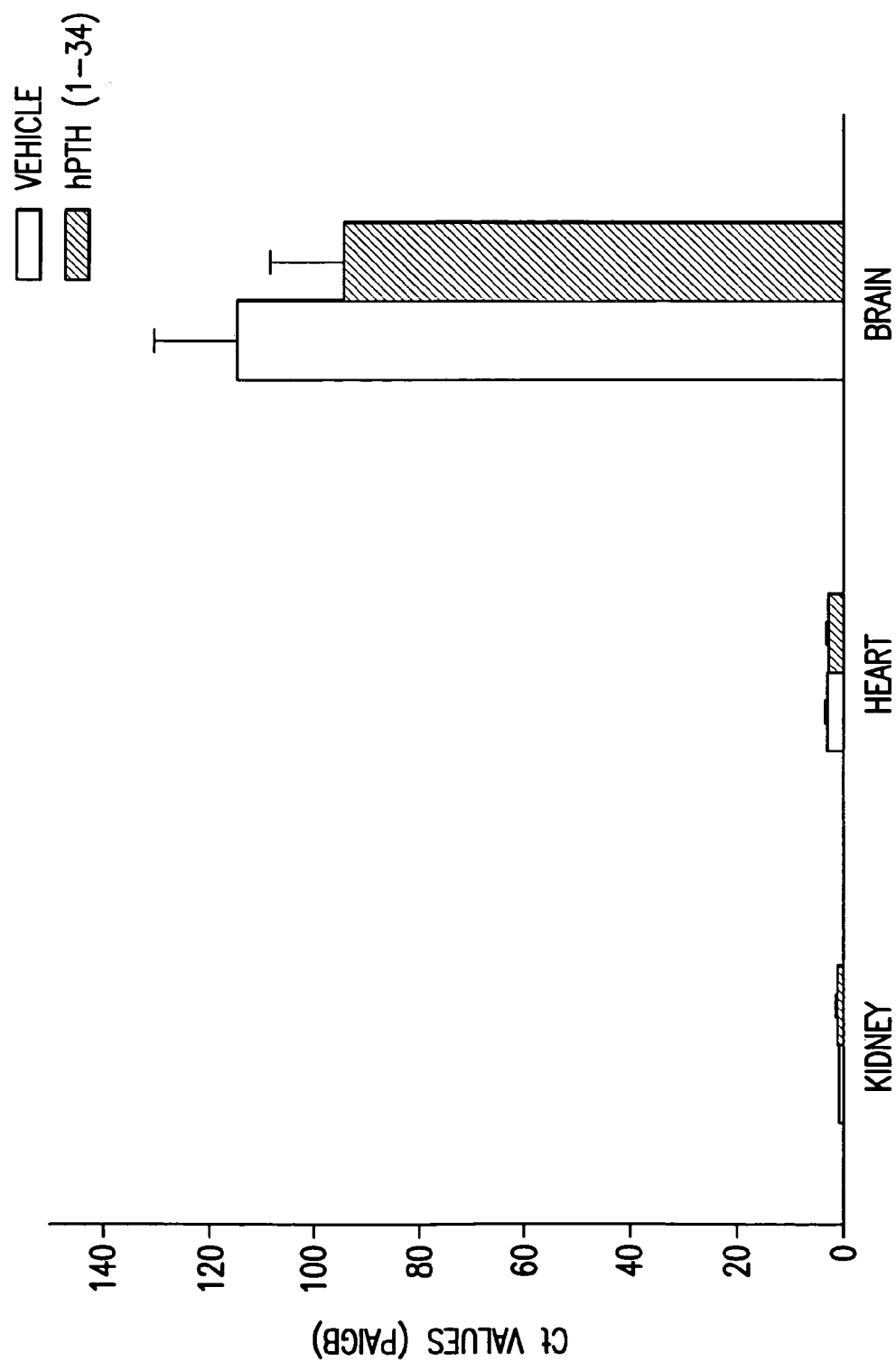
FIG. 8 shows the lack of regulation of PAIGB expression by PTH 1-34 in non-bone tissues (referred to in Example 8).

Effect of Intermittent PTH Injection on Expression of PAIGB in Different Tissues In order to examine whether observed increased expression of PAIGB in bone after intermittent PTH administration is seen in brain, kidney and heart, tissues where PAIGB expression is also observed we performed real time PCR analysis on RNA from these tissues. As seen on FIG. 8, intermittent injection of PTH did not produce any changes in PAIGB expression in tested tissues, indicating that effect of PTH on PAIGB expression is bone specific.

Example 9

Figure 9:
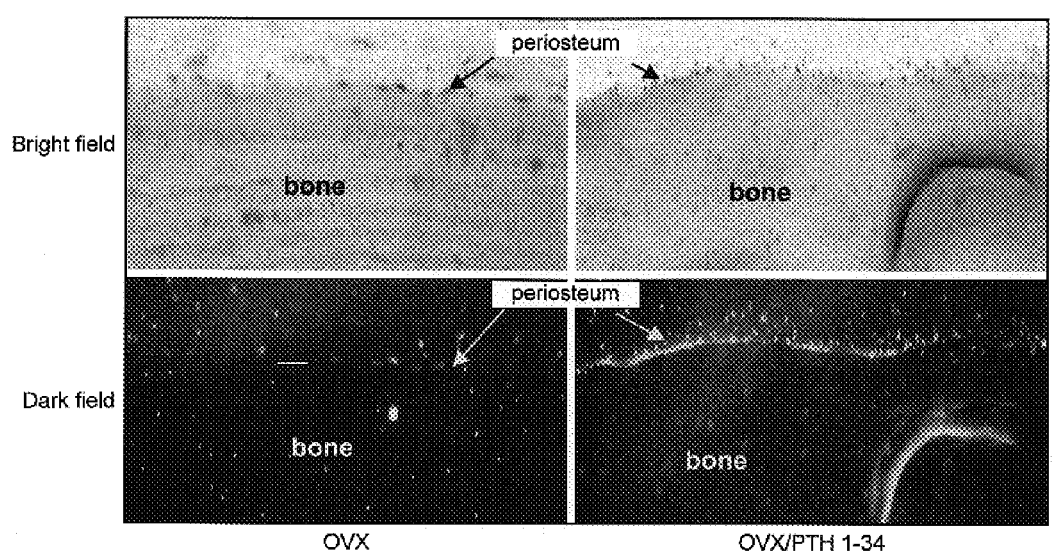
FIG. 9 shows the induction of PAIGB expression with PTH 1-34 by in situ hybridization analysis in mouse calvariae (referred to in Example 9).

Examination of PAIGB Expression in Calvariae Pre- and Post-PTH Treatment—In Situ Hybridization In situ analysis of PAIGB mRNA expression can be assessed in various animal species including human bone biopsy samples or from mouse, rat, dog bone samples etc., that have been treated with bone forming agents. Swiss Webster mice that have been treated with 100 μg/kg/day PTH 1-34 subcutaneously or 30 days. Mouse calvariae were gently dissected and fixed in 4% paraformaldehyde. Following fixation, the bones were decalcified in TBD-2 decalcifying agent (Shandon Lipshaw, Pittsburgh, Pa.) for 7-8 hrs then dehydrated in graded alcohol. The calvariae was subsequently bisected perpendicular to the sagittal suture through the central portion of the parietal bones parallel to the lambdoidal and coronal sutures and embedded in paraffin (femur and tibia samples are embedded longitudinally in paraffin). Four to six 5 μm-thick representative, non-consecutive step sections were cut for further analysis. Selected sections were stained with hematoxylin and eosin (Shandon Lipshaw, Pittsburgh, Pa.) and adjacent section were used for in situ hybridization. The probe for in situ hybridization was generated by subcloning a fragment of the mouse PAIGB sequence (398 bp product) (SEQ ID NO: 40) from the pCR-Blunt II-TOPO plasmid (Invitrogen) by digesting with ECORI and ligating into the pBluescript II SK plasmid (Stragene). The Sal I site was used to linearize the plasmid for subsequent generation of the antisense and sense probes using 0.5 mCi of $^{35}S$ labeled α-UTP with the T3 and T7 RNA polymerase (Boehringer Mannheim) respectively. The sections were hybridized using a probe concentration of $3 \times 10^4$ cpm/μl. After stringent washes, the sections were processed for standard autoradiography. The expression of mRNA are evaluated using a Nikon microscope with either bright or dark field. As demonstrated by the bright and dark field images, there was little to no expression of PAIGB in clayeriae of OVX mice where as PAIGB was induced in osteoblastic cells adjacent to the bone surface in the periosteum in PTH treated mice (FIG. 9).

Example 10

Figure 10A:
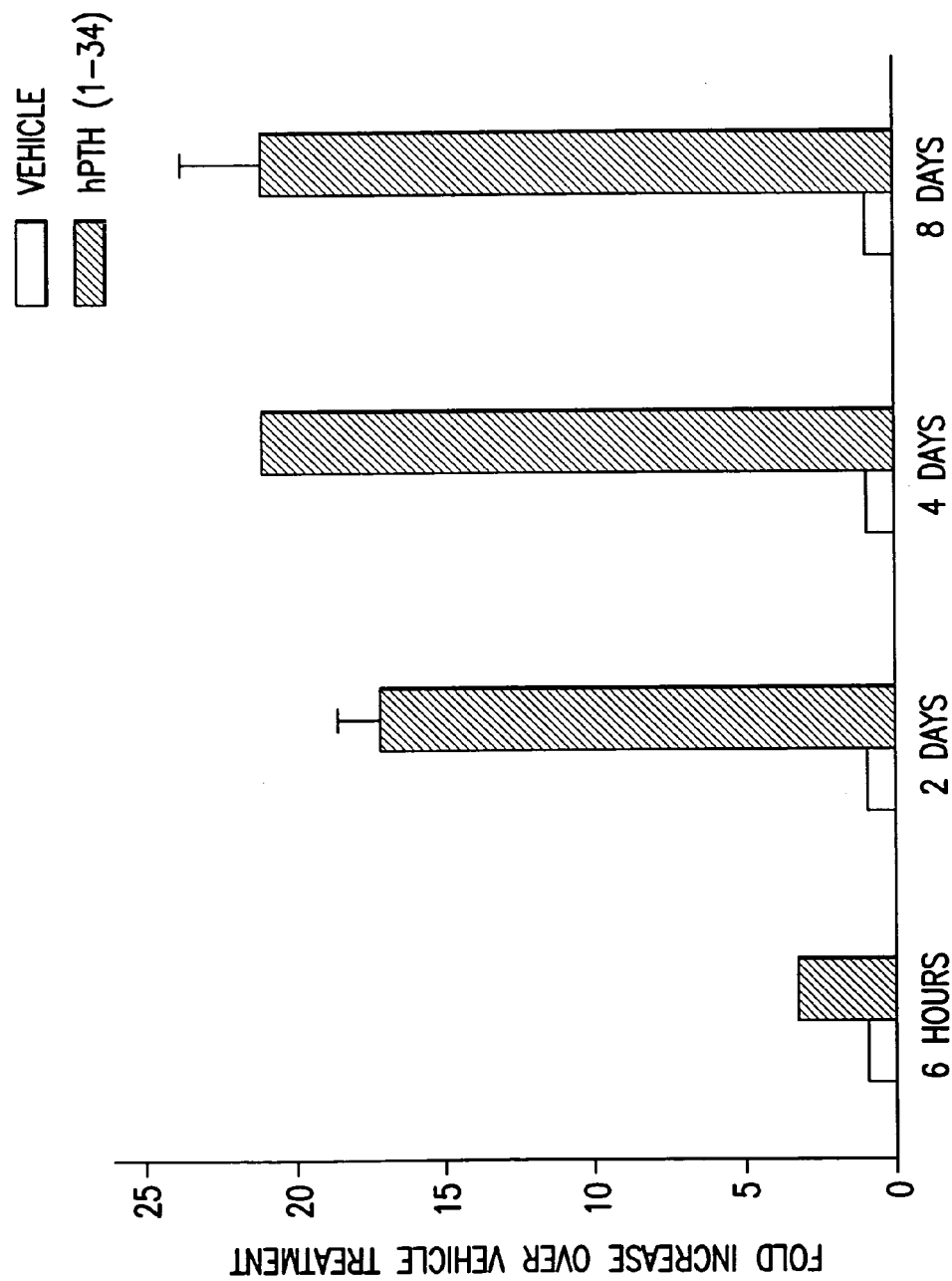
FIG. 10A shows the time course of PAIGB expression in rat tibia during intermittent PTH 1-34 treatment (referred to in Example 10).

Time Course of PAIGB Expression in Bone During Intermittent PTH Adminstration in Rat The initial experiments measured the expression of PAIGB in the rat tibia after 8 days of treatment. In order to examine the time course of PTH action on PAIGB expression, experiments were performed on rats treated with intermittent PTH injections (40 μg/kg body weight) and tibias were collected for RNA isolation as well as evaluation in BMD changes. Time points of sample collection were 6 hours, 2 days, 4 days and 8 days after intermittent PTH treatment. Real time PCR analysis was performed on isolated RNA samples using above described primers. Data shown on FIG. 10A show that ~20-fold increase of PAIGB was observed after two days treatment with PTH. The effects of PTH at the same magnitude were also observed at days 4 and 8 after PTH treatment.

Figure 10B:
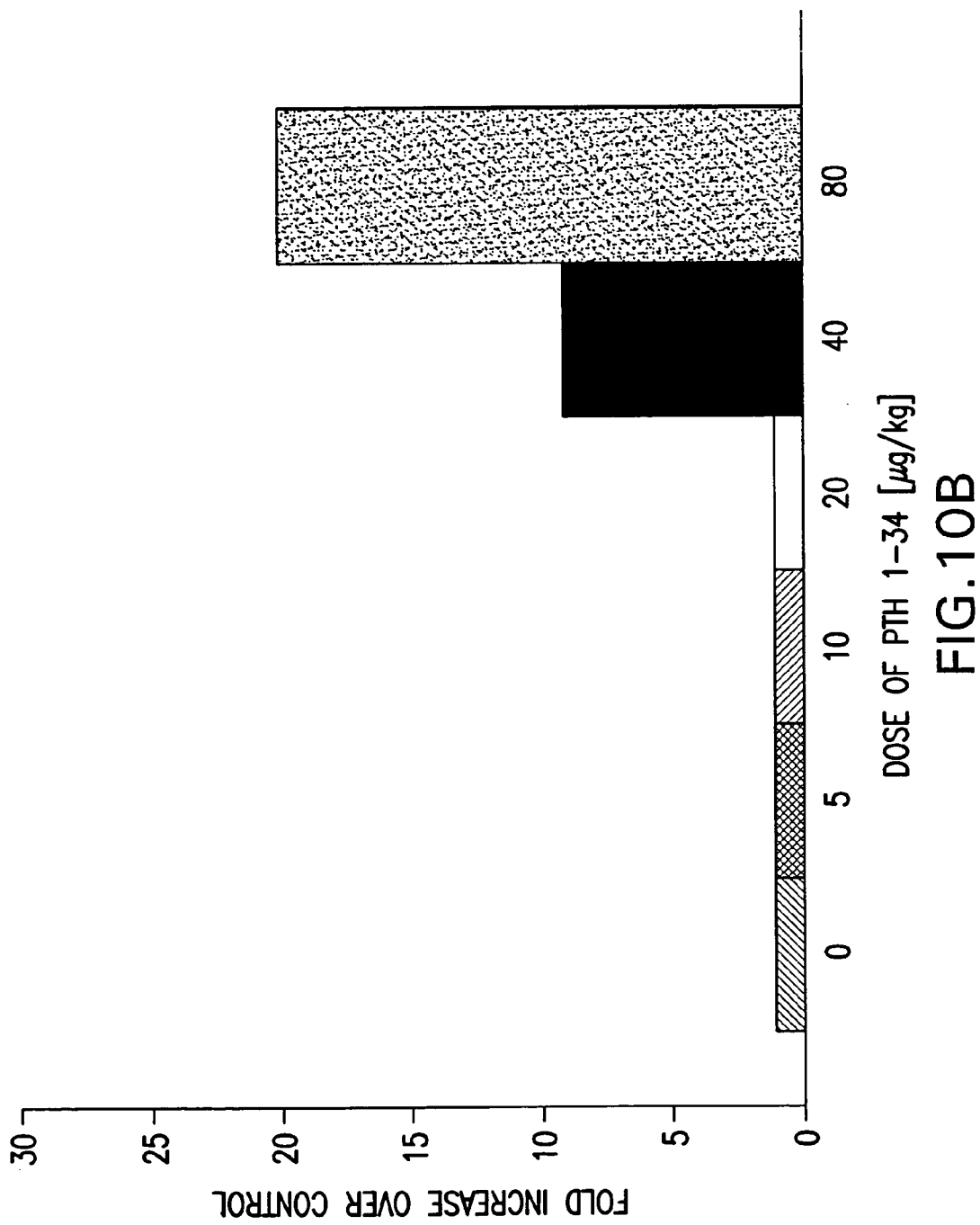
FIG. 10B shows that the regulation of PAIGB expression by sc administration of PTH 1-34 in rat tibia is dose dependent (referred to in Example 10).

The observed increase in PAIGB expression in bone treated with PTH is dose-dependent (FIG. 10B). OVX rats with established osteopenia were treated with increasing concentration of human PTH (1-34): 5, 10, 20, 40 and 80 μg/kg of body weight for 8 days with one daily injection. Six hours after last injection animals were scarified and bone samples were harvested for RNA isolation as described in Experimental Procedure section. Real time PCR analysis of PAIGB expression indicated that low doses of PTH 5, 10 and 20 μg/kg did not have any effect on PAIGB expression while 40 and 80 μg/kg led to 10 and 20 fold increase respectively. These data are in good correlation with published reports regarding doses of PTH that induced bone formation (anabolic PTH effects).

Example 11

Expression of PAIGB in Bone

In order to examine whether changes in PAIGB expression with intermittent PTH treatment correlates with effects of PTH on bone, samples from rats treated with PTH for 2, 4 and 8 days were subjected to BMD measurements for both total and trabecular bone (trabecular density of proximal tibia was measured). Two days PTH treatment increases expression of PAIGB. At the same time point significant increase in trabecular BMD (Δ trabecular density: 6.98+/−17.90 with PTH treatment vs −27.1+/−9.27 with vehicle treatment) was detected without any significant changes in total BMD (Δ total density: −9.15+/−2.94 PTH vs 0.69+/−4.10 vehicle) (Table 1).

After 4 days of intermittent PTH injection expression of PAIGB was 20 fold over vehicle treated rats. Total body and trabecular BMD was measured at the same time point. PTH induced significant increase in both total BMD (10.56+/−3.11 PTH vs −2.95+/−2.20 vehicle) and trabecular BMD (8.70+/−9.98 for PTH vs −20.8+/−6.62 for vehicle) (Table 2). Expression of PAIGB in bone correlated well with the changes in BMD observed after 2 and 4 days of intermittent treatment of PTH (Table 1 and Table 2).

TABLE 1

Effects of Two Days Treatment with hPTH (1–34) on the Total and Trabecular Density of the Proximal Tibia in Ovariectomized Rats with Established Osteopenia

| Treatment | N | ΔTotal Density[a] | N | ΔTrabecular Density |
|---|---|---|---|---|
| Vechicle, sc (0.1% BSA: 0.01% ascorbic acid (AA)) | 7 | 0.69 ± 4.10 | 8 | −27.10 ± 9.27 |
| HPTH (1–34) 40 μg/kg, sc | 8 | −9.15 ± 2.94 | 8 | 6.98 ± 17.90 |

[a]Mean (mg/cm$^3$) +/− SEM

TABLE 2

Effects of Four Days Treatment with hPTH (1–34) on the Total and Trabecular Density of Proximal Tibia in Ovariectomized Rats with Established Osteopenia

| Treatment | N | ΔTotal Density[a] | N | ΔTrabecular Density |
|---|---|---|---|---|
| Vechicle, sc (0.1% BSA: 0.01% AA) | 8 | −2.95 ± 2.20 | 8 | −20.80 ± 6.62 |
| HPTH (1–34) 40 μg/kg, sc | 8 | −10.56 ± 3.11* | 8 | 8.70 ± 9.98* |

[a]Mean (mg/cm$^3$) +/− SEM
*p < 0.05 vs corresponding Vehicle value
**p < 0.01 vs corresponding Vehicle value

Example 12

PTH Treatament of ROS 17/2.8 Cells

Figure 11A:
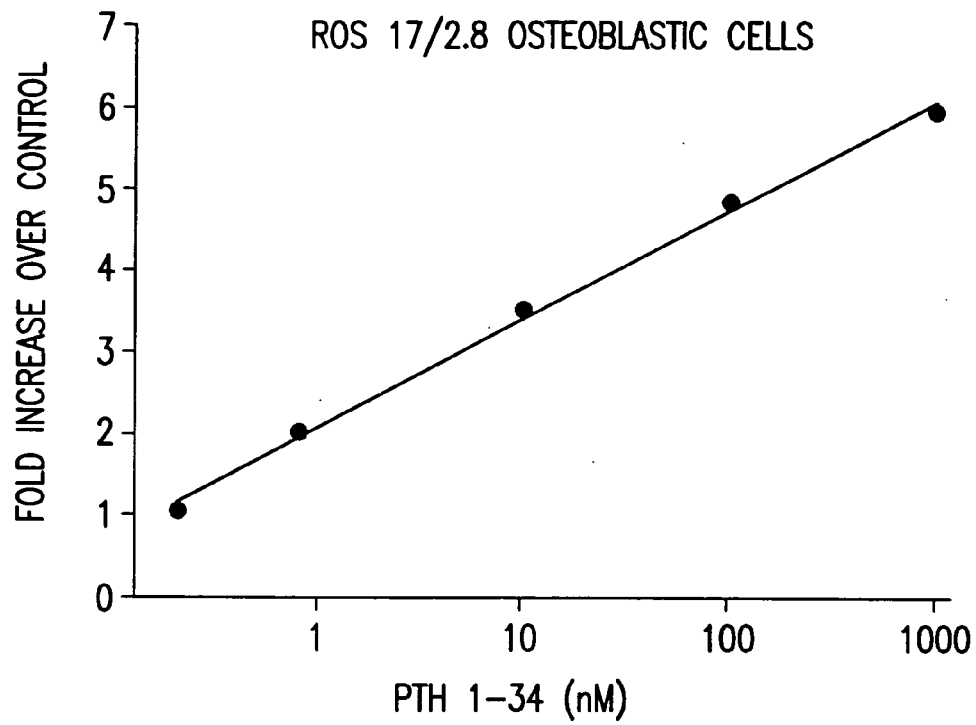
FIG. 11A shows that the regulation of PAIGB expression by PTH 1-34 is dose dependent in ROS 17/2.8 osteoblastic cells (referred to in Example 12).

ROS 17/2.8 rat osteoblast cell line that express PTH receptor (~80000 receptors/cell) were treated with increased doses of PTH: 1 nM, 10 nM, 100 nM and 1000 nM. Real time PCR using rat specific Taq-man probes and primers were used to examine the changes in PAIGB expression with PTH treatment. Increasing concentrations of PTH induced dose-dependent increase in PAIGB massage as shown on FIG. 11A.

Figure 11B:
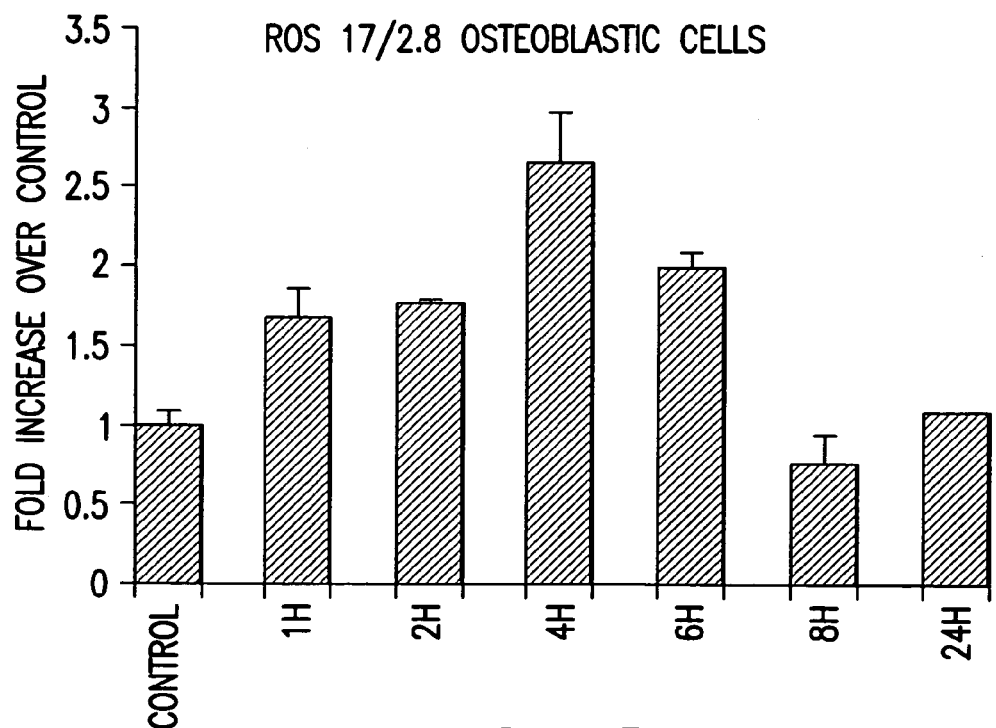
FIG. 11B shows the time course of PAIGB induction by PTH 1-34 in ROS 17/2.8 osteoblastic cells (referred to in Example 12).

Time course of PTH induction of PAIGB expression was examined. ROS 17/2.8_cells were treated with 10 nM PTH and RNA was harvested at 1, 2, 4, 6, 8 and 24 hours post treatment. The maximal increase of PAIGB expression was at 4 hours time point (2.66+/−0.3). The effect of PTH on PAIGB expression was completely abolished 8 hours post treatment (FIG. 11B).

Example 13

Signaling Pathway Involved in Regulation of PAIGB Expression by PTH

Figure 12:
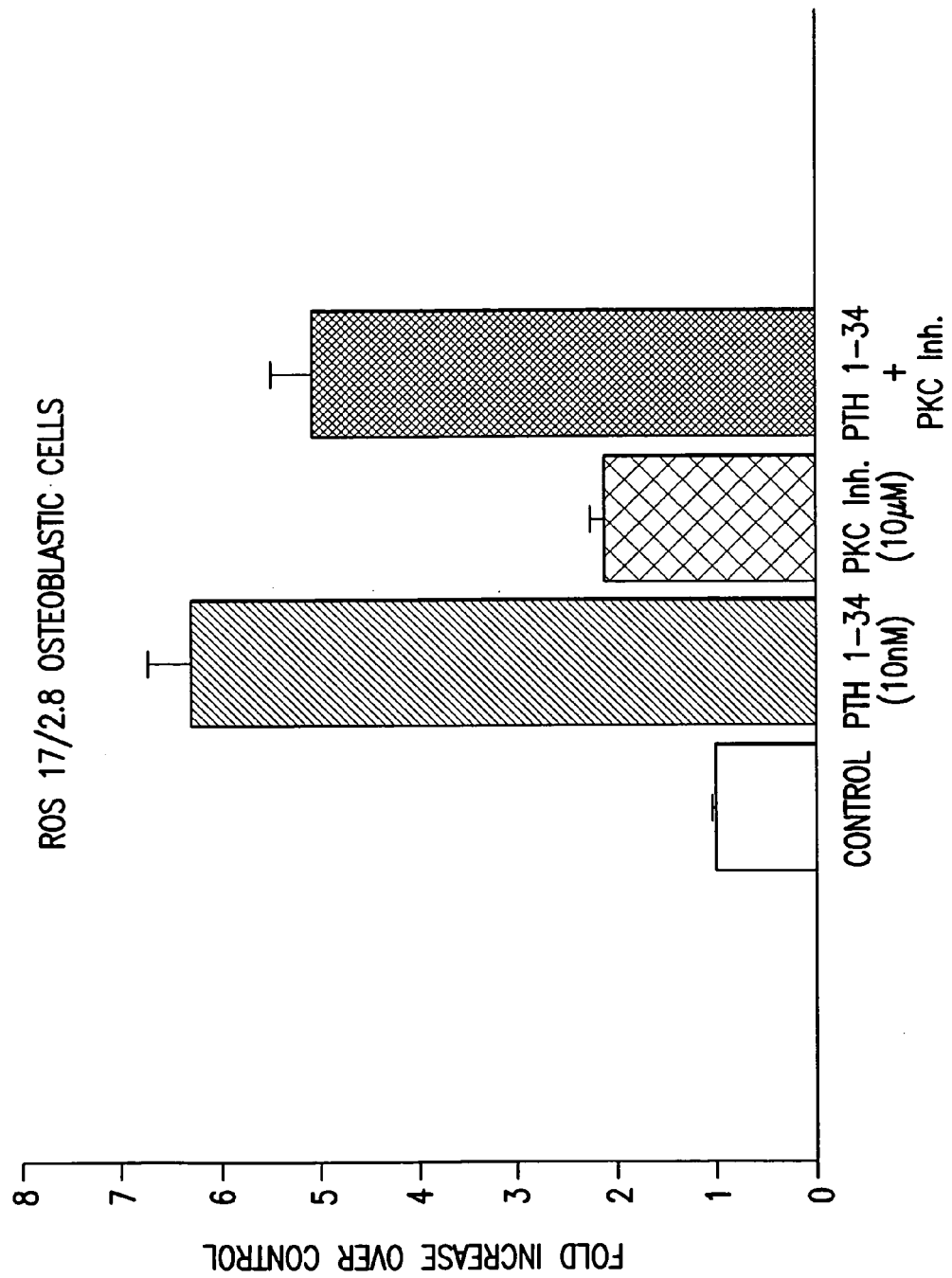
FIG. 12 shows that the Protein Kinase C (PKC) pathway is not involved in the regulation of PAIGB by PTH 1-34 (referred to in Example 13).
Figure 13:
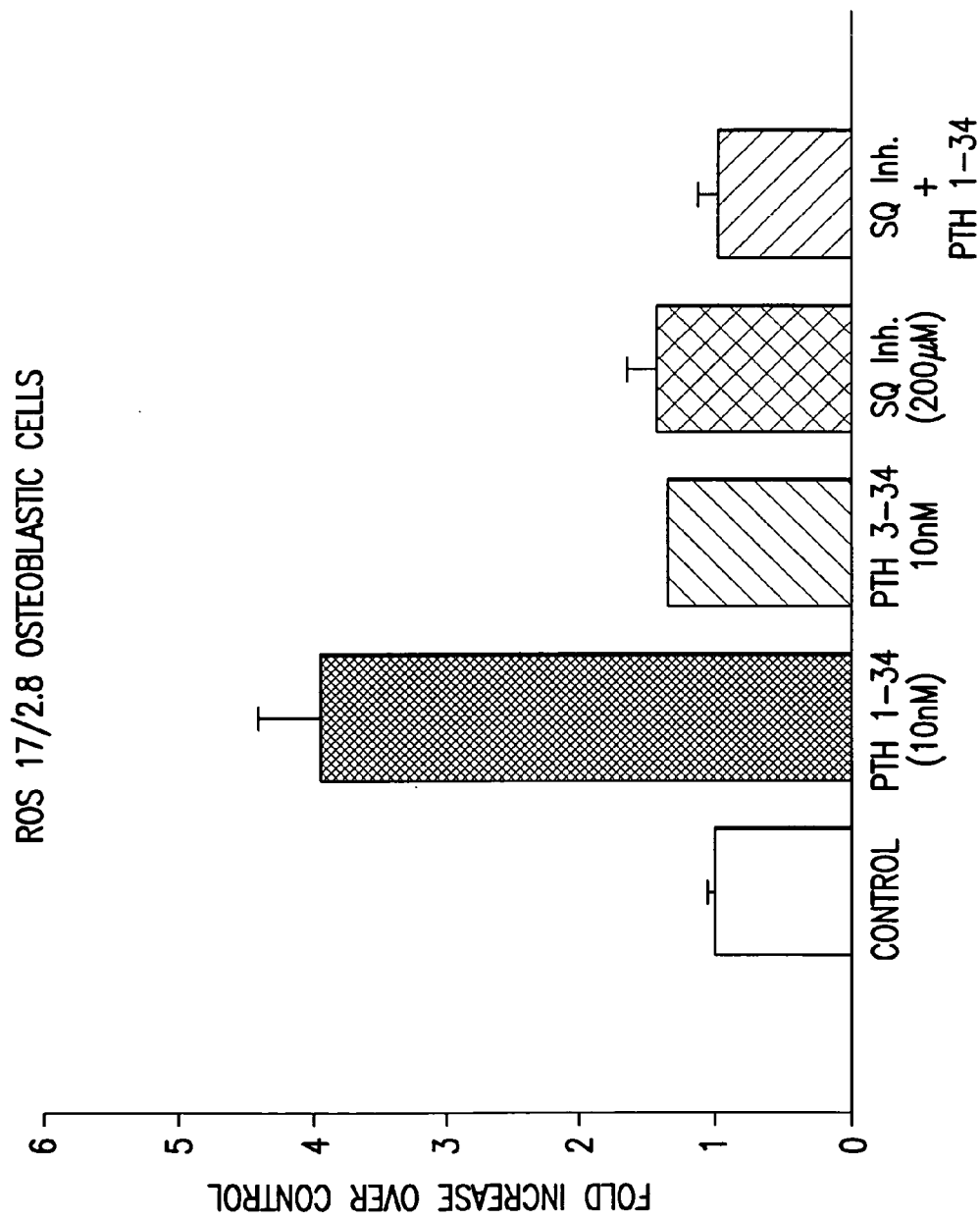
FIG. 13 shows that PTH 1-34 exerts its effects on PAIGB expression through adenylate cyclase and cAMP signaling in ROS 17/2.8 cells (referred to in Example 13).

In order to examine the signaling pathway involved in regulation of PAIGB expression by PTH, Applicants utilized ROS 17/2.8 cells that were treated with 10 nM PTH in the presence or absence of SQ 22536 (Calbiochem La Jolla, Calif.) an adenylate cyclase inhibitor and the Protein Kinase C inhibitor (PKC)19-27, an inhibitor of PKC signaling pathway. The cells were pretreated for 2 hours with 200 µM SQ 22536 and 10 µM PKC inhibitor and treated for 4 hours with PTH. Real time PCR was used to detect the changes in PAIGB expression under this condition. The data shown on FIGS. 12 and 13 with the PCK inhibitor and SQ22536 shows that PTH exerts its effect on PAIGB expression by activating cAMP signaling pathway since The PKC inhibitor had little to no effect in blocking PTH induced PAIGB (FIG. 12). In addition, pre-incubation with SQ 22536 compound completely blocks the effect of PTH on PAIGB (FIG. 13). These data are consistent with the effects of PTH 3-34 which has minimal to no effect on adenylate cyclase activation.

Applicants showed that the PTH induction of PAIGB expression is PTH receptor specific since an agonist (isoproterenol) of another G-coupled protein receptor (the β-adrenergic receptor) only exerted a 2 fold increase in PAIGB expression when compared to 6 fold induction with 10 nM PTH (data not shown). Increases in PAIGB expression were also observed in ROS 17/2.8 and UMR 106 osteoblastic cells with Forskolin and the phosphodiesterase IV inhibitor Rolipram (data not shown), suggesting that the increase in PAIGB expression observed by these agents may be due to increases in cAMP levels in cells. Collectively, the results suggested that the Effect of PTH on PAIGB expression is mediated via cAMP but not via PKC.

Example 14

Effects of Bone Forming Agents on PAIGB Expression

In order to examine whether increased PAIGB expression is a direct result of PTH activity or consequence of induction of bone formation, different anabolic agents were tested in ROS cells. ROS cells were treated with: estrogen (10 nM), estrogen in combination with PTH, tamoxifen (0.1 µM) alone and in combination with PTH, calcitonin (5 ng/ml), prostaglandin $E_2$ (PGE$_2$) (using two concentrations 10 nM and 10 µM) and dexamethasone (100 nM). The cells were treated for 4 hours and RNA was isolated for real time PCR analysis. In addition, ROS cells were treated with BMP2 (bone morphogenic protein 2) (300 ng/ml). The treatment with BMP 2 was for 4 and 24 hours. Total cellular RNA was isolated from treated cell line using Trizol (Invitrogen, Carlsbad, Calif.). Contaminating genomic DNA was removed by DNase treatment (Qiagen RNase-Free Dnase, Valencia, Calif.) and the RNA was subsequently cleaned using the Qiagen RNeasy kit as described by the manufacturer. TaqMan analysis of samples was performed as described in General Method section. Agents which induced PAIGB mRNA expression was analyzed.

Figure 14:
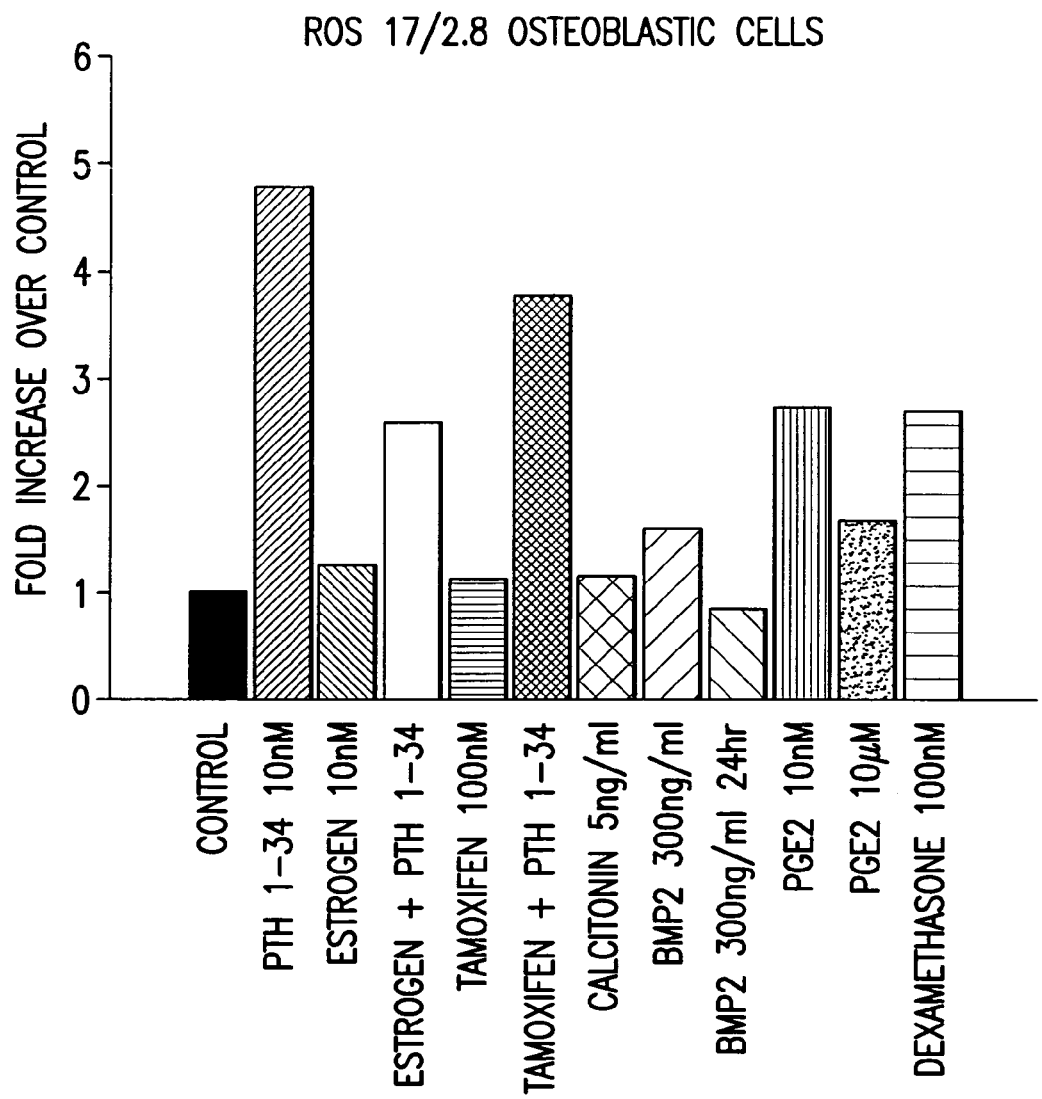
FIG. 14 shows the effect of other bone related agents on PAIGB expression in ROS 17/2.8 cells (referred to in Example 14).
Figure 15:
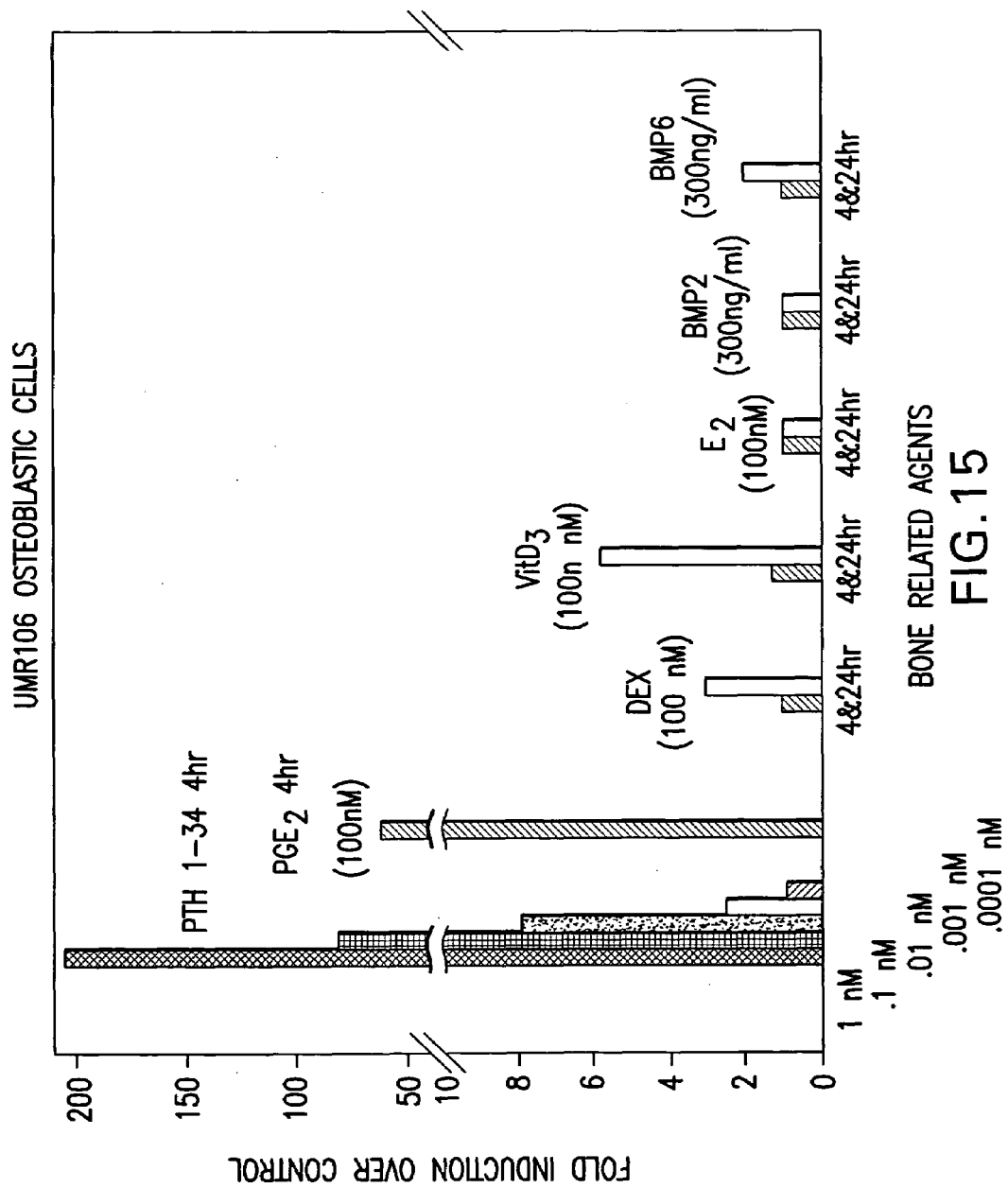
FIG. 15 shows the effect of other bone related agents on PAIGB expression in UMR106 cells (referred to in Example 14).

Estrogen, tamoxifen, BMP2 (bone morphogenetic protein 2) and calcitonin did not have any effect on PAIGB expression after 4 hours of treatment (FIG. 14). BMP 2 did not induce PAIGB expression even after 24 hours of treatment. $PGE_2$ induced PAIGB mRNA expression only at the lower dose of $PGE_2$. In addition, dexamethasone treatment led to 2-3-fold increase in PAIGB expression. Similar responses in the bone related agents that were tested were also observed in UMR106 cells (FIG. 15). However, the magnitude of these responses were more robust in UMR106 cells compared to the ROS 17/2.8 cells. In addition, in UMR106 cells vitamin $D_3$ (VitD3) and to a lesser extent BMP6 induced PAIGB expression. $PGE_2$, Vitamin $D_3$ and dexamethasone are known to induce accumulation of cAMP which could explain why PAIGB expression is induced by these agents. Collectively, these data strongly suggest that PAIGB induction is preferentially mediated by the anabolic effects of PTH on osteoblastic cells since other known anabolic agents had significantly less effects on PAIGB expression.

Example 15

Induction of PAIGB Expression by PTH 1-34 in Human U2OS Osteoblastic Cells

Figure 16A:
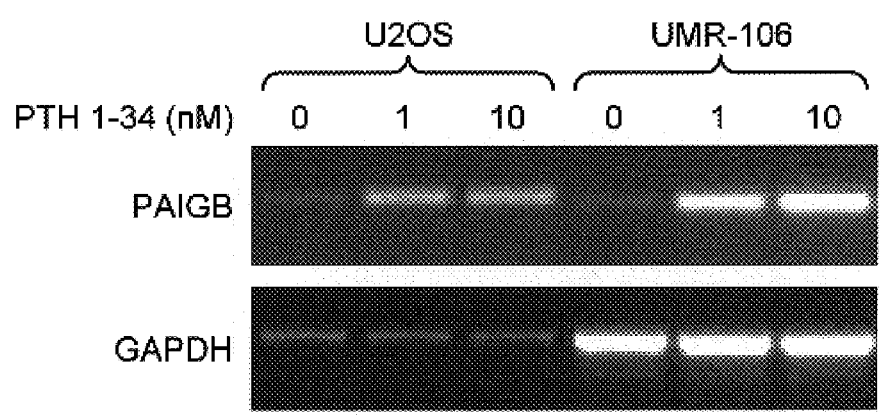
FIG. 16A shows the induction of PAIGB expression by PTH 1-34 in human U2OS and rat UMR osteoblastic cells by RT-PCR (referred to in Example 15).
Figure 16B:
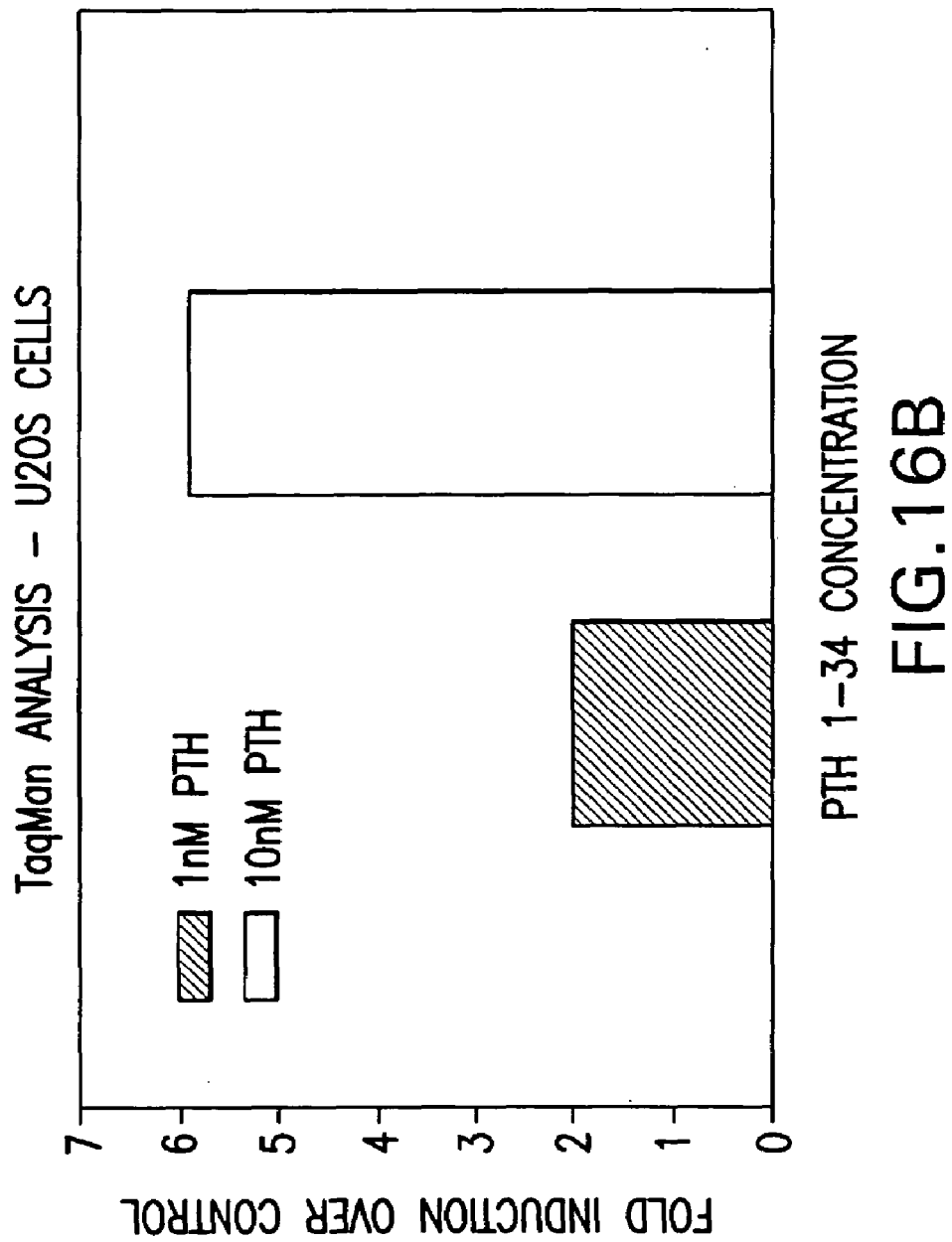
FIG. 16B shows the induction of PAIGB expression by PTH 1-34 in human U2OS osteoblastic cells by TaqMan anaysis (referred to in Example 15).

The human osteoblastic U2OS cells and the rat UMR106 cells were treated with 1 or 10 nM PTH 1-34. RT-PCR analysis using primers to exon 2 of human (SEQ ID NO:41 and 42) and rat PAIGB (SEQ ID NO:43, 44) showed induction of PAIGB expression in human osteoblastic U2OS cells compared to the control UMR106 rat osteoblastic cells (FIG. 16A). FIG. 16B demonstrates the induction of PAIGB expression in U2OS cells as measured by real time PCR. These results show that PTH 1-34 can induce PAIGB expression in human osteoblastic cells.

Example 16

Identification of Agents Which Induce PAIGB mRNA

A high through-put screen for agents which can induce the expression of PAIGB mRNA involves treating cells of the mesenchymal lineage. These cells can be undifferentiated stem cell, preosteoblast or mature osteoblast with either a small molecular compound (typically 10-30 uM), natural product or peptide based compounds. The cells are treated in growth media containing 10% FBS for 4 to 18 hr. The media is removed and the cells are washed with PBS followed by the isolation of total RNA using an automated RNA extraction instrument (e.g., Applied Biosystems PRISM 6700). Typical yields of RNA from $1 \times 10^6$ cells is 20 ug total RNA.

Following RNA isolation, approximately 100 ng of RNA will be analyzed by real time PCR (TaqMan analysis) as described in general methods.

Example 17

Figure 17:
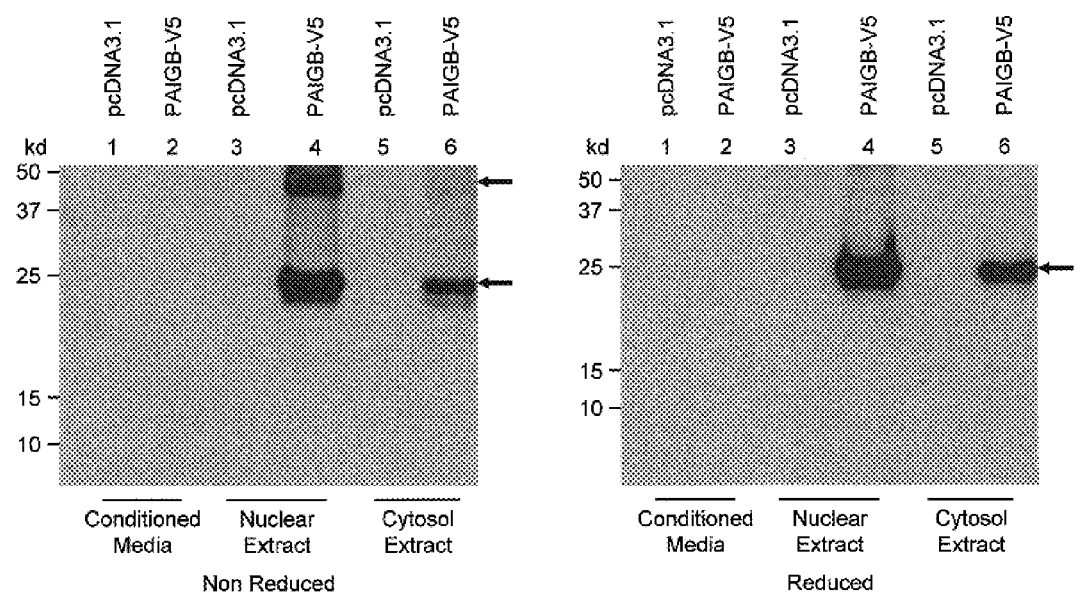
FIG. 17 shows protein expression of PAIGB in human U2OS osteoblastic cells (referred to in Example 17).
Figure 18:
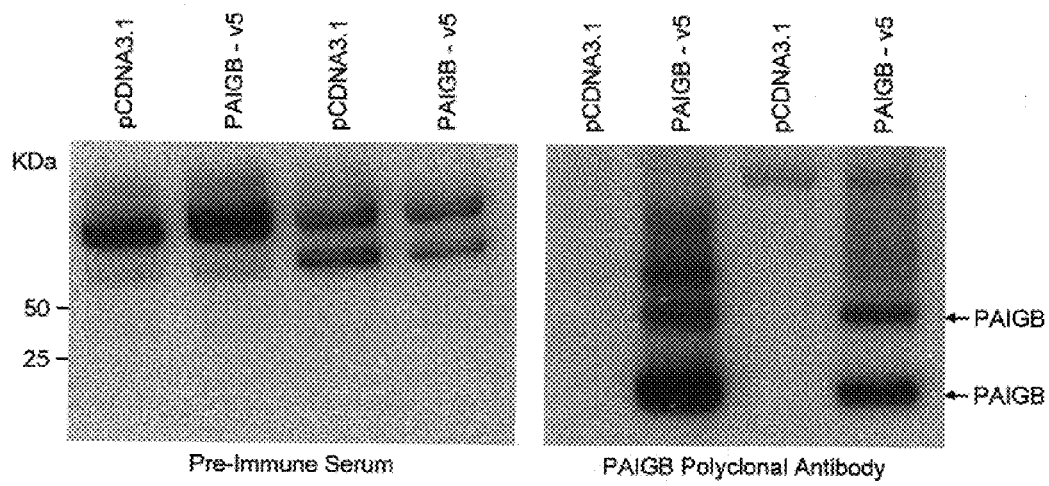
FIG. 18 shows the ability of a PAIGB rabbit polyclonal antibody to detect PAIGB protein expressed in U2OS cells (referred to in Example 17).

PAIGB Protein Expression and use of Antibodies to Detect its Expression Osteogenic or Bone Anabolic Activity The Western Blot in FIG. 17 represents the expression of full length (exons 1,2,3) PAIGB-v5 protein tagged in U2OS osteoblastic cells as demonstrated by immunoblotting with a v5 monoclonal antibody (Invitrogen). The ability of the PAIGB polyclonal antibody to detect PAIGB protein was demonstrated in FIG. 18. FIG. 18 represents a Western Blot of nuclear and cytoplasmic extracts that were obtained from U2OS cells transfected with the human PAIGB ORF (designated full length containing exons 1, 2, 3, SEQ ID NO:3). Lanes 2, 4, 6 and 8 were extracts for the PAIGB transfected cells and lanes 1, 3, 5 and 7 were extracts from control plasmid cells. Lanes 1, 2, 5 and 6 were cytoplasmic extracts while lanes 3, 4, 7 and 8 were nuclear extracts. Lanes 5-8 which were immunoblotted with the PAIGB polyclonal antibody (raised against SEQ ID NO:11) show specific reactivity to PAIGB as indicated in lanes 6 and 8 and arrows. Lanes 1-4 were immunoblotted with pre-immune serum as a negative control. Specifically, in FIGS. 17 and 18, U2OS cells were seeded at $3.1 \times 10^6$ cells in 100 mm dishes and were transfected 24 hrs later with Lipofectamine 2000 (Invitrogen) using 10 µg of the human PAIGB ORF or control vector (pcDNA3.1-v5 tagged, Invitrogen) diluted in OptiMEM (Invitrogen). The conditioned media was collected and the cytoplasmic and nuclear extracts were obtained as previously described (Henry B. Sadowski and Michael Z. Gilman. Nature. 362: 79-83. 1993.) Briefly, cold hypotonic buffer (20 mM HEPES pH 7.9, 20 mM NaF, 1 mM $NaH_2PO_4$, 1 mM EDTA, 1 mM EGTA, 1 mM dithiothreitol, 0.5 mM phenylmethylsulphonyl fluoride and mammalian protease inhibitor cocktail (Sigma cat. 8340)) with 0.2% NP40 was added to the dishes to lyse the cells. The samples were centrifuged at 16,000×g for 20 sec to pellet the nuclei. A volume of 5 M NaCl was added to the supernatant to yield a final concentration of 120 mM NaCl. The sample was then centrifuged for 20 min at 16,000×g and glycerol (final concentration of 10% v/v) was added to the supernatant. The nuclear pellet portion of the sample was resuspended in hypertonic buffer (hypotonic buffer containing 420 mM NaCl and 20% glycerol) in 0.2% Nonidet P 40 (NP40) (Sigma, St. Louis, Mo.). The pellets were incubated in the hypertonic buffer for 30 min at 4 C, centrifuged at 16,000×g for 20 min and the supernatant was collected. The Western Blot Analysis was performed by running 14 µg total protein per lane on a 12% Bis Tris SDS-PAGE (Invitrogen) and then subsequently transferring the proteins to nitrocellulose (Invitrogen). Immunoblotting was performed with the anti-rabbit Western Breeze kit (as described by the manufacturer, Invitrogen) using 1:1000 dilution of the v5 monoclonal antibody or 5 µg/ml purified PAIGB rabbit polyclonal antibodies.

Example 18

Figure 19:
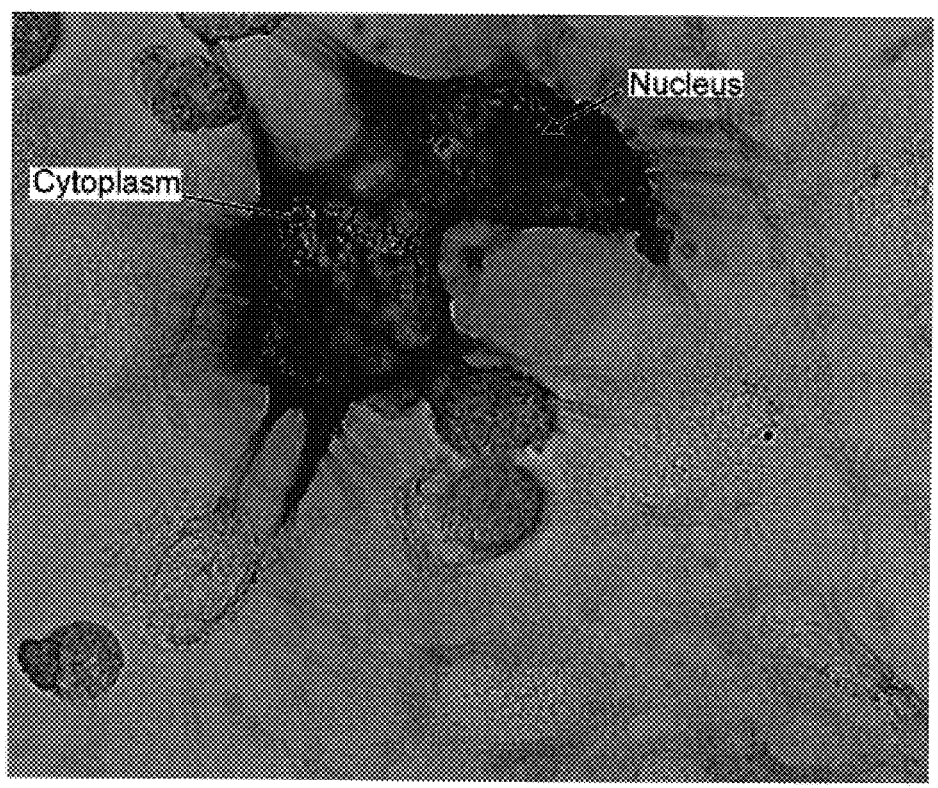
FIG. 19 shows the ability to use PAIGB polyclonal antibodies to detect PAIGB protein expression by immunohistochemical analysis in U2OS cells (referred to in Example 18).

Analysis of PAIGB Protein Expression by Immunohistochemical Method Immunofluorescence Microscopy and Flow Cytometry For Immunohistochemical analysis of PAIGB protein expression, (FIG. 19) cells were seeded at $2 \times 10^4$ to $5 \times 10^4$ cells in Labtek 2 or Labtek 8 well chamber slides (Nunc) and were grown overnight in growth media. The media was aspirated and fresh media was added followed by transient transfection with PAIGB cDNA with commercially available reagents as described in Example 17. Following 24-48 hr incubation the cells were washed 3 times with cold TBS (Tris Buffered Saline) and were subsequently fixed with cold methanol for 30 min. The samples were air dried for 5-10 min at room temperature and then rinsed 3 times with TBS. The samples were blocked with Vectastain (Vector Laboratories, Burlingame, Calif.) ABC-AP blocking serum in TBS for 20 min at room temperature and then rinsed in TBS containing 1% BSA. Samples were then incubated with 2.5 µg/ml primary antibody diluted in DAKO antibody diluent (DAKO Corp. Carpinteria, Calif.) for 30 min at room temperature. The samples were subsequently washed 3 times in TBS and incubated with diluted biotinylated secondary antibody (Vector Laboratories) for 30 minutes and then washed in TBS. The samples were then incubated for 30 min in Vectastain (Vector Laboratories, Burlingame, Calif.) ABC-AP reagent as described by the manufacturer. The samples were then washed with TBS and staining was observed by incubating samples with an alkaline phosphosphatase substrate (Vector Laboratories, Burlingame, Calif.) as described by the manufacturer.

Example 19

Methods for In Vivo Immnunohistochemistry

Figure 20:
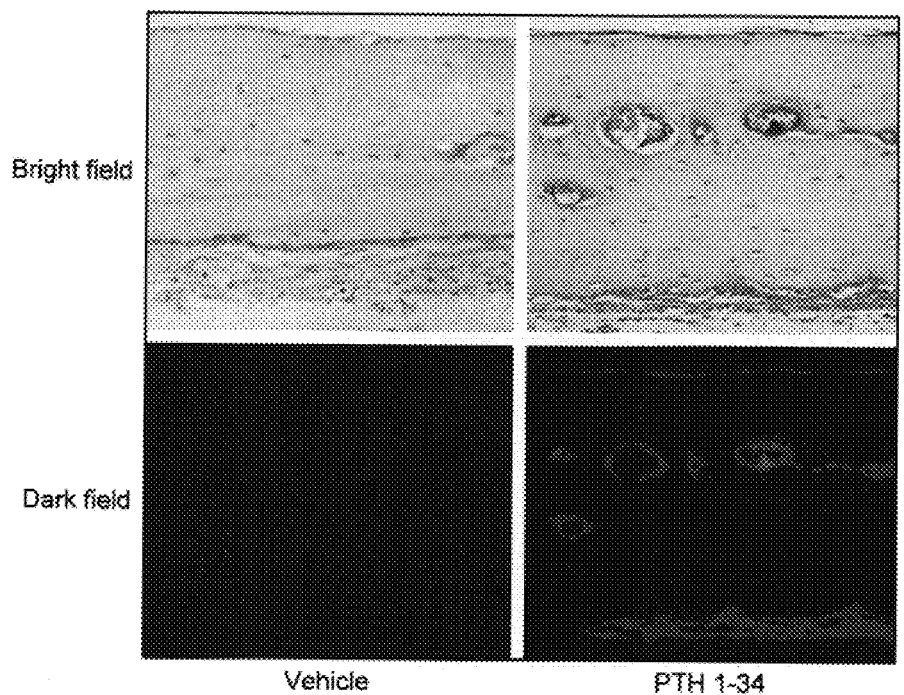
FIG. 20 shows induction of PAIGB protein in the periosteum and endosteum of mouse calvariae treated with PTH 1-34 (referred to in Example 19).
Figure 21:
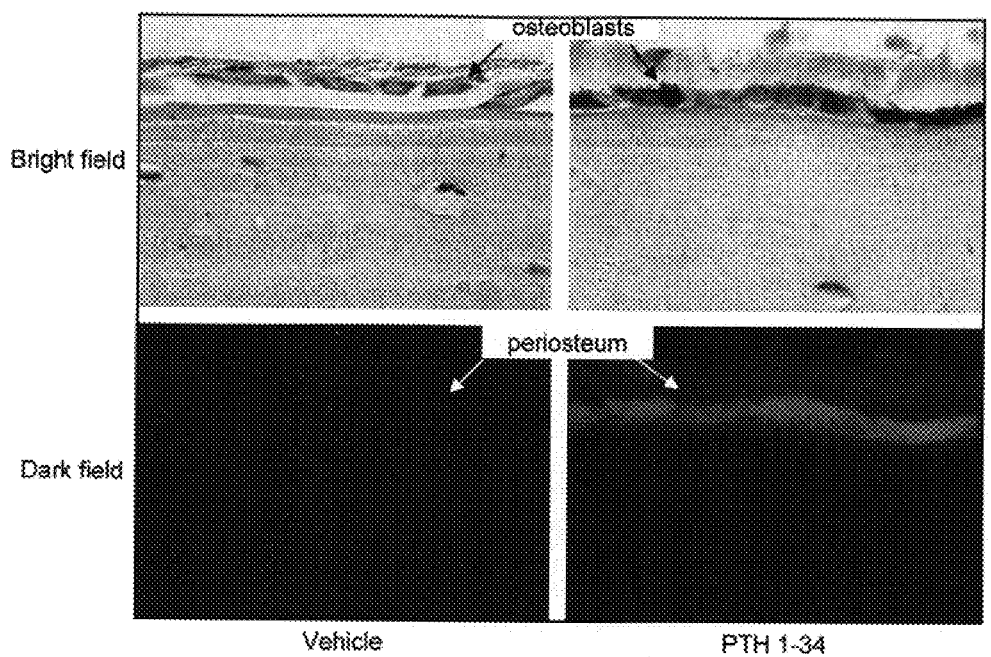
FIG. 21 shows induction of PAIGB protein in osteoblasts of the periosteum from mouse calvariae treated with PTH 1-34 (referred to in Example 19).
Figure 22:
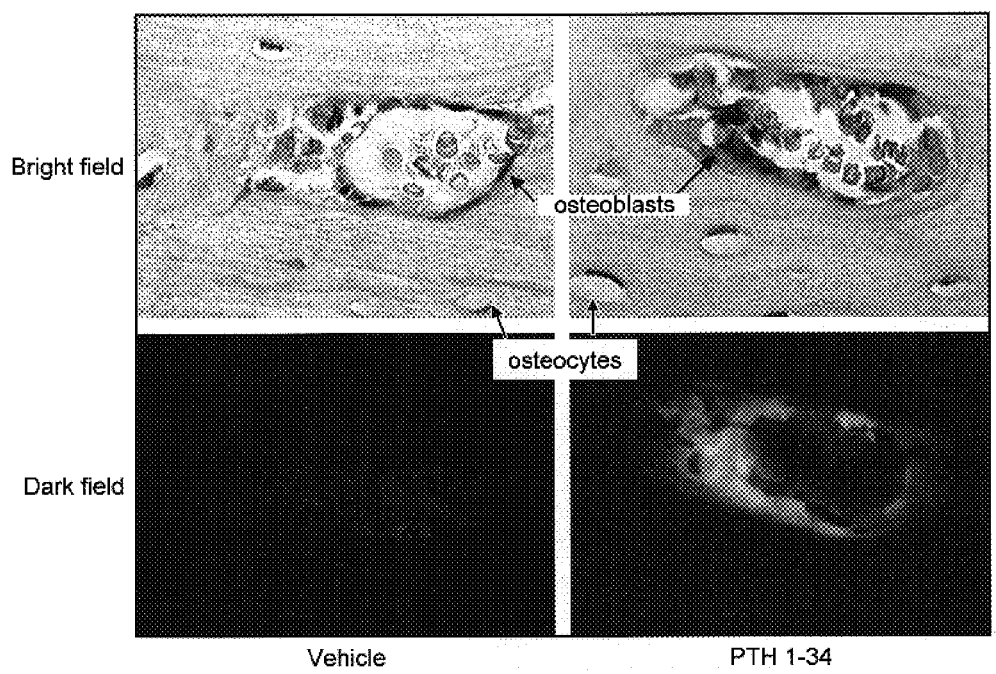
FIG. 22 shows induction of PAIGB protein in osteoblasts of the endosteum from mouse calvariae treated with PTH 1-34 (referred to in Example 19).

Immunohistochemical analysis of PAIGB protein express can be assessed in various animal species such as human bone biopsy samples, mouse, rat, or dog bone samples etc., that have been treated with potential bone anabolic agents. For example, Swiss Webster mice were treated with 20 µg/kg/day PTH 1-34 subcutaneously onto the calvariae for 18 days. Following the 18 days, the calvariae samples were harvested and PAIGB protein expression was analyzed using the PAIGB polyclonal antibody (FIG. 20, FIG. 21 and FIG. 22). Using a 20× objective lens, FIG. 20 shows the induction of PAIGB by PTH 1-34 in the periosteum and endosteum of the bone marrow cavity within the calvariae. FIG. 21 shows, using a 100× objective lens, that PAIGB protein expression was induced by PTH 1-34 primarily in the osteoblasts that are adjacent to the bone surface within the periosteum of the calvariae. FIG. 22 demonstrates as seen with a 100× objective lens that PAIGB protein expression induced by PTH is found in the osteoblasts adjacent to the bone surface of the endosteum and not in the stromal cells of the bone marrow cavity.

The mouse calvariae was gently dissected and fixed in 10% phosphate-buffered formalin. After fixation, the calvariae were decalcified in TBD-2 decalcifying agent (SHANDON, Cat. # 6764003) for 7-8 hrs, dehydrated in graded alcohol, embedded in paraffin. The calvariae was bisected perpendicular to the sagittal suture through the central portion of the parietal bones parallel to the lambdoidal and coronal sutures and embedded in paraffin. Four to six 5 µm-thick representative, non-consecutive step sections were cut. Various sections were stained with hematoxylin and eosin (H&E) (Sigma, St. Louis, Mo.) and adjacent section were used for immunohistochemistry. The bone samples were then deparafinized in xylene and rehydrated in graded ethanol and PBS. Sections were treated with 0.3% $H_2O_2$/ methanol for 30 min at room temperature and then digested with proteinase K (Invitrogen) for 30 min at 37° C. After blocking with normal horse serum for 30 min, the section were incubated rabbit polyclonal antibody (which was raised against amino acid sequence RADAIEPRYYESWTRE (SEQ ID NO:11) which recognizes human, rat and mouse PAIGB protein) overnight at 4° C. Sections were then washed three times each for 10 min with PBS. The binding of antibody to epitope was assayed using a biotinylated secondary antibody (horse anti rabbit) and avidin-linked peroxidase kit (Vectastain Universal Elite ABC kit, PK-6200, Vector Laboratories). Controls included samples with the antibody-peroxidase kit but without PAIGB polyclonal antibody. The peroxidase was detected using peroxidase substrate kit DAB (SK-4100, Vector Laboratories).

Example 20

Quantification of Protein Levels of PAIGB

For a competitive based ELISA assay, 96 well plates are coated with either 10 µg/ml of a monoclonal or polyclonal antibody to PAIGB in 0.5 M $NaHCO_3$ pH 9.5 overnight at 4 C. The wells are then washed twice with TBS containing 0.05% Tween 20 (TBST) and then blocked with TBST containing 1% BSA for 1 hr at room temperature. The plate is then washed three times with TBST. The unknown samples and PAIGB protein standards (diluted in TBST) are added to the appropriate wells followed by the addition of a fixed amount of biotinylated PAIGB protein. After 2.5 hr incubation at room temperature, the plate is washed with TBST three times. Avidin-horseradish peroxidase Vectastain ABC reagent (Vector Laboratories) is then added and incubated for 1 hr at room temperature. Following three washes with TBST the 3,3',5,5'-tetramethylbenzidine (TMB) substrate (Vector Laboratories) is added to each well as described by the manufacturer. After 10-20 min the reaction is stopped with 4 M $H_2SO_4$ and the absorbance is read at 450 nm using a standard plate reader.

This competitive ELISA can be modified to generate an RIA by Iodinating ($^{125}I$) the PAIGB protein instead of biotinylation. In this case, as described above, both the unknown samples or unlabeled PAIGB protein standards would be placed in the appropriate wells followed by the addition of a fixed amount of $^{125}I$ PAIGB protein. After incubation for 2.5 hr the plate is washed and the remaining radioactivity is counted using a standard gamma counter.

In addition, a sandwich-based ELISA can be developed using two antibodies to PAIGB that recognized two different epitopes. In this example, the procedure is similar to the ELISA assay described above with the following modifications. After the 96 well plate is coated with the appropriate monoclonal or polyclonal PAIGB antibody and blocked in BSA containing blocking buffer, the unknown samples and PAIGB standards are added to the appropriate wells for 2.5 hr at room temperature. The plate is then washed, followed by the addition of the second PAIGB antibody (which recognizes a different epitope and the antibody is of a different species then the coated antibody) for 1 hr at room temperature. The plate is then washed followed by the addition of the secondary antibody (anti-rabbit or anti-mouse) conjugated with horseradish peroxidase (Vector Laboratories) for 1 hr at room temperature. The plate is then washed and TMB substrate is added as described above. After stopping the reaction, the plate is read at 450 nm using a standard plate reader.

Example 21

PAIGB Interacting Proteins—Mass Spectroscopy Analysis

In order to identify proteins that are involved in PAIGB function or interact with PAIGB polypeptide and to further ascertain how these partner proteins modulate PAIGB activity various methods known in the art such as two hybrid and/or immnuoprecipitation methods can be employed. For example, a set of immunoprecipitation pull down experiments can be performed followed by Mass Spectroscopy analysis of the complex.

For these experiments PAIGB was transiently overexpressed in an osteoblast cell line. Briefly, U2OS osteoblastic cells cultured in 150 mm dishes to 95% confluent were transfected with V5 tagged PAIGB expression plasmid with Lipofectamine 2000 (Invitrogen, Carlsbad, Calif.) as described by the manufacturer. Forty-eight hours post transfection, cells were rinsed 2× with cold PBS and the cellular protein was harvested using a lysis buffer (IP buffer) composed of 50 mM Tris-HCl pH 8.0, 150 mM NaCl, 1% NP40 and mammalian protease inhibitor cocktail, phosphatase inhibitor cocktail I and phosphatase inhibitor cocktail II (Sigma, St. Louis, Mo.). The cell lysate (0.5 ml) was centrifuged at 3,000 rpm, 4° C. for 10 minutes. The lysate was then pre-cleared by adding 250 µl Sepharose CL4B (Sigma, St. Louis, Mo.) per 1 mL lysate. The sample was incubated at 4° C. on orbital rotator for 30 minutes and then centifuged 3,000 rpm, 4° C. for 10 minutes.

To perform the immunoprecipitation, the supernatant was transferred to a new tube and 80 µl of anti-V5 Conjugated agarose (Sigma, St. Louis, Mo.) per 1 mg of protein extract was added to the sample and incubated for 1.5 hours, 4° C. on anorbital rotator. The sample was centrifuged at 1,000 rpm, 4° C., for 1 min and the supernatant were removed. The agarose pellet was washed 3× with the cell lysis Buffer containing 350 mM NaCl (1 ml/100 µl resin) followed by centrifugation at 1,000 rpm, 4° C. for 1 min. The sample was then washed 3× (1 mL/100 µl of initial resin volume) in immuniprecipitation (IP) Buffer, and centrifugated 1,000 rpm, 4° C. for 1 min each time. The supernatant was removed after the final wash, leaving approximately 10 µl above the beads. The interacting proteins were eluted in IP Buffer (amount equal to initial resin volume) containing V5 peptide (Sigma, St. Louis Mo.) (reconstituted in 1% acetic acid) at a final concentration of 1 mg/ml. The sample was incubated at room temperature for 60 minutes on an orbital rotator followed by centrifugation at 1,000 rpm at room temperature for 1 min. The supernatant containing the PAIGB interacting protein was collected.

The V5 labeled PAIGB protein complex was eluted from the anti V5 affinity matrix using excess V5 peptide in a total volume of 1.4 ml. The control transfection containing no PAIGB was handled in an identical fashion resulting in a control sample of 1.4 ml. Samples were reduced and denatured by the addition of DTT and SDS both to free the proteins from the complex and to prevent precipitation and binding of the proteins to the membrane in the subsequent concentration step. For reduction/denaturation, the solution was made 20 mM in DTT then 8 µl of 10% SDS was added and the solution was incubated at 37 C for 20 min. Samples were then concentrated to 40 µl using Microcon 3 centrifugal ultrafiltration devices (Amicon, Beverly, Mass.). After concentration, 10 µl of 5×SDS Laemmli loading buffer with 50 mM DTT and 20 mM sodium thioglycolate was added and the solutions were incubated at 37 C for 20 min.

In order to separate the Proteins from PAIGB complex, the concentrated samples (PAIGB and control) were separated onto an 8-16% Laemmli SDS gel (Hoeffer Medium Format, 14 cm×14 cm, gels from Jule Inc.). The fixed gel was silver stained using a protocol optimized for recovery of mass spectral information (Shevchenko et al, Anal Chem. 1996 Mar. 1;68(5):850-8.). The entire lane for both PAIGB and control samples were, in one experiment, cut into 40 gel bands. Generally, bands from the control lane were excised in conjunction with those from the PAIGB sample lane.

For protein digestion, Mass Spectrometry and protein identification the protein bands were excised from the gel, reduced, alkylated, and digested robotically using a gel digestion robot (Abimed, Langenfeld, Germany). Tryptic peptides were then eluted from the gel and concentrated (SpeedVac, Savant Instruments). 20-30% of the concentrated tryptic digests were injected onto a microcapillary C18 column (75 um×10 cm) eluting directly into a Finnigan DECA Xp ion trap mass spectrometer (ThermoFinnigan, San Jose, Calif.). HPLC gradients were delivered with an ABI 140 C system with a splitter to reduce the flow rate to the column to 200 nanoliters/min. Samples are injected automatically using a FAMOS autosampler (LC Packings). The ion trap was operated in a data dependent mode where peptides detected in a full scan automatically trigger collection of CID data on that peptide. An additional software feature known as dynamic exclusion was used. In this mode peptides, once targeted for CID, were added to a list to be rejected for an additional 2 minutes to prevent reacquisition of replicate spectra. Typically 1000 fragmentation spectra were collected in a single 60 minute LC-MS-MS experiment. Each gel band results in a separate LC-MS-MS file. LcQ datafiles are searched against several NCBI protein databases (non-redundant protein database and the translated Unigene cluster database) using the SEQUEST search algorithm running on a PC cluster.

The databases used in these experiments included the non-redundant NCBI protein database (NR) and the translated Unigene Cluster database. For all the gel bands from a typical experiment, the process returned tens of thousands of spectra matching to peptide entries in the database with various degrees of fidelity. Sequest uses the cross correlation coefficient (Xcorr) as a metric for the fidelity of the assignment. Spectra matching to peptide entries in the database with Xcorr>2.0 were assembled into consensus groups representing identified proteins using Oracle based software. Generally, though, a protein for which several peptides of Xcorr>2.0 were identified would be a confident assignment. Some prominent proteins were captured with more than 40 peptides represented. For differential experiments such as this, the entire ensemble of several hundred proteins detected in the entire control lane was subtracted from those found in the PAIGB sample. The result was a list of proteins detected specifically in the sample, which, by inference, interact directly with PAIGB.

Example 22

Evaluation of PAIGB Transgenic Mice

PAIGB transgenic mice were developed to overexpress PAIGB in a bone tissue specific fashion. This was achieved by driving the expression of the rat PAIGB transgene using a 3.6 kb collagen Type I promoter. We have developed two PAIGB transgenes constructs, one containing the PAIGB open reading frame and the 1.6 kb 3' UTR, while the other PAIGB transgene contains the open reading frame. We demonstrate here in the C57/BL6 strain of mice two PAIGB transgenic lines, one designated line 2 (derived from the full length cDNA transgene) while the second is designated line 54 (derived from the open reading frame). Histological characterization of the mice included analyzing the expression of PAIGB protein as well as the alkaline phosphatase activity in bone sections of the calvaria. Immunohistochemical analysis of PAIGB protein expression in the PAIGB transgenic mice was analyzed as previously described in Example 19. The histologic analysis of alkaline phosphatase activity (AP) in the calvarial sections was determined using the Vector Red (Vector Laboratories, Burlingame, Calif.) staining method. Briefly, mouse parietal bone fixed in 70% ethanol were cut into 6 μm sections and subsequently washed in PBS followed by a 0.1 M Tris-HCl pH 8.2 buffer wash. The sections were then stained for 30 min at 37 C with Vector Red substrate as described by the manufacturer.

The expression of PAIGB mRNA from total RNA of mouse bone was obtained by harvesting the tibias for each mouse and cleaning the remaining soft tissue from the bone. The most distal and proximal ends of the bone was removed and the bone marrow cavity was flushed with PBS using a syringe. The two tibias from each mouse were combined and the bones were made into a fine powder by placing the sample in liquid nitrogen and then smashing the bone with a pulverizer. The powder was transferred to a tube and 0.3 ml of denaturation solution (Ambion, Austin Tex.) was added and placed on ice. The samples were then homogenized for 30 sec, centrifuged for 10 min, 12,000×g at 4 C and the supernatant was collected. The pellet was re-extracted with denaturation solution and then centrifuged as done previously. The two supernatants were combined and 1.1 volume of Trizol (Invitrogen, Carlsbad, Calif.) was added and incubated at room temperature for 5 minutes. Chloroform (0.2 ml/1 ml Trizol) was added to each sample and shaken vigorously for 15 sec and then incubated for 2-3 minutes at room temperature. The samples were centrifuged for 15 min, 12,000×g at 4 C and the top aqueous phase was transferred to a new tube and 1 μg of glycogen (Ambion, Austin Tex.) was added to the sample. One volume of isopropanol was added and incubated at −20 C for 24 hr. The sample was centrifuged at maximum speed at 4 C for 20 min and the pellet was washed with 70% cold ethanol. Again the sample was centrifuged and the supernatant removed and the sample reconstituted in water for subsequent DNase (Ambion, Austin Tex.) treatment. Real time RT-PCR was performed using the appropriate rat PAIGB primers (SEQ ID 45, 46) and probe (SEQ ID 47)

FIG. 23 represents an example of both line 2 and line 54 heterozygous mice overexpressing PAIGB mRNA compared to non-transgenic controls as demonstrated by real time PCR. It was also determined, as demonstrated in FIG. 24, that line 2 (full length transgene) PAIGB heterozygous mice overexpress PAIGB protein in the periosteum of the calvaria compared to the littermate non-transgenic control mice. PAIGB protein overexpression was also noted in the sagittal suture region of the calvaria in the heterozygous mice compared to the non-transgenic control mice (FIG. 25). The result of this increase in PAIGB protein was an increase in alkaline phosphatase activity in the periosteum and the endosteum of the calvaria of the heterozygous mice compared to the non-transgenic control mice (FIG. 26). Furthermore, the increase in alkaline phosphatase was also associated with an increase in the calvaria thickness in the heterozygous mice compared to the non-transgenic control mice. This increase in alkaline phosphatase activity and calvaria thickness demonstrated in the heterozygous PAIGB overexpressing mice is indicative of a bone anabolic phenotype. This anabolic effect including an increase in alkaline phosphatase activity and calvaria thickness was also demonstrated in a second PAIGB transgenic mouse line 54 (open reading frame transgene) (FIG. 27).

Example 23

PAIGB Knockdown Approaches to Evaluate PAIGB Function

The use of small interfering RNAs (siRNA) is a sequence specific method to post-transcriptionally silence the expression of a gene of interest (reviewed by Gregory Hannon. Nature 418:244-251. 2002). In recent years, this technology been successfully developed for mammalian systems in order to analyze gene function (Elbashir, S. M., Harborth, J., Lendeckel, W., Yalcin, A., Weber, K., Tuschl, T. Nature 411: 494-498. 2001. Yu, J. Deruiter, S. L., Turner, D. L. PNAS 99:6047-6052. 2002.). Therefore, PAIGB siRNA is used to assess the effects of blocking PAIGB expression on osteoblast function and gene expression. For example, osteoblastic cells transfected with PAIGB siRNA for 24, 48 and 72 hrs is harvested at the indicated time points and the expression of bone forming markers such as alkaline phosphatase, osteocalcin and type I collagen is measured at both the mRNA and protein level. In addition, similar experiments can be expanded to include RNA isolation for subsequent expression profiling using Affymetrix gene chip technology (Affymetrix, Santa Clara, Calif.). The resulting expression profile will identify various signal transduction pathways other than the PTH pathway that PAIGB may modulate. Similar experiments can also be performed in the presence and absence of PTH 1-34. Since PTH 1-34 induces the expression of PAIGB, one can predict that transfection of osteoblasts prior to PTH treatment with PAIGB siRNA would block the induction of PAIGB expression. As a result, if there are no other functionally redundant PAIGB-like genes then PAIGB siRNA blocks the effects of PTH on PTH target genes (e.g. MMP13, connexin 43, type I collagen and alkaline phosphatase (Swarthout, J. T., D'Alonzo, R. C., Selvamurugan, N., Partridge, N. C. GENE 282: 1-17. 2002)) if the PTH induced regulation of these genes is dependent on PAIGB expression.

In addition to ascertaining the importance of PAIGB on osteoblast function, the influence of PAIGB on osteoblast proliferation and apoptosis can be evaluated using PAIGB siRNA. PAIGB is a downstream target of PTH signaling and PTH is known to influence osteoblast number and apoptosis and is an important aspect in promoting bone formation (Stavros C. Manolagas. Endocrine Reviews. 21: 115-137, 2000. Tashjian, A. H., Chabner, B. A. J. Bone Miner. Res. 17: 1151-1161. 2002.). These experiments can be performed similar to what has been described above in the presence and absence of PTH 1-34 and in various osteoblastic and stromal cell lines. The analysis of osteoblast or stromal cell number as well as cell apoptosis can be performed as described earlier in this application. PAIGB siRNA may block the effects of PTH on osteoblast cell number and apoptosis based its role in PTH induced bone anabolic signaling Multiple 21 nucleotide siRNAs for both rat and human PAIGB (SEQ ID 48, 49, 50, 51, 52, 53, 54, 55, 56, 57, 58, 59, 60, 61, 62, 63) were developed as a tool to further study the role of PAIGB in bone cell function. The siRNA's were selected similar to what has already been described (Elbashir, S. M., Harborth, J., Lendeckel, W., Yalcin, A., Weber, K., Tuschl, T. Nature 411: 494-498. 2001.) and based on the following criteria; 1) the G/C content was between 35-55%, 2) there were no identical base runs of greater than 4 bases, 3) the sequences were unique based on a BLAST search and 4) the sequences were determined to have minimal potential for secondary structure (loops and hairpins).

For transient transfection of the siRNAs, osteoblastic cells are plated at approximately 80% confluence in growth media the day prior to transfection. On the day of transfection, in a 6 well plate for example, the siRNA (10-100 nM) is added to a tube containing 1 ml of basal serum free media followed by the addition of 4 µl to 7.5 µl of Transfast (Promega, Madison, Wis.) or as described by the manufacturer. Other transfection reagents, such as Lipofectamine 2000 (Invitrogen, Carlsbad, Calif.) and Ribojuice (Novagen, Madison, Wis.) can be used. Following the addition of Transfast, the sample is incubated for 30 min at room temperature. Concurrently, the growth media is removed from the cells and is replaced with serum free basal media. Following the 30 min incubation the basal media is removed from the cells and then the siRNA containing mixture is added to the cells and incubated at 37 C for 4 hr. The transfection mixture is then removed and replaced with growth media and incubated overnight. The following day the cells is treated with or without PTH 1-34 (1-100 nM) for various time points depending on whether the endpoint of the experiment is gene expression or cell number or apoptosis analysis as previously described.

---

What is claimed is:

1. An isolated polypeptide encoded by an isolated nucleic acid fragment selected from the group consisting of:
   (a) an isolated nucleic acid fragment encoding SEQ ID NO: 2;
   (b) an isolated nucleic acid fragment encoding an amino acid sequence having at least 98% identity with SEQ ID NO: 2; and
   (c) an isolated nucleic acid fragment that hybridizes with the isolated nucleic acid fragment of (a) under hybridization conditions of 6×SSC (1M NaCl), 45 to 50% formamide, 1% SDS at 37° C., and a wash in 0.5× to 1×SSC at 55 to 60° C.;
wherein said polypeptide is parathyroid hormone anabolic induced gene in bone (PAIGB) polypeptide and has osteoblast bone forming activity in bone tissues.

2. The isolated polypeptide of claim 1 having the amino acid sequence set forth in SEQ ID NO: 2.

3. The isolated polypeptide of claim 1 which is involved in parathyroid hormone signaling pathway.

4. The isolated polypeptide of claim 1 which when overexpressed induces bone forming activity in bone tissues.

5. The isolated polypeptide of claim 1 which is overexpressed in response to intermittent parathyroid hormone administration.

6. A composition for regulating bone-forming activity in a mammal comprising an isolated polypeptide of claim 1.

7. A composition according to claim 6, wherein said parathyroid hormone anabolic induced gene in bone polypeptide is from human osteoblast cells.

8. A composition according to claim 6, wherein the bone forming activity is the regulation of bone growth.

9. A composition according to claim 6, wherein the bone forming activity is the regulation of bone density.

10. The composition according to claim 6, wherein the parathyroid hormone anabolic induced gene is bone polypeptide has the amino acid sequence set forth in SEQ ID NO: 2.

* * * * *

SEQUENCE LISTING

<160> NUMBER OF SEQ ID NOS: 63

<210> SEQ ID NO 1
<211> LENGTH: 2146
<212> TYPE: DNA
<213> ORGANISM: Rat

<400> SEQUENCE: 1

```
ccgggctgag ccgcagccgc agccgcaagc cgaacggccg ctgggcgcgc ccgcaacagg      60
ggaggatggg ctgcggcggg agccgagccg atgccatcga gccccgctac tatgagagct     120
ggacccggga gaccgagtcc acctggctca cctacaccga ctcggacgcg ctgcccagcg     180
```

-continued

| | |
|---|---|
| ccgcagccac ggacagcggc cccgaggcgg gcggcctgca cgcgggtgtg ctggaagacg | 240 |
| ggccgtcctc taacggtgtg ctccgacctg cagccccagg tggaatagcc aacccagaga | 300 |
| agaagatgaa ctgtgggacc caatgtccca actcacagag cctcagctca ggccctctga | 360 |
| cccagaagca gaatggcctt tggaccacag aggctaaaag ggatgccaag cgaatgtctg | 420 |
| caagagaagt cgctatcagc gtcacagaga atatccggca gatggacaga agtaaaaggg | 480 |
| tcacaaagaa ctgcatcaat tagcagtgtc tgggtgtgga agcacatgaa cttctttgtg | 540 |
| gcgtccagtc aaagaatatt gaagaagtgg gtgtcactca ctgaacgtgg atgcctctga | 600 |
| gcgacgcacg gccacccacg cggtgacgac catcccggtt tcctgtttat cacatacaga | 660 |
| aaatacatcg aaaagtcctg gaatatgttc acagattgcc aaactatggt ttgttttttcc | 720 |
| tctctgcagc ttccgtagca gggtctgctg taaccatggt gaagcccgtg ggcctgtgaa | 780 |
| tgaatattgg aatccccggg gcaaggagct cacgctagcg tagaaatttc acagtgcgtg | 840 |
| gtttcggaca agctcccttt tcctcctttc tttttaaata cggccattgt tttcacttaa | 900 |
| gagctggctc tcaccaactc taaactcaaa aatacaagaa tcagagaaac agagagactc | 960 |
| agaatgagat tcatcagtcc tagcttcacg tgctgactcc ccggtgccta tgcggtgcct | 1020 |
| ttaggaggtg tctatgacac acacacacac acacacacac acacacacac acacacacac | 1080 |
| acacacctgt tcctcctcta cctggaaagg tctcccaggc tggcatcagg cattggcttc | 1140 |
| cgaatcacaa tgtcacatgt tgggggccct tgcacccaac ctgcacccgc tttgggacct | 1200 |
| agctccatgt ggcttttccc atagctttct agttccctgt tcttctcatg gactttgtac | 1260 |
| tccagtcagg tcatttgcag ctgtaatcaa agactggaca ccactcccgg gggaaggtga | 1320 |
| cctaggaaca catggtgaca cacacgatgc ccccttggcc tttctgtaca cagccccaag | 1380 |
| gaccgtgtta ttttggtatc tgcaaagcaa ttagtttgga aagccagagc ctggttgatg | 1440 |
| tatattcctg ctgacatcag accaagaagg cactgtattg gaaagcaggc agccaacaca | 1500 |
| gccaagccat gctctgatat ggaccctttc cccacattcc taaacacatc ctcctgcaaa | 1560 |
| gtatggcaca gcctgagttt gaaaggaccg ttcacttgct tgggcttatt aaaggtatag | 1620 |
| tccaagttgt gtcaaactgt atcaacagac tccacatcta gcagcaagag cagtctggtg | 1680 |
| acatgtttat acgacacagt ccaagagaag taacctaagc gggctaaaat gcagatgctc | 1740 |
| acgcctgtct ctgaagtgat tctccaaca cagacagaac tgtaaactgt gcgtttattc | 1800 |
| gtattaaaat tcactgccaa tcttgtgcca gctacagtaa cagacacaga gggggttgga | 1860 |
| gtctggcagt cacgaccgta catctgactc tatggggagg cttgagactc aggagaatga | 1920 |
| cctgaaccct gcggcacagg accaaccatt gcagtggaat ctcacttcta ggttaaaggt | 1980 |
| agctttctat ccatcgcaaa tgtatgtctt ctcctctgcc rtgtagacta cagttttccc | 2040 |
| caacctctct caccttgact ccttgtcaaa gggcttttag ggaacttcat gttctgacaa | 2100 |
| tttaactaat aaaacaaaag caagccccgt gaaaaaaaa ccgggc | 2146 |

<210> SEQ ID NO 2
<211> LENGTH: 145
<212> TYPE: PRT
<213> ORGANISM: Rat

<400> SEQUENCE: 2

Met Gly Cys Gly Gly Ser Arg Ala Asp Ala Ile Glu Pro Arg Tyr Tyr
1               5                   10                  15

Glu Ser Trp Thr Arg Glu Thr Glu Ser Thr Trp Leu Thr Tyr Thr Asp
            20                  25                  30

Ser Asp Ala Leu Pro Ser Ala Ala Thr Asp Ser Gly Pro Glu Ala
         35                  40                  45

Gly Gly Leu His Ala Gly Val Leu Glu Asp Gly Pro Ser Ser Asn Gly
 50                  55                  60

Val Leu Arg Pro Ala Ala Pro Gly Gly Ile Ala Asn Pro Glu Lys Lys
 65                  70                  75                  80

Met Asn Cys Gly Thr Gln Cys Pro Asn Ser Gln Ser Leu Ser Ser Gly
                 85                  90                  95

Pro Leu Thr Gln Lys Gln Asn Gly Leu Trp Thr Thr Glu Ala Lys Arg
             100                 105                 110

Asp Ala Lys Arg Met Ser Ala Arg Glu Val Ala Ile Ser Val Thr Glu
             115                 120                 125

Asn Ile Arg Gln Met Asp Arg Ser Lys Arg Val Thr Lys Asn Cys Ile
130                 135                 140

Asn
145

<210> SEQ ID NO 3
<211> LENGTH: 2847
<212> TYPE: DNA
<213> ORGANISM: Homo sapiens

<400> SEQUENCE: 3
gcccggacta gggcggcgg gcaccgcagg agctccgcgc ggctgcagcg cgggcgggag      60
cggggacgcg atgtcgccgc cgccgcctcc ttgcggaccg ggctgcgcc tccggggctg    120 agccgccgcc agagccgaca gccgagcagc cgctgggcgc tccgcggcg caggaggatg    180 ggctgcggcg ggagccgggc ggatgccatc gagccccgct actacgagag ctggaccccgg   240 gagacagaat ccacctggct cacctacacc gactcggacg cgccgcccag cgccgccgcc    300
ccggacagcg gccccgaagc gggcggcctg cactcgggca tgctggaaga tggactgccc    360
tccaatggtg tgccccgatc tacagcccca gtggaatac ccaacccaga agaagacg     420 aactgtgaga cccagtgccc aaatcccag agcctcagct caggccctct gacccagaaa    480
cagaatggcc ttcagaccac agaggctaaa agagatgcta agagaatgcc tgcaaaagaa    540
gtcaccatta atgtaacaga tagcatccaa cagatggaca gaagtcgaag aatcacaaag    600
aactgtgtca actagcagag agtccaagca gaagggcaga tggacttctt cagtgtcctt    660
cacggcactg gatcccatca aagaaccttg aagaagtggc tgcccctgc tggacctgaa    720 ttctactgag tccctggcaa gactgtctta cctggcagca aactgctgcc tgatttgttg    780
ggaccttctg agccttctac ttatcatgta aatgtattgg cacagtgctt acatatgtta    840
ataaactgca aatgtgcagt tcagtttgtc tctttgcaac tcctgtaata cggtctggtg    900
taaaagtagt gagttaaagc tacaggtcag tttatgaaac agaaaagtag gaatgcattt    960
tctgggtgaa agagtcacac cttagtgcta taactctcct gcccatgata gtgtattctg   1020
tttcaggcaa gcttattctt tccttctttc atttttaaata ttgtcattac aaatcttacc   1080
aggttcactt aaaagctggc tttcatccaa ctctaaaccc acatattgaa aaaatcaagg   1140
tacaggaaaa ctccttgtta tccttgtttc cttagcttgg tatgagacag atcggatcca   1200
gtttcccatg caccaaccca ctgcccatgg catgtctttg ggaggtgtct gtgaagcagt   1260
catacctgct cctcatctgc ctggaaagtc tccctattcc agtgtccatg ttggcctcca   1320
gtccttaatg tcaccatgct tgtggccaat gcatccaaat aaggatacccc ctcagggctc   1380

```
agctagacat tgcaattttg catagctttc cagttccctt tgcttgtctt cttgactgtt    1440
ttccctctct atcggggtca cttgcaattg ttaatcaaag attgaacact gcgtaggaga    1500
gggagatgat ccagagacat gtggcagcag gcatggcttc cccttggcct ctctgtacac    1560
tgccccagga ctgtcatttt ggcatctgca aaggaatcac tttagaaagc cagcacctgg    1620
ttgatgtgta ttcatactga cattagattg atgtgcactg cattagaaat gaggtagctg    1680
acacagaaaa aggatgtttt gataggaata attttctagt atgtcttgaa acatgttcat    1740
ctggaagtat tttcctccaa agtaatgtag catgattttt caaggattgt taacatgcct    1800
gggattggga aagataggac taaagttgtg ccaaactata tcaataaatt ccatgtttag    1860
cagaaatagg cagcctattg gtgttatgtt tatgtaacat agtccagaga actgacatgc    1920
aggtcaaaag tcagatacgc aacctcctta tctgctaact ctgttattct caaacacaa     1980 gtgggtagtg tcattttttcc ttccttcctt ccattggcag attgtatatt tattcacaaa    2040
acattaaatg tccatcctgt gccaggtact atgcagatgt tgagggattt ggggtctggt    2100
tagtcgtgac tatctatcct gaatctaaca gtgacttcat aactaggaga ctgaattaga    2160
cccttaaggt atagtgtgtg ttgcaaatca ctctgcaatg gaaacttttta tattcagggt    2220 aggtttgtgt cttaaactag gtgttctaat caatgtacaa gactttacca tacacgcaac    2280
tttagttttt ctaaaccttc atcattttgt gattctttga gaaagggctt ttaggaactt    2340
tatgttctaa aaaatgtttt taacaataat aagataaaag aaaaacctgt gattcatatg    2400
tccccactgg cattactcag caggagcccc cagctgccaa aggttggcag tgatcctgca    2460
agttcaaggg ctctttctcc ctggggatgt gctttgtggc ttctctttac agctttgttt    2520
ctgcatcagt tcactgctgc atgttgtttg gaatttatca ccttaagaaa gtgtctctgt    2580
tttatataga aacactttct cacttacagg ggagaaggaa atgcagggca catgatctgg    2640
ccctccccag aacaatctgg atttcacgga gacagcaacc agaagttaaa ccatgtgact    2700
aaaaatgcat ctggctactt tttcatgtat gtatgagaca gaaactaatc cttactatcc    2760
tattaggata ccacttttca ttgcaaagtt tgtgtcaata aagtcattaa ttttaaacat    2820
aaaaaaaaaa aaaaaaaaa aaaaaag                                         2847
```

<210> SEQ ID NO 4
<211> LENGTH: 145
<212> TYPE: PRT
<213> ORGANISM: Homo sapiens

<400> SEQUENCE: 4

```
Met Gly Cys Gly Gly Ser Arg Ala Asp Ala Ile Glu Pro Arg Tyr Tyr
1               5                   10                  15

Glu Ser Trp Thr Arg Glu Thr Glu Ser Thr Trp Leu Thr Tyr Thr Asp
            20                  25                  30

Ser Asp Ala Pro Pro Ser Ala Ala Ala Pro Asp Ser Gly Pro Glu Ala
        35                  40                  45

Gly Gly Leu His Ser Gly Met Leu Glu Asp Gly Leu Pro Ser Asn Gly
    50                  55                  60

Val Pro Arg Ser Thr Ala Pro Gly Gly Ile Pro Asn Pro Glu Lys Lys
65                  70                  75                  80

Thr Asn Cys Glu Thr Gln Cys Pro Asn Pro Gln Ser Leu Ser Ser Gly
                85                  90                  95

Pro Leu Thr Gln Lys Gln Asn Gly Leu Gln Thr Thr Glu Ala Lys Arg
            100                 105                 110
```

Asp Ala Lys Arg Met Pro Ala Lys Glu Val Thr Ile Asn Val Thr Asp
        115                 120                 125

Ser Ile Gln Gln Met Asp Arg Ser Arg Arg Ile Thr Lys Asn Cys Val
    130                 135                 140

Asn
145

<210> SEQ ID NO 5
<211> LENGTH: 271
<212> TYPE: DNA
<213> ORGANISM: Homo sapiens

<400> SEQUENCE: 5
atgggctgcg gcgggagccg ggcggatgcc atcgagcccc gctactacga gagctggacc        60
cgggagacag aatccacctg gctcacctac accgactcgg acgcgccgcc cagcgccgcc       120
gccccggaca gcggccccga agcgggcggc ctgcactcgg gctaaaagag atgctaagag       180
aatgcctgca aagaagtca ccattaatgt aacagatagc atccaacaga tggacagaag        240
tcgaagaatc acaaagaact gtgtcaacta g                                      271

<210> SEQ ID NO 6
<211> LENGTH: 54
<212> TYPE: PRT
<213> ORGANISM: Homo sapiens

<400> SEQUENCE: 6

Met Gly Cys Gly Gly Ser Arg Ala Asp Ala Ile Glu Pro Arg Tyr Tyr
1               5                   10                  15

Glu Ser Trp Thr Arg Glu Thr Glu Ser Thr Trp Leu Thr Tyr Thr Asp
            20                  25                  30

Ser Asp Ala Pro Pro Ser Ala Ala Ala Pro Asp Ser Gly Pro Glu Ala
        35                  40                  45

Gly Gly Leu His Ser Gly
    50

<210> SEQ ID NO 7
<211> LENGTH: 1988
<212> TYPE: DNA
<213> ORGANISM: Mouse

<400> SEQUENCE: 7
gcagcagcca cagccgcaag ccgagcggcc gccgggcgcg cccgcaacac gggaggatgg        60
gctgcggcgg gagccgagcc gatgccatcg agccccgcta ctacgagagt tggacccggg       120
agacggagtc cacctggctc acctacaccg actcggacgc gctgcccagc gccgcagcca       180
cggacagcgg ccccgaggcg gcggcctgc acgcgggtgt gctggaagac ggactgtcct        240 ctaacgggt gctccgacct gcagccccgg gtggaatagc caaccagag aagaagatga        300 actgtgggac ccaatgtccc aactcacaga acctcagctc aggccctctg acccagaaac       360
agaatggcct ctgggccaca gaggctaaga gggatgctaa gcggatgtct gcaagagaag       420
tggctattaa cgttacagag aatattcggc agatggacag aagtaaaagg gtcaccaaga       480
actgcatcaa ttagcagtgc ccggatgtgg aggcagatga acttcttggt ggagtctagt       540
caaagaatcc tgaagaagtt gatgtcactc gatgagtgtg atgcctctg agtgacacac        600 ggccacccaa cgctgtgacg aacatctcgg tttcctgttt atcacatata gaaaatacat       660
cgaaaagtcc tgaaatatgt tcatagattg ccaaaatgtg gtttgttttt tcccctctgc       720

-continued

```
agcttccata gcatggtctg ctgtagccat ggcgactggc acagaaaggc tggagtaacg      780
gaatccctgt caaggagctc acactcgtgc agagctttct cagtgtgtgg ttgcagacaa      840
actccttctt tcctcctttc cttttaaata cggccaccac aaaatttact gttttcactt      900
aagagctggc tcccagccaa ctctaaatcc agaaatacaa gaatccaaaa aaccagagag      960
actcggaacg agctgaatca gtcccagctt cacgtgctgg ctccccggtg cctactcggt     1020
gtctttgaga ggtgtctatg agacacgcac atgcacacgc acacacacac atatacctgt     1080
ttctcctcta cctggaaagg actcccaggc tagcatccag gcgttggctt ccaaaccaga     1140
atgtcacatg tctgtggcct ttgctccctt gggacctag cttcatgttg cttttcccca      1200 tagcttttcca gttccctatt gttctggtgg gctttgtacc ttcagtcagg tggtcatttg     1260
cagctggaca ccactcacag gggggaaagt gacctaggaa cacatggtgg cacacgtgat     1320
acccctttgg cccttctgta cacagcccca aggaccatgt tattttttggt atctgcagag    1380 taattagttt ggaaagccag aggctggttg atgtatattc ctgttgacat agtctaacaa     1440
ggcactcact gtattgaaaa acaggcacca acatggtaaa gcgatgcttt gataggaacc     1500
cttccccagc attcctaagc acccttcct gcagagtatg ttgacacagc atgagtctga      1560
aaggactgtt aacatgcttg ggcttattaa ggtccaagtc atatcaaact gtaccaacaa     1620
actcacatct agcagcaata gtagtctggc ggcatgctta cgtgacagtt caagagaagt     1680
cacccaagcg gattaagatg cagatgctca ctgctgtctc tgacttattt ctccaacaca     1740
agtagaactg tagactgtat gtttattagt gttaagattc actgccaacc ttgtgccagc     1800
tacagtaaca gtcgcagagg gatttggagt cgggaagtca cgactgtact tctgactctg     1860
tgaggaggct tggtactcag gagactgaca cggaccctgt ggcacaagac caatgattgc     1920
agtggaatct cacacttagg taaaggtagc tttctgtcaa tcacagatgt atgtcttctc     1980
ctttgccg                                                              1988
```

<210> SEQ ID NO 8
<211> LENGTH: 145
<212> TYPE: PRT
<213> ORGANISM: Mouse

<400> SEQUENCE: 8

```
Met Gly Cys Gly Gly Ser Arg Ala Asp Ala Ile Glu Pro Arg Tyr Tyr
1               5                   10                  15

Glu Ser Trp Thr Arg Glu Thr Glu Ser Thr Trp Leu Thr Tyr Thr Asp
            20                  25                  30

Ser Asp Ala Leu Pro Ser Ala Ala Thr Asp Ser Gly Pro Glu Ala
        35                  40                  45

Gly Gly Leu His Ala Gly Val Leu Glu Asp Gly Leu Ser Ser Asn Gly
    50                  55                  60

Val Leu Arg Pro Ala Ala Pro Gly Gly Ile Ala Asn Pro Glu Lys Lys
65                  70                  75                  80

Met Asn Cys Gly Thr Gln Cys Pro Asn Ser Gln Asn Leu Ser Ser Gly
            85                  90                  95

Pro Leu Thr Gln Lys Gln Asn Gly Leu Trp Ala Thr Glu Ala Lys Arg
            100                 105                 110

Asp Ala Lys Arg Met Ser Ala Arg Glu Val Ala Ile Asn Val Thr Glu
        115                 120                 125

Asn Ile Arg Gln Met Asp Arg Ser Lys Arg Val Thr Lys Asn Cys Ile
    130                 135                 140
```

Asn
145

<210> SEQ ID NO 9
<211> LENGTH: 1821
<212> TYPE: DNA
<213> ORGANISM: Mouse

<400> SEQUENCE: 9

| | | | | | | |
|---|---|---|---|---|---|---|
| gcagcagcca | cagccgcaag | ccgagcggcc | gccgggcgcg | cccgcaacac | gggaggatgg | 60 |
| gctgcggcgg | gagccgagcc | gatgccatcg | agccccgcta | ctacgagagt | tggacccggg | 120 |
| agacggagtc | cacctggctc | acctacaccg | actcggacgc | gctgcccagc | gccgcagcca | 180 |
| cggacagcgg | ccccgaggcg | ggcggcctgc | acgcgggcta | agagggatgc | taagcggatg | 240 |
| tctgcaagag | aagtggctat | taacgttaca | gagaatattc | ggcagatgga | cagaagtaaa | 300 |
| agggtcacca | gaactgcatc | aattagcag | tgcccggatg | tggaggcaga | tgaacttctt | 360 |
| ggtggagtct | agtcaaagaa | tcctgaagaa | gttgatgtca | ctcgatgagt | gtggatgcct | 420 |
| ctgagtgaca | cacggccacc | caacgctgtg | acgaacatct | cggtttcctg | tttatcacat | 480 |
| atagaaaata | catcgaaaag | tcctgaaata | tgttcataga | ttgccaaaat | gtggtttgtt | 540 |
| ttttcccctc | tgcagcttcc | atagcatggt | ctgctgtagc | catggcgact | ggcacagaaa | 600 |
| ggctggagta | acggaatccc | tgtcaaggag | ctcacactcg | tgcagagctt | tctcagtgtg | 660 |
| tggttgcaga | caaactcctt | ctttcctcct | ttcctttaa | atacggccac | cacaaaattt | 720 |
| actgttttca | cttaagagct | ggctcccagc | caactctaaa | tccagaaata | caagaatcca | 780 |
| aaaaaccaga | gagactcgga | acgagctgaa | tcagtcccag | cttcacgtgc | tggctccccg | 840 |
| gtgcctactc | ggtgtctttg | agaggtgtct | atgagacacg | cacatgcaca | cgcacacaca | 900 |
| cacacatacc | tgtttctcct | ctacctggaa | aggactccca | ggctagcatc | caggcgttgg | 960 |
| cttccaaacc | agaatgtcac | atgtctgtgg | cctttgctcc | ctttgggacc | tagcttcatg | 1020 |
| ttgcttttcc | ccatagcttt | ccagttccct | attgttctgg | tgggctttgt | accttcagtc | 1080 |
| aggtggtcat | ttgcagctgg | acaccactca | caggggggaa | agtgacctag | gaacacatgg | 1140 |
| tggcacacgt | gataccccctt | tggcccttct | gtacacagcc | ccaaggacca | tgttattttt | 1200 |
| ggtatctgca | gagtaattag | tttggaaagc | cagaggctgg | ttgatgtata | ttcctgttga | 1260 |
| catagtctaa | caaggcactc | actgtattga | aaaacaggca | ccaacatggt | aaagcgatgc | 1320 |
| tttgatagga | acccttcccc | agcattccta | agcacacctt | cctgcagagt | atgttgacac | 1380 |
| agcatgagtc | tgaaaggact | gttaacatgc | ttgggcttat | taaggtccaa | gtcatatcaa | 1440 |
| actgtaccaa | caaactcaca | tctagcagca | atagtagtct | ggcggcatgc | ttacgtgaca | 1500 |
| gttcaagaga | agtcacccaa | gcggattaag | atgcagatgc | tcactgctgt | ctctgactta | 1560 |
| tttctccaac | acaagtagaa | ctgtagactg | tatgtttatt | agtgttaaga | ttcactgcca | 1620 |
| accttgtgcc | agctacagta | acagtcgcag | agggatttgg | agtcgggaag | tcacgactgt | 1680 |
| acttctgact | ctgtgaggag | gcttggtact | caggagactg | acacgaccc | tgtggcacaa | 1740 |
| gaccaatgat | tgcagtggaa | tctcacactt | aggtaaaggt | agctttctgt | caatcacaga | 1800 |
| tgtatgtctt | ctcctttgcc | g | | | | 1821 |

<210> SEQ ID NO 10
<211> LENGTH: 54
<212> TYPE: PRT
<213> ORGANISM: Mouse

-continued

<400> SEQUENCE: 10

Met Gly Cys Gly Gly Ser Arg Ala Asp Ala Ile Glu Pro Arg Tyr Tyr
1               5                   10                  15

Glu Ser Trp Thr Arg Glu Thr Glu Ser Thr Trp Leu Thr Tyr Thr Asp
            20                  25                  30

Ser Asp Ala Leu Pro Ser Ala Ala Thr Asp Ser Gly Pro Glu Ala
        35                  40                  45

Gly Gly Leu His Ala Gly
    50

<210> SEQ ID NO 11
<211> LENGTH: 16
<212> TYPE: PRT
<213> ORGANISM: Artificial Sequence
<220> FEATURE:
<223> OTHER INFORMATION: synthetic peptide

<400> SEQUENCE: 11

Arg Ala Asp Ala Ile Glu Pro Arg Tyr Tyr Glu Ser Trp Thr Arg Glu
1               5                   10                  15

<210> SEQ ID NO 12
<211> LENGTH: 12
<212> TYPE: PRT
<213> ORGANISM: Artificial Sequence
<220> FEATURE:
<223> OTHER INFORMATION: synthetic peptide

<400> SEQUENCE: 12

Glu Asp Gly Leu Pro Ser Asn Gly Val Pro Arg Ser
1               5                   10

<210> SEQ ID NO 13
<211> LENGTH: 13
<212> TYPE: PRT
<213> ORGANISM: Artificial Sequence
<220> FEATURE:
<223> OTHER INFORMATION: synthetic peptide

<400> SEQUENCE: 13

Glu Ala Lys Arg Asp Ala Lys Arg Met Asp Ala Lys Glu
1               5                   10

<210> SEQ ID NO 14
<211> LENGTH: 14
<212> TYPE: PRT
<213> ORGANISM: Artificial Sequence
<220> FEATURE:
<223> OTHER INFORMATION: synthetic peptide

<400> SEQUENCE: 14

Gln Met Asp Arg Ser Arg Arg Ile Thr Lys Asn Cys Val Asn
1               5                   10

<210> SEQ ID NO 15
<211> LENGTH: 792
<212> TYPE: DNA
<213> ORGANISM: Mouse

<400> SEQUENCE: 15
tttgctggtg ttgttcatcc atcgctttta gaacaagtgg ccagaaaact tgggagggg      60 atttttgtga gcttcggagc tacccagaac agaaagatgg ttttaaagag ggtggatag     120 gtaggtggat gactggatcc gtgggtggat gcacaggtgg acagatgagg gatggatgga    180

```
tggatggatg ggagcccagg aggtcgactg aagactgaag agggacccctt tttcttcttc        240 ccaccacctg tctgctactc tgttgcaccg catctgccag aacactgaag aagggactgg        300
cggctgggcg gtgggagagg cgaggttgag gggtgctggg gaaggaaagt ggagaggagg        360
agggccttgg agacagagag gaggggcccc cgggagcccg gcgctggcag cggctctggc        420
ggttagggga ccaatgtcgc tgccgccgcc tcctcctcgg gggccggagc tgcgtcgccc        480
gggctgagca gcagccacag ccgcaagcgg agcggccgcc gggcgcgccc gcaacacggg        540
aggatgggct gcggcgggag ccgagccgat gccatcgagc cccgctacta cgagagttgg        600
acccgggaga cggagtccac ctggctcacc tacaccgact cggacgcgct gcccagcgcc        660
gcagccacgg acagcggccc cgaggcgggc ggcctgcacg cgggtgagtg agccccgcgc        720
ccgcgaggcc cggctgcctg cagcgagctg gagctgcagg ggagcctggg ggtagccagc        780
aaccctatgg ca                                                           792
```

```
<210> SEQ ID NO 16
<211> LENGTH: 29
<212> TYPE: DNA
<213> ORGANISM: Rat
<220> FEATURE:
<223> OTHER INFORMATION: Oligonucleotide

<400> SEQUENCE: 16
cccacattcc taaacacatc ctcctgcaa                                          29

<210> SEQ ID NO 17
<211> LENGTH: 22
<212> TYPE: DNA
<213> ORGANISM: Rat
<220> FEATURE:
<223> OTHER INFORMATION: Oligonucleotide

<400> SEQUENCE: 17
ccatgctctg atatggaccc tt                                                 22

<210> SEQ ID NO 18
<211> LENGTH: 22
<212> TYPE: DNA
<213> ORGANISM: Rat
<220> FEATURE:
<223> OTHER INFORMATION: Oligonucleotide

<400> SEQUENCE: 18
tcaaactcag gctgtgccat ac                                                 22

<210> SEQ ID NO 19
<211> LENGTH: 22
<212> TYPE: DNA
<213> ORGANISM: Mouse
<220> FEATURE:
<223> OTHER INFORMATION: Oligonucleotide

<400> SEQUENCE: 19
tgtgaggagg cttggtactc ag                                                 22

<210> SEQ ID NO 20
<211> LENGTH: 22
<212> TYPE: DNA
<213> ORGANISM: Mouse
<220> FEATURE:
<223> OTHER INFORMATION: Oligonucleotide
```

```
<400> SEQUENCE: 20
gagattccac tgcaatcatt gg                                    22

<210> SEQ ID NO 21
<211> LENGTH: 24
<212> TYPE: DNA
<213> ORGANISM: Mouse
<220> FEATURE:
<223> OTHER INFORMATION: Oligonucleotide

<400> SEQUENCE: 21
tgacacggac cctgtggcac aaga                                  24

<210> SEQ ID NO 22
<211> LENGTH: 18
<212> TYPE: DNA
<213> ORGANISM: Homo sapiens
<220> FEATURE:
<223> OTHER INFORMATION: Oligonucleotide

<400> SEQUENCE: 22
atgcttgtgg ccaatgca                                         18

<210> SEQ ID NO 23
<211> LENGTH: 27
<212> TYPE: DNA
<213> ORGANISM: Homo sapiens
<220> FEATURE:
<223> OTHER INFORMATION: Oligonucleotide

<400> SEQUENCE: 23
gatagagagg gaaaacagtc aagaaga                               27

<210> SEQ ID NO 24
<211> LENGTH: 27
<212> TYPE: DNA
<213> ORGANISM: Homo sapiens
<220> FEATURE:
<223> OTHER INFORMATION: Oligonucleotide

<400> SEQUENCE: 24 accccctcagg gctcagctag acattgc                              27

<210> SEQ ID NO 25
<211> LENGTH: 27
<212> TYPE: DNA
<213> ORGANISM: Artificial Sequence
<220> FEATURE:
<223> OTHER INFORMATION: Oligonucleotide

<400> SEQUENCE: 25
ccatcctaat cagactcact atagcgc                               27

<210> SEQ ID NO 26
<211> LENGTH: 24
<212> TYPE: DNA
<213> ORGANISM: Artificial Sequence
<220> FEATURE:
<223> OTHER INFORMATION: Oligonucleotide

<400> SEQUENCE: 26
gattccactg caatggttgg tcct                                  24

<210> SEQ ID NO 27
<211> LENGTH: 24
```

-continued

```
<212> TYPE: DNA
<213> ORGANISM: Artificial Sequence
<220> FEATURE:
<223> OTHER INFORMATION: Oligonucleotide

<400> SEQUENCE: 27
aaccgggatg gtcgtcaccg cgtg                                              24

<210> SEQ ID NO 28
<211> LENGTH: 25
<212> TYPE: DNA
<213> ORGANISM: Artificial Sequence
<220> FEATURE:
<223> OTHER INFORMATION: Oligonucleotide

<400> SEQUENCE: 28
ctgtccatct gccggatatt ctctg                                             25

<210> SEQ ID NO 29
<211> LENGTH: 22
<212> TYPE: DNA
<213> ORGANISM: Mouse
<220> FEATURE:
<223> OTHER INFORMATION: Oligonucleotide

<400> SEQUENCE: 29
ttccccagca ttcctaagca ca                                                22

<210> SEQ ID NO 30
<211> LENGTH: 24
<212> TYPE: DNA
<213> ORGANISM: Mouse
<220> FEATURE:
<223> OTHER INFORMATION: Oligonucleotide

<400> SEQUENCE: 30
tacggcaaag gagaagacat acat                                              24

<210> SEQ ID NO 31
<211> LENGTH: 20
<212> TYPE: DNA
<213> ORGANISM: Mouse
<220> FEATURE:
<223> OTHER INFORMATION: Oligonucleotide

<400> SEQUENCE: 31
gcaggagcca cagccgcaag                                                   20

<210> SEQ ID NO 32
<211> LENGTH: 20
<212> TYPE: DNA
<213> ORGANISM: Mouse
<220> FEATURE:
<223> OTHER INFORMATION: Oligonucleotide

<400> SEQUENCE: 32
cggcaaagga gaagacatac                                                   20

<210> SEQ ID NO 33
<211> LENGTH: 1086
<212> TYPE: DNA
<213> ORGANISM: Homo sapiens

<400> SEQUENCE: 33
ctctgaccca gaaacagaat ggccttcaga ccacagaggc taaaagagat gctaagagaa       60
```

```
tgcctgcaaa agaagtcacc attaatgtaa cagatagcat ccaacagatg gacagaagtc    120
gaagaatcac aaagaactgt gtcaactagc agagagtcca agcagaaggg cagatggact    180
tcttcagtgt ccttcacggc actggatccc atcaaagaac cttgaagaag tggctgcccc    240
ttgctggacc tgaattctac tgagtccctg gcaagactgt cttacctggc agcaaactgc    300
tgcctgattt gttgggacct tctgagcctt ctacttatca tgtaaatgta ttggcacagt    360
gcttacatat gttaataaac tgcaaatgtg cagttcagtt tgtctctttg caactcctgt    420
aatacggtct ggtgtaaaag tagtgagtta aagctacagg tcagtttatg aaacagaaaa    480
gtagggatgc attttctggg tgaaagagtc acacctagt gctataactc tcctgcccat     540
gatagtgtat tctgtttcag gcaagcttat tctttccttc tttcatttta aatattgtca    600
ttacaaatct taccaggttc acttaaaagc tggctttcat ccaactctaa acccacatat    660
tgaaaaaatc aaggtacagg aaaactcctt gttatccttg tttccttagc ttggtatgag    720
acagatcgga tccagtttcc catgcaccaa cccactgccc atggcatgtc tttgggaggt    780
gtctgtgaag cagtcatacc tgctcctcat ctgcctggaa agtcctccta ttccagtgtc    840
catgttggcc tccagtcctt aatgtcacca tgcttgtggc caatgcatcc aaataaggat    900
acccctcagg gctcagctag acattgcaat tttgcatagc tttccagttc cctttgcttg    960
tcttcttgac tgtcttccct ctctatcggg gtcacttgca attgttaatc aaagattgaa   1020
cactgcgtag gagagggaga tgatccagag acatgtggca gcaggcatgg cttcccttg    1080 gcctct                                                              1086

<210> SEQ ID NO 34
<211> LENGTH: 31
<212> TYPE: DNA
<213> ORGANISM: Homo sapiens
<220> FEATURE:
<223> OTHER INFORMATION: Oligonucleotide

<400> SEQUENCE: 34
gaagatctcc accatgggct gcggcgggag c                                    31

<210> SEQ ID NO 35
<211> LENGTH: 28
<212> TYPE: DNA
<213> ORGANISM: Homo sapiens
<220> FEATURE:
<223> OTHER INFORMATION: Oligonucleotide

<400> SEQUENCE: 35
gaagatctct agttgacaca gttctttg                                        28

<210> SEQ ID NO 36
<211> LENGTH: 18
<212> TYPE: DNA
<213> ORGANISM: Homo sapiens
<220> FEATURE:
<223> OTHER INFORMATION: Oligonucleotide

<400> SEQUENCE: 36
atgggctgcg gcgggagc                                                   18

<210> SEQ ID NO 37
<211> LENGTH: 20
<212> TYPE: DNA
<213> ORGANISM: Homo sapiens
<220> FEATURE:
<223> OTHER INFORMATION: Oligonucleotide
```

```
<400> SEQUENCE: 37
gatcaactgt gtcaagaaac                                                 20

<210> SEQ ID NO 38
<211> LENGTH: 20
<212> TYPE: DNA
<213> ORGANISM: Mouse
<220> FEATURE:
<223> OTHER INFORMATION: Oligonucleotide

<400> SEQUENCE: 38
ccccgctact acgagagttg                                                 20

<210> SEQ ID NO 39
<211> LENGTH: 20
<212> TYPE: DNA
<213> ORGANISM: Mouse
<220> FEATURE:
<223> OTHER INFORMATION: Oligonucleotide

<400> SEQUENCE: 39
ctacgtcaag aaccactggg                                                 20

<210> SEQ ID NO 40
<211> LENGTH: 397
<212> TYPE: DNA
<213> ORGANISM: Mouse

<400> SEQUENCE: 40
gccccgctac tacgagagtt ggacccggga gacggagtcc acctggctca cctacaccga     60
ctcggacgcg ctgcccagcg ccgcagccac ggacagcggc cccgaggcgg gcggcctgca    120
cgcgggtgtg ctggaagacg gactgtcctc taacggggtg ctccgacctg cagccccggg    180
tggaatagcc aacccagaga agaagatgaa ctgtgggacc caatgtccca actcacagaa    240
cctcagctca ggccctctga cccagaaaca gaatggcctc tgggccacag aggctaagag    300
ggatgctaag cggatgtctg caagagaagt ggctattaac gttacagaga atattcggca    360
gatggacaga agtaaaaggg tcaccaagaa ctgcatc                             397

<210> SEQ ID NO 41
<211> LENGTH: 21
<212> TYPE: DNA
<213> ORGANISM: Homo sapiens
<220> FEATURE:
<223> OTHER INFORMATION: Oligonucleotide

<400> SEQUENCE: 41
gctggaagat ggactgccct c                                               21

<210> SEQ ID NO 42
<211> LENGTH: 22
<212> TYPE: DNA
<213> ORGANISM: Homo sapiens
<220> FEATURE:
<223> OTHER INFORMATION: Oligonucleotide

<400> SEQUENCE: 42
ctctgtggtc tgaaggccat tc                                              22

<210> SEQ ID NO 43
<211> LENGTH: 21
<212> TYPE: DNA
```

```
<213> ORGANISM: Rat
<220> FEATURE:
<223> OTHER INFORMATION: Oligonucleotide

<400> SEQUENCE: 43
gaagacgggc cgtcctctaa c                                              21

<210> SEQ ID NO 44
<211> LENGTH: 21
<212> TYPE: DNA
<213> ORGANISM: Rat
<220> FEATURE:
<223> OTHER INFORMATION: Oligonucleotide

<400> SEQUENCE: 44
gtccaaaggc cattctgctt c                                              21

<210> SEQ ID NO 45
<211> LENGTH: 18
<212> TYPE: DNA
<213> ORGANISM: Rat
<220> FEATURE:
<223> OTHER INFORMATION: Oligonucleotide

<400> SEQUENCE: 45
acgggccgtc ctctaacg                                                  18

<210> SEQ ID NO 46
<211> LENGTH: 22
<212> TYPE: DNA
<213> ORGANISM: Rat
<220> FEATURE:
<223> OTHER INFORMATION: Oligonucleotide

<400> SEQUENCE: 46
acattgggtc ccacagttca tc                                             22

<210> SEQ ID NO 47
<211> LENGTH: 24
<212> TYPE: DNA
<213> ORGANISM: Rat
<220> FEATURE:
<223> OTHER INFORMATION: Oligonucleotide

<400> SEQUENCE: 47
agccccaggt ggaatagcca accc                                           24

<210> SEQ ID NO 48
<211> LENGTH: 21
<212> TYPE: RNA
<213> ORGANISM: Rat
<220> FEATURE:
<223> OTHER INFORMATION: Oligonucleotide

<400> SEQUENCE: 48
uagccaaccc agagaagaau u                                              21

<210> SEQ ID NO 49
<211> LENGTH: 21
<212> TYPE: RNA
<213> ORGANISM: Rat
<220> FEATURE:
<223> OTHER INFORMATION: Oligonucleotide

<400> SEQUENCE: 49
uucuucucug gguuggcuau u                                              21
```

-continued

<210> SEQ ID NO 50
<211> LENGTH: 21
<212> TYPE: RNA
<213> ORGANISM: Rat
<220> FEATURE:
<223> OTHER INFORMATION: Oligonucleotide

<400> SEQUENCE: 50
cucacagagc cucagcucau u					21

<210> SEQ ID NO 51
<211> LENGTH: 21
<212> TYPE: RNA
<213> ORGANISM: Rat
<220> FEATURE:
<223> OTHER INFORMATION: Oligonucleotide

<400> SEQUENCE: 51
ugagcugagg cucugugagu u					21

<210> SEQ ID NO 52
<211> LENGTH: 21
<212> TYPE: RNA
<213> ORGANISM: Rat
<220> FEATURE:
<223> OTHER INFORMATION: Oligonucleotide

<400> SEQUENCE: 52
gaacugcauc aauuagcagu u					21

<210> SEQ ID NO 53
<211> LENGTH: 21
<212> TYPE: RNA
<213> ORGANISM: Rat
<220> FEATURE:
<223> OTHER INFORMATION: Oligonucleotide

<400> SEQUENCE: 53
cugcuaauug augcaguucu u					21

<210> SEQ ID NO 54
<211> LENGTH: 21
<212> TYPE: RNA
<213> ORGANISM: Rat
<220> FEATURE:
<223> OTHER INFORMATION: Oligonucleotide

<400> SEQUENCE: 54
cuucuuugug gcguccaguu u					21

<210> SEQ ID NO 55
<211> LENGTH: 21
<212> TYPE: RNA
<213> ORGANISM: Rat
<220> FEATURE:
<223> OTHER INFORMATION: Oligonucleotide

<400> SEQUENCE: 55
acuggacgcc acaaagaagu u					21

<210> SEQ ID NO 56
<211> LENGTH: 21
<212> TYPE: RNA
<213> ORGANISM: Homo sapiens
<220> FEATURE:

-continued

<223> OTHER INFORMATION: Oligonucleotide

<400> SEQUENCE: 56
uccaccuggc ucaccuacau u          21

<210> SEQ ID NO 57
<211> LENGTH: 21
<212> TYPE: RNA
<213> ORGANISM: Homo sapiens
<220> FEATURE:
<223> OTHER INFORMATION: Oligonucleotide

<400> SEQUENCE: 57
uguaggugag ccagguggau u          21

<210> SEQ ID NO 58
<211> LENGTH: 21
<212> TYPE: RNA
<213> ORGANISM: Homo sapiens
<220> FEATURE:
<223> OTHER INFORMATION: Oligonucleotide

<400> SEQUENCE: 58
uacccaaccc agagaagaau u          21

<210> SEQ ID NO 59
<211> LENGTH: 21
<212> TYPE: RNA
<213> ORGANISM: Homo sapiens
<220> FEATURE:
<223> OTHER INFORMATION: Oligonucleotide

<400> SEQUENCE: 59
uucuucucug gguugggua u          21

<210> SEQ ID NO 60
<211> LENGTH: 21
<212> TYPE: RNA
<213> ORGANISM: Homo sapiens
<220> FEATURE:
<223> OTHER INFORMATION: Oligonucleotide

<400> SEQUENCE: 60
gagaugcuaa gagaaugccu u          21

<210> SEQ ID NO 61
<211> LENGTH: 21
<212> TYPE: RNA
<213> ORGANISM: Homo sapiens
<220> FEATURE:
<223> OTHER INFORMATION: Oligonucleotide

<400> SEQUENCE: 61
ggcauucucu uagcaucucu u          21

<210> SEQ ID NO 62
<211> LENGTH: 21
<212> TYPE: RNA
<213> ORGANISM: Homo sapiens
<220> FEATURE:
<223> OTHER INFORMATION: Oligonucleotide

<400> SEQUENCE: 62
gcagaagggc agauggacuu u          21

-continued

```
<210> SEQ ID NO 63
<211> LENGTH: 21
<212> TYPE: RNA
<213> ORGANISM: Homo sapiens
<220> FEATURE:
<223> OTHER INFORMATION: Oligonucleotide

<400> SEQUENCE: 63
aguucaucug cccuucugcu u                                             21
```